(12) United States Patent
Kishino et al.

(10) Patent No.: US 9,466,804 B2
(45) Date of Patent: Oct. 11, 2016

(54) ORGANIC LIGHT-EMITTING ELEMENT

(71) Applicant: CANON KABUSHIKI KAISHA, Tokyo (JP)

(72) Inventors: Kengo Kishino, Tokyo (JP); Takayuki Horiuchi, Tokyo (JP); Akihito Saitoh, Gotemba (JP); Jun Kamatani, Tokyo (JP); Naoki Yamada, Inagi (JP); Tetsuya Kosuge, Yokohama (JP); Shigemoto Abe, Yokohama (JP); Yosuke Nishide, Kawasaki (JP); Hirokazu Miyashita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/760,093

(22) PCT Filed: Jan. 7, 2014

(86) PCT No.: PCT/JP2014/050389
§ 371 (c)(1),
(2) Date: Jul. 9, 2015

(87) PCT Pub. No.: WO2014/112450
PCT Pub. Date: Jul. 24, 2014

(65) Prior Publication Data
US 2015/0357587 A1 Dec. 10, 2015

(30) Foreign Application Priority Data
Jan. 17, 2013 (JP) .................. 2013-006321

(51) Int. Cl.
*H01L 51/00* (2006.01)
*C09K 11/06* (2006.01)
(Continued)

(52) U.S. Cl.
CPC ....... *H01L 51/0085* (2013.01); *C07F 15/0033* (2013.01); *C09K 11/06* (2013.01);
(Continued)

(58) Field of Classification Search
CPC .......... H01L 51/0085; H01L 51/0077; H01L 51/0092; H01L 51/5206; H01L 2251/305; H01L 27/3248; H01L 51/5221; H01L 2251/5361; H01L 27/322; H01L 51/5016; C07F 15/0033; C09K 11/06; C09K 2211/1007
See application file for complete search history.

(56) References Cited

U.S. PATENT DOCUMENTS 6,824,894 B2 11/2004 Takiguchi et al.
7,078,115 B2 7/2006 Takiguchi et al.
(Continued)

FOREIGN PATENT DOCUMENTS

JP 2006-93197 A 4/2006
JP 2009-152568 A 7/2009
(Continued)

OTHER PUBLICATIONS

Pending U.S. Appl. No. 14/758,683, filed Jun. 30, 2015 (not yet published).

(Continued)

*Primary Examiner* — Michelle Mandala
(74) *Attorney, Agent, or Firm* — Fitzpatrick, Cella, Harper & Scinto

(57) ABSTRACT

Provided is an organic light-emitting element having high light-emitting efficiency and a long element lifetime. The organic light-emitting element includes an anode, a cathode, and an organic compound layer placed between the anode and the cathode, and the organic compound layer includes an iridium complex represented by the following general formula [1] and a metal complex represented by the following general formula [9].

$Ir(L_1)(L_2)(L_3)$ [1]

$MLL'$ [9].

13 Claims, 1 Drawing Sheet

(51) Int. Cl.
*C07F 15/00* (2006.01)
*H01L 51/52* (2006.01)
*H01L 27/32* (2006.01)
*H01L 51/50* (2006.01)

(52) U.S. Cl.
CPC ....... *H01L51/0077* (2013.01); *H01L 51/0092* (2013.01); *C09K 2211/1007* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1088* (2013.01); *C09K 2211/1092* (2013.01); *C09K 2211/181* (2013.01); *C09K 2211/185* (2013.01); *C09K 2211/186* (2013.01); *C09K 2211/188* (2013.01); *H01L 27/322* (2013.01); *H01L 27/3248* (2013.01); *H01L 51/5016* (2013.01); *H01L 51/5206* (2013.01); *H01L 51/5221* (2013.01); *H01L 2251/305* (2013.01); *H01L 2251/5361* (2013.01)

(56) References Cited

U.S. PATENT DOCUMENTS

| | | | |
|---|---|---|---|
| 7,232,618 B2 | 6/2007 | Yamada et al. | |
| 7,976,958 B2 | 7/2011 | Takiguchi et al. | |
| 8,268,455 B2 | 9/2012 | Kamatani et al. | |
| 8,330,153 B2 | 12/2012 | Ooishi et al. | |
| 2002/0034656 A1* | 3/2002 | Thompson | C07D 209/86 428/690 |
| 2005/0025995 A1* | 2/2005 | Cheng | C09K 11/06 428/690 |
| 2006/0186796 A1* | 8/2006 | Yabe | C07D 213/06 313/504 |
| 2007/0231601 A1 | 10/2007 | Nakasu et al. | |
| 2008/0210930 A1 | 9/2008 | Kamatani et al. | |
| 2008/0269491 A1 | 10/2008 | Jabbour et al. | |
| 2009/0039776 A1 | 2/2009 | Yamada et al. | |
| 2009/0159130 A1 | 6/2009 | Eum et al. | |
| 2009/0165860 A1 | 7/2009 | Kim et al. | |
| 2010/0219407 A1 | 9/2010 | Kamatani et al. | |
| 2010/0289406 A1 | 11/2010 | Ma et al. | |

FOREIGN PATENT DOCUMENTS

| | | |
|---|---|---|
| JP | 2009-218571 A | 9/2009 |
| WO | 2006/014599 A2 | 2/2006 |
| WO | 2007/143201 A1 | 12/2007 |
| WO | 2009/060995 A1 | 5/2009 |
| WO | 2010/028151 A1 | 3/2010 |
| WO | 2010/132524 A1 | 11/2010 |
| WO | 2012/107419 A1 | 8/2012 |

OTHER PUBLICATIONS

Pending U.S. Appl. No. 14/648,494, filed May 29, 2015 (not yet published).
Pending U.S. Appl. No. 14/648,095, filed May 28, 2015 (not yet published).
Pending U.S. Appl. No. 14/649,048, filed Jun. 2, 2015 (not yet published).
Pending U.S. Appl. No. 14/761,049, filed Jul. 15, 2015 (not yet published).
Pending U.S. Appl. No. 14/764,204, filed Jul. 29, 2015 (not yet published).
Pending U.S. Appl. No. 14/764,376, filed Jul. 29, 2015 (not yet published).
Y. Terao, et al., "Palladium-Catalyzed Cross-Coupling of Benzyl Ketones and Alpha, Beta-Unsaturated Carbonyl and Phenolic Compounds with o-Dibromobenzenes to Produce Cyclic Products," Bull. Chem. Soc. Jpn., vol. 72, pp. 2345-2350 (1999).

* cited by examiner

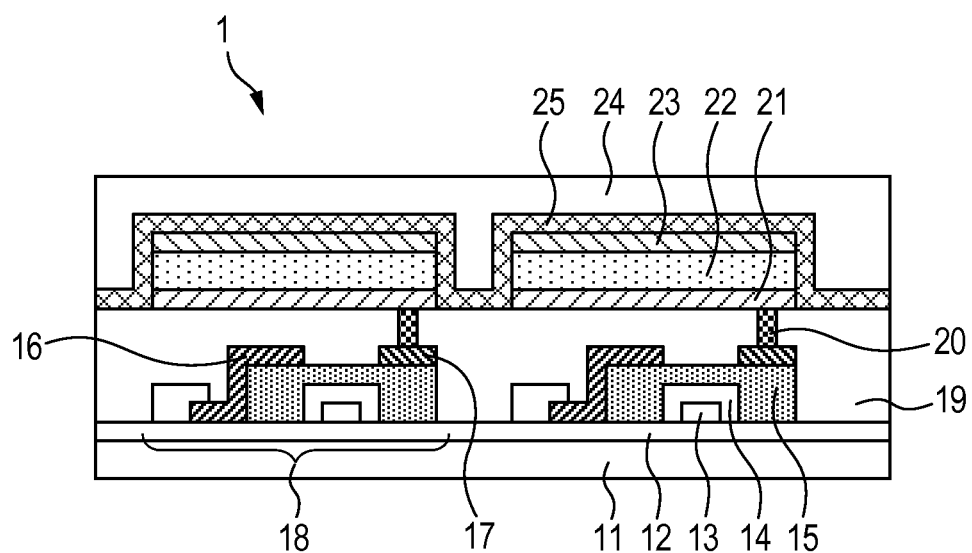

ORGANIC LIGHT-EMITTING ELEMENT

TECHNICAL FIELD

The present invention relates to an organic light-emitting element.

BACKGROUND ART

Organic light-emitting elements (organic electroluminescent elements or organic EL elements) are each an electronic element including an anode, a cathode, and an organic compound layer placed between both of these electrodes. A hole and electron injected from both the electrodes recombine in the organic compound layer to produce an exciton, and the organic light-emitting element emits light upon return of the exciton to its ground state. Recent advance of the organic light-emitting elements is significant and the advanced light-emitting elements have, for example, the following features. The elements can be driven at low voltages, emit light beams having various wavelengths, have high-speed responsiveness, and can be reduced in thickness and weight.

Of the organic light-emitting elements, a phosphorescent light-emitting element is an organic light-emitting element that: includes, in its organic compound layer, a material that emits phosphorescence; and provides light emission derived from a triplet exciton of the material that emits phosphorescence. In recent years, creation of a novel phosphorescent light-emitting material has been vigorously performed for providing a high-performance phosphorescent light-emitting element.

For example, a trivalent iridium complex having a metal-carbon bond has been frequently used as a guest material for a phosphorescent light-emitting element because of its high phosphorescence quantum yield. Patent Literature 1 describes, as a specific example of the iridium complex to be used as a guest, an iridium complex shown below in which three different kinds of bidentate ligands coordinate to iridium.

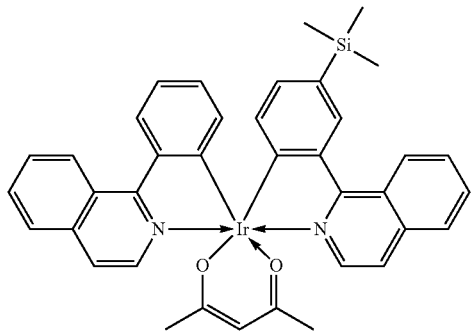

A metal complex to be incorporated as a host into an emission layer together with the iridium complex has also been known, and examples thereof include metal complexes disclosed in Patent Literature 2 and Patent Literature 3.

CITATION LIST

Patent Literature

PTL 1: International Patent WO2007/143201A
PTL 2: Japanese Patent Application Laid-Open No. 2009-152568
PTL 3: Japanese Patent Application Laid-Open No. 2009-218571
PTL 4: International Patent WO2010/028151A
PTL 5: International Patent WO2009/060995A Non Patent Literature NPL 1: Bull. Chem. Soc. Jpn. (1999). Vol. 72, 2345-2350

The present invention has been made to solve the problems and an object of the present invention is to provide an organic light-emitting element having high light-emitting efficiency and a long element lifetime.

SUMMARY OF INVENTION

Solution to Problem

According to one embodiment of the present invention, there is provided an organic light-emitting element, including:
an anode;
a cathode; and
an organic compound layer placed between the anode and the cathode,
in which the organic compound layer includes an iridium complex represented by the following general formula [1] and a metal complex represented by the following general formula [9].

$$Ir(L_1)(L_2)(L_3) \quad [1]$$

In the formula [1], a partial structure $IrL_1$ includes a partial structure represented by the following general formula [2].

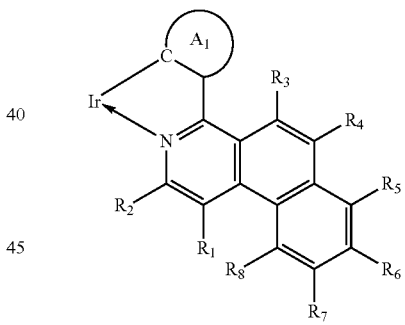

In the formula [2], a ring $A_1$ represents an aromatic ring or an aromatic heterocycle, and the aromatic ring and aromatic heterocycle each represented by the ring $A_1$ may each further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

$R_1$ to $R_8$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and may be identical to or different from one another, and when any one of substituents represented by the $R_1$ to $R_8$ is an alkyl group having 1 or more and 4 or less carbon atoms, an aralkyl group, an aryl group, a heterocyclic group, a substituted amino group, an alkoxy group, or an aryloxy group, the substituent may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

In the formula [1], a partial structure $IrL_2$ includes a partial structure represented by the following general formula [3].

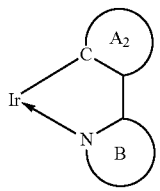

[3]

In the formula [3], a ring $A_2$ represents an aromatic ring or an aromatic heterocycle, and the aromatic ring and aromatic heterocycle each represented by the ring $A_2$ may each further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

A ring B represents a nitrogen-containing aromatic heterocycle, and the nitrogen-containing aromatic heterocycle represented by the ring B may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

$L_1$ and $L_2$ represent ligands that are different from each other and are not identical to each other.

In the formula [1], $L_3$ represents a monovalent bidentate ligand having an atom that forms a covalent bond with iridium and is selected from N, O, S, and P, and an atom that forms a coordinate bond with iridium and is selected from N, O, S, and P, and the atom that forms the covalent bond with iridium and the atom that forms the coordinate bond with iridium may be identical to or different from each other.

MLL'  [9]

In the formula [9], M represents a divalent metal atom selected from Zn, Be, Mg, Ca, Co, and Ni, L and L' each represent a bidentate ligand, L and L' may be identical to or different from each other, and ML and ML' each represent any one of partial structures represented by the following general formulae [10] to [15].

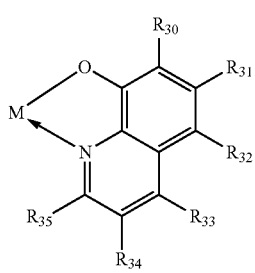

[10]

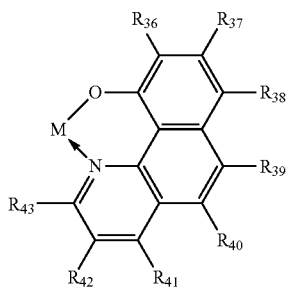

[11]

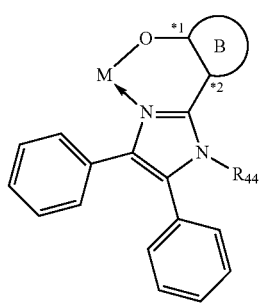

[12]

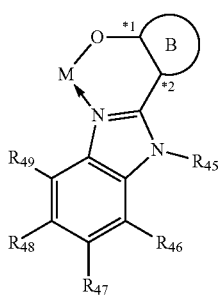

[13]

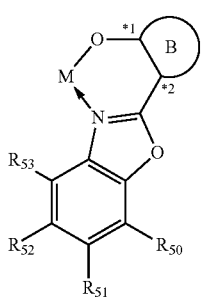

[14]

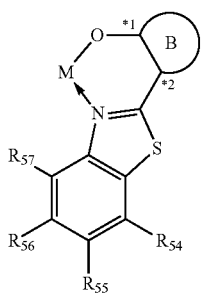

[15]

In the formulae [10] to [15], $R_{30}$ to $R_{57}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

In the formulae [12] to [15], a ring B includes any one of cyclic structures represented by the following general formulae [16] to [18].

*1 represents a bonding position with an oxygen atom and *2 represents a bonding position with a carbon atom in a five-membered heterocyclic skeleton.

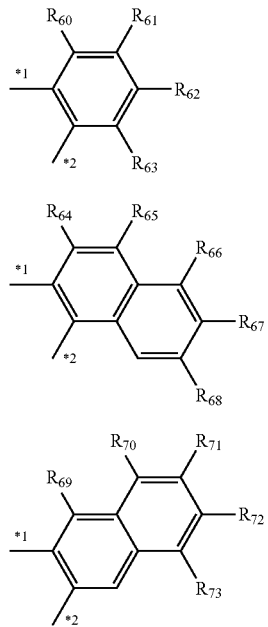

In the formulae [16] to [18], $R_{60}$ to $R_{73}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

Further features of the present invention will become apparent from the following description of exemplary embodiments with reference to the attached drawings.

BRIEF DESCRIPTION OF DRAWINGS

FIG. 1 is a schematic sectional view illustrating an organic light-emitting element and a switching element to be connected to the organic light-emitting element.

DESCRIPTION OF EMBODIMENTS

No reference has been made to the sublimability and heat stability of the complex proposed in Patent Literature 1, and hence whether or not its sublimation purification or vacuum deposition can be performed is unclear. In addition, with regard to an organic light-emitting element whose emission layer contains the metal complex disclosed in Patent Literature 2 or Patent Literature 3 as a host, the light-emitting efficiency of the resultant organic light-emitting element has been low.

Hereinafter, the present invention is described in detail.
(1) Organic Light-Emitting Element An organic light-emitting element of the present invention is a light-emitting element including at least: an anode and a cathode; and an organic compound layer placed between the anode and the cathode. In addition, the organic light-emitting element of the present invention includes, in the organic compound layer, an iridium complex represented by the following general formula [1] and a metal complex compound represented by the following general formula [9].

$$Ir(L_1)(L_2)(L_3) \quad [1]$$

$$MLL' \quad [9]$$

It should be noted that details about the iridium complex represented by the general formula [1] and the metal complex represented by the general formula [9] are described later.

The element construction of the organic light-emitting element of the present invention is, for example, a multilayer-type element construction obtained by sequentially laminating, on a substrate, electrode layers and an organic compound layer described in each of the following constructions (1) to (6). It should be noted that in each of the element constructions, the organic compound layer necessarily includes an emission layer including a light-emitting material.

(1) Anode/emission layer/cathode
(2) Anode/hole transport layer/emission layer/electron transport layer/cathode
(3) Anode/hole transport layer/emission layer/electron transport layer/electron injection layer/cathode
(4) Anode/hole injection layer/hole transport layer/emission layer/electron transport layer/cathode
(5) Anode/hole injection layer/hole transport layer/emission layer/electron transport layer/electron injection layer/cathode
(6) Anode/hole transport layer/electron blocking layer/emission layer/hole blocking layer/electron transport layer/cathode It should be noted that those element construction examples are only very basic element constructions and the element construction of the organic light-emitting element of the present invention is not limited thereto.

For example, the following various layer constructions can each be adopted: an insulating layer, an adhesion layer, or an interference layer is provided at an interface between an electrode and the organic compound layer, the electron transport layer or the hole transport layer is constituted of two layers having different ionization potentials, or the emission layer is constituted of two layers including different light-emitting materials.

In the present invention, the aspect according to which light output from the emission layer is extracted (element form) may be the so-called bottom emission system in which the light is extracted from an electrode on a side closer to the substrate or may be the so-called top emission system in which the light is extracted from a side opposite to the substrate. In addition, a double-face extraction system in which the light is extracted from each of the side closer to the substrate and the side opposite to the substrate can be adopted.

Of the element constructions (1) to (6), the construction (6) is preferred because the construction includes both the electron blocking layer and the hole blocking layer. In other words, the construction (6) including the electron blocking layer and the hole blocking layer provides an organic light-emitting element that does not cause any carrier leakage and has high light-emitting efficiency because both carriers, i.e., a hole and an electron can be trapped in the emission layer with reliability.

In the organic light-emitting element of the present invention, the iridium complex represented by the general formula [1] and the metal complex compound represented by the general formula [9] are preferably incorporated into the emission layer out of the organic compound layer. In this case, the emission layer includes at least the iridium complex represented by the general formula [1] and the metal complex compound represented by the general formula [9]. The applications of the compounds to be incorporated into the emission layer in this case vary depending on their content concentrations in the emission layer. Specifically, the compounds are classified into a main component and a sub-component depending on their content concentrations in the emission layer.

The compound serving as the main component is a compound having the largest weight ratio (content concentration) out of the group of compounds to be incorporated into the emission layer and is a compound also called a host. In addition, the host is a compound present as a matrix around the light-emitting material in the emission layer, and is a compound mainly responsible for the transport of a carrier to the light-emitting material and the donation of an excitation energy to the light-emitting material.

In addition, the compound serving as the sub-component is a compound except the main component and can be called a guest (dopant), a light emission assist material, or a charge-injecting material depending on a function of the compound. The guest as one kind of sub-component is a compound (light-emitting material) responsible for main light emission in the emission layer. The light emission assist material as one kind of sub-component is a compound that assists the light emission of the guest and is a compound having a smaller weight ratio (content concentration) in the emission layer than that of the host. The light emission assist material is also called a second host by virtue of its function.

The concentration of the guest with respect to the host is 0.01 wt % or more and 50 wt % or less, preferably 0.1 wt % or more and 20 wt % or less with reference to the total amount of the constituent materials for the emission layer. The concentration of the guest is particularly preferably 1 wt % or more and 15 wt % or less from the viewpoint of preventing concentration quenching.

In the present invention, the guest may be uniformly incorporated into the entirety of the layer in which the host serves as a matrix, or may be incorporated so as to have a concentration gradient. In addition, the guest may be partially incorporated into a specific region in the emission layer to make the layer a layer having a region free of the guest and formed only of the host.

In the present invention, the following aspect is preferred: both the iridium complex represented by the general formula [1] and the metal complex compound represented by the general formula [9] are incorporated as the guest and the host, respectively, into the emission layer. In this case, in addition to the iridium complex represented by the general formula [1], another phosphorescent light-emitting material may be further incorporated into the emission layer for assisting the transfer of an exciton or a carrier.

In addition, a compound different from the metal complex compound represented by the general formula [9] may be further incorporated as the second host (or the light emission assist material) into the emission layer for assisting the transfer of the exciton or the carrier. When the second host (or the light emission assist material) is incorporated into the emission layer, the second host (or the light emission assist material) is desirably incorporated at less than 50 wt % with reference to the total amount of the constituent materials for the emission layer.

(2) Iridium Complex

In the organic light-emitting element of the present invention, the iridium complex to be incorporated as the guest into the emission layer is a compound represented by the following general formula [1].

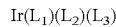

$$\text{Ir}(L_1)(L_2)(L_3) \qquad [1]$$

In the general formula [1], $L_1$, $L_2$, and $L_3$ represent bidentate ligands different from one another. Here, a partial structure $\text{Ir}L_1$ is specifically a partial structure represented by the following general formula [2].

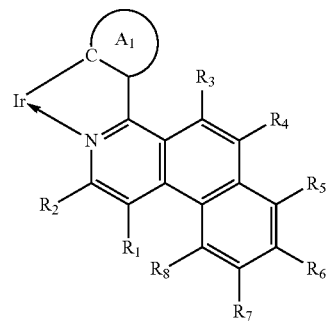

[2]

In the general formula [2], a ring $A_1$ represents an aromatic ring or an aromatic heterocycle.

Examples of the aromatic ring represented by the ring $A_1$ include, but, of course, not limited to, a benzene ring, a naphthalene ring, a fluorene ring, a phenanthrene ring, an anthracene ring, a chrysene ring, a triphenylene ring, and a pyrene ring. Of those, a benzene ring, a naphthalene ring, a fluorene ring, or a phenanthrene ring is preferred from the viewpoint of controlling the color of the phosphorescence of the iridium complex represented by the general formula [1] to an orange color to a red color.

Examples of the aromatic heterocycle represented by the ring $A_1$ include, but, of course, not limited to, a thiophene ring, a furan ring, an imidazole ring, a pyridine ring, a benzothiophene ring, a benzofuran ring, a quinoline ring, a carbazole ring, a dibenzofuran ring, and a dibenzothiophene ring. Of those, a carbazole ring, a dibenzofuran ring, or a dibenzothiophene ring is preferred from the viewpoint of controlling the color of the phosphorescence of the iridium complex represented by the general formula [1] to an orange color to a red color.

It should be noted that in the present invention, the aromatic ring and aromatic heterocycle each represented by the ring $A_1$ may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, a pyrenyl group, a dimethylphenyl group, or a difluorophenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, a dibenzothienyl group, or a dimethylpyridyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxyl group such as a phenoxy group; a halogen atom such as a fluorine, chlorine, bromine, or iodine atom; a trifluoromethyl group; and a cyano group. Here, the alkyl group that the aromatic ring and aromatic heterocycle each represented by the ring $A_1$ may further have also includes an alkyl group in which a hydrogen atom in the substituent is substituted with a fluorine atom.

In the general formula [2], $R_1$ to $R_8$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group.

Examples of the alkyl group represented by any one of $R_1$ to $R_8$ include a methyl group, an ethyl group, an n-propyl group, an isopropyl group, an n-butyl group, a 1-methylpropyl group, a 2-methylpropyl group, and a tert-butyl group.

Examples of the aralkyl group represented by any one of $R_1$ to $R_8$ include a benzyl group and a phenethyl group.

Examples of the aryl group represented by any one of $R_1$ to $R_8$ include a phenyl group, a biphenyl group, a terphenyl group, a naphthyl group, a fluorenyl group, a phenanthrenyl group, an anthracenyl group, a chrysenyl group, a triphenylenyl group, and a pyrenyl group.

Examples of the heterocyclic group represented by any one of $R_1$ to $R_8$ include a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, and a dibenzothienyl group.

Examples of the substituted amino group represented by any one of $R_1$ to $R_8$ include a dimethylamino group, a diethylamino group, a dibenzylamino group, a diphenylamino group, and a ditolylamino group.

Examples of the alkoxy group represented by any one of $R_1$ to $R_8$ include a methoxy group, an ethoxy group, an isopropoxy group, and a tert-butoxy group.

An example of the aryloxy group represented by any one of $R_1$ to $R_8$ is a phenoxy group.

Examples of the halogen atom represented by any one of $R_1$ to $R_8$ include fluorine, chlorine, bromine, and iodine atoms.

Substituents represented by $R_1$ to $R_8$, in particular, substituents represented by $R_5$ to $R_8$ are each preferably an alkyl group or a phenyl group. This is because an alkyl group and a phenyl group each weaken an intermolecular interaction between complex molecules such as π-π stacking. In addition, an intermolecular interaction when alkyl groups or phenyl groups are brought close to each other is weak, and hence the intermolecular interaction between the complex molecules is not strengthened. It should be noted that a phenyl group has a small ring plane and hence acts as an alienating group rather than causing the π-π stacking.

It should be noted that upon introduction of alkyl groups as the substituents represented by $R_1$ to $R_8$, the alkyl groups to be introduced are each preferably an alkyl group having 1 or more and 4 or less carbon atoms because the sublimability of the complex itself reduces when the number of carbon atoms is excessively large. The same holds true for alkyl groups that can be incorporated into the ligands $L_2$ and $L_3$.

In the general formula [2], $R_1$ to $R_8$ may be identical to or different from one another.

It should be noted that when any one of the substituents represented by $R_1$ to $R_8$ is an alkyl group having 1 or more and 4 or less carbon atoms, an aralkyl group, an aryl group, a heterocyclic group, a substituted amino group, an alkoxy group, or an aryloxy group, the substituent of interest may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group. Here, the alkyl group that the substituents represented by $R_1$ to $R_8$ may further have also includes an alkyl group in which a hydrogen atom in the substituent is substituted with a fluorine atom.

The partial structure represented by the general formula [2] is preferably a partial structure represented the following general formula [4].

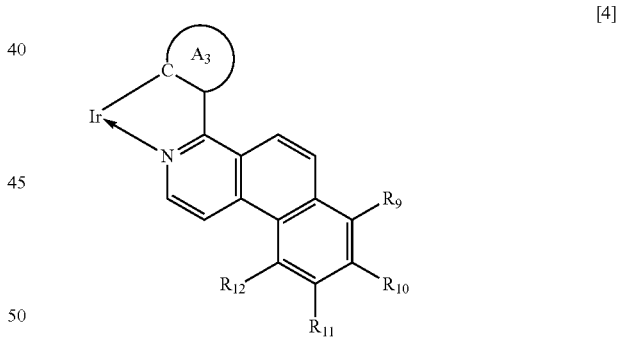

[4]

In the general formula [4], a ring $A_3$ is a ring structure selected from a benzene ring, a naphthalene ring, a fluorene ring, a phenanthrene ring, a carbazole ring, a dibenzofuran ring, and a dibenzothiophene ring.

It should be noted that the ring $A_3$ may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

In the general formula [4], $R_9$ to $R_{12}$ each represent a hydrogen atom, an alkyl group having 1 or more and 4 or less carbon atoms, or a phenyl group, and may be identical to or different from one another.

Specific examples of the alkyl group having 1 or more and 4 or less carbon atoms and phenyl group each represented by any one of $R_9$ to $R_{12}$ are same as the specific examples of $R_1$ to $R_8$ in the general formula [2].

It should be noted that when any one of the substituents each represented by $R_9$ to $R_{12}$ is an alkyl group having 1 or more and 4 or less carbon atoms or a phenyl group, or the corresponding substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

In the general formula [1], a partial structure $IrL_2$ is a partial structure represented by the following general formula [3].

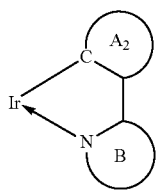

[3]

In the general formula [3], a ring $A_2$ represents an aromatic ring or an aromatic heterocycle. Specific examples of the aromatic ring represented by the ring $A_2$ are the same as the specific examples of the ring $A_1$ in the formula [2]. The aromatic ring is preferably a benzene ring, a naphthalene ring, a fluorene ring, or a phenanthrene ring because any such ring can form a stable complex with trivalent iridium.

In addition, specific examples of the aromatic heterocycle represented by the ring $A_2$ are the same as the specific examples of the ring $A_1$ in the formula [2]. The aromatic heterocycle is preferably a carbazole ring, a dibenzofuran ring, or a dibenzothiophene ring because any such heterocycle can form a stable complex with trivalent iridium.

It should be noted that the ring $A_2$ may further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group. Here, specific examples of the alkyl group having 1 or more and 4 or less carbon atoms, the aralkyl group, the aryl group, the heterocyclic group, the substituted amino group, the alkoxy group, the aryloxy group, and the halogen atom each serving as a substituent that the ring $A_2$ may further have are the same as the specific examples in the ring $A_1$ in the formula [2].

In the general formula [3], a ring B represents a nitrogen-containing aromatic heterocycle.

Examples of the nitrogen-containing aromatic heterocycle represented by the ring B include, but, of course, not limited to, a pyridine ring, a pyrimidine ring, a pyrazine ring, a triazine ring, a quinoline ring, an isoquinoline ring, a benzo[f]quinoline ring, a benzo[h]quinoline ring, a benzo[f]isoquinoline ring, a benzo[h]isoquinoline ring, an oxazole ring, a benzo[d]oxazole ring, a benzo[d]thiazole ring, an imidazole ring, and a pyrazole ring. Of those, a pyridine ring, a quinoline ring, a benzo[f]quinoline ring, a benzo[h]quinoline ring, a benzo[f]isoquinoline ring, a benzo[h]isoquinoline ring, an oxazole ring, a benzo[d]oxazole ring, a benzo[d]thiazole ring, or an imidazole ring because any such heterocycle can form a stable complex with trivalent iridium.

It should be noted that in the general formula [3], the ring B may further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group. Here, specific examples of the alkyl group having 1 or more and 4 or less carbon atoms, the aralkyl group, the aryl group, the heterocyclic group, the substituted amino group, the alkoxy group, the aryloxy group, and the halogen atom each serving as a substituent that the ring B may further have are same as the specific examples in the ring $A_1$ in the formula [2].

A partial structure represented by the following general formula [5] is preferred as the partial structure represented by the general formula [3].

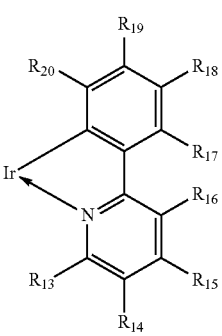

[5]

In the general formula [5], $R_{13}$ to $R_{20}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group. The substituents represented by $R_{13}$ to $R_{20}$ may be identical to or different from one another.

It should be noted that specific examples of the alkyl group having 1 or more and 4 or less carbon atoms, aralkyl group, aryl group, heterocyclic group, substituted amino group, alkoxy group, aryloxy group, and halogen atom represented by $R_{13}$ to $R_{20}$ are same as the specific examples of $R_1$ to $R_8$ in the general formula [2]. In addition, when any one of the substituents represented by $R_{13}$ to $R_{20}$ is an alkyl group having 1 or more and 4 or less carbon atoms, an aralkyl group, an aryl group, a heterocyclic group, a substituted amino group, an alkoxy group, or an aryloxy group, the corresponding substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

In the general formula [5], $R_{13}$ to $R_{20}$ each preferably represent a hydrogen atom, an alkyl group having 1 or more and 4 or less carbon atoms, or a phenyl group. This is because an alkyl group having 1 or more and 4 or less carbon atoms, and a phenyl group are each a substituent that reduces an intermolecular interaction between molecules of the complex. It should be noted that when any one of $R_{13}$ to $R_{20}$ represents an alkyl group having 1 or more and 4 or less carbon atoms, or a phenyl group, the corresponding substituent may further have an alkyl group having 1 or more and 4 or less carbon atoms, an aralkyl group, an aryl group, a heterocyclic group, a substituted amino group, an alkoxy group, an aryloxy group, a halogen atom, or a cyano group.

In the present invention, the ligand $L_1$ and the ligand $L_2$ are different from each other and are not identical to each other.

In the general formula [1], $L_3$ represents a monovalent bidentate ligand having an atom that forms a covalent bond with iridium and is selected from N, O, S, and P, and an atom that forms a coordinate bond with iridium and is selected from N, O, S, and P. In the present invention, the atom that forms the covalent bond with iridium and atom that forms the coordinate bond with iridium in $L_3$ may be identical to or different from each other.

Examples of the ligand represented by $L_3$ include β-diketonate, picolinate, 2-aminoethanethiolate, 2-aminobenzenethiolate, and 2-(diphenylphosphino)phenolate. However, the ligand is not limited to the compound group as long as the ligand forms a stable complex with trivalent iridium and does not largely reduce the emission quantum yield of the complex itself.

In the present invention, a partial structure $IrL_3$ is preferably a structure represented by the following general formula [6].

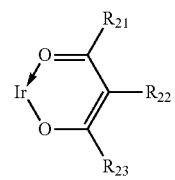

[6]

In the general formula [6], $R_{21}$ to $R_{23}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and may be identical to or different from one another.

It should be noted that specific examples of the alkyl group having 1 or more and 4 or less carbon atoms, aralkyl group, aryl group, heterocyclic group, substituted amino group, alkoxy group, and aryloxy group represented by $R_{21}$ to $R_{23}$ are same as the specific examples of $R_1$ to $R_8$ in the general formula [2]. In addition, when any one of the substituents represented by $R_{21}$ to $R_{23}$ is an alkyl group having 1 or more and 4 or less carbon atoms, an aralkyl group, an aryl group, a heterocyclic group, a substituted amino group, an alkoxy group, or an aryloxy group, the corresponding substituent may further have a substituent selected from: an alkyl group having 1 or more and 4 or less carbon atoms selected from a methyl group, an ethyl group, an n-propyl group, an isopropyl group, an n-butyl group, a 1-methylpropyl group, a 2-methylpropyl group, and a tert-butyl group; an aralkyl group such as a benzyl group or a phenethyl group; an aryl group such as a phenyl group, a biphenyl group, a terphenyl group, a naphthyl group, a fluorenyl group, a phenanthrenyl group, an anthracenyl group, a chrysenyl group, a triphenylenyl group, or a pyrenyl group; a heterocyclic group such as a thienyl group, a furanyl group, an imidazolyl group, a 1-pyrrolidinyl group, a pyridyl group, a benzothienyl group, a benzofuranyl group, a quinolyl group, a carbazolyl group, a dibenzofuranyl group, or a dibenzothienyl group; a substituted amino group such as a dimethylamino group, a diethylamino group, a dibenzylamino group, a diphenylamino group, or a ditolylamino group; an alkoxy group such as a methoxy group, an ethoxy group, an isopropoxy group, or a tert-butoxy group; an aryloxy group such as a phenoxy group; a halogen atom such as a fluorine, chlorine, bromine, or iodine atom; and a cyano group.

In the general formula [6], $R_{21}$ to $R_{23}$ each preferably represent a hydrogen atom or an alkyl group having 1 or more and 4 or less carbon atoms. It should be noted that when any one of the substituents represented by $R_{21}$ to $R_{23}$ is an alkyl group having 1 or more and 4 or less carbon atoms, the corresponding substituent may further have an alkyl group having 1 or more and 4 or less carbon atoms, an aralkyl group, an aryl group, a heterocyclic group, a substituted amino group, an alkoxy group, an aryloxy group, a halogen atom, or a cyano group. $R_{21}$ to $R_{23}$ each more preferably represent a hydrogen atom or an alkyl group having 1 or more and 4 or less carbon atoms. When $R_{21}$ to $R_{23}$ each represent a hydrogen atom, its molecular weight reduces and hence the sublimability of the complex itself can be improved. In addition, when $R_{21}$ to $R_{23}$ each represent an alkyl group having 1 or more and 4 or less carbon atoms, an interaction between molecules of the complex reduces and hence the sublimability of the complex itself can be improved.

(Method of Synthesizing Iridium Complex)

Next, a method of synthesizing the iridium complex of the present invention is described. The iridium complex of the present invention is synthesized by, for example, a synthesis scheme 1 shown below.

<Synthesis Scheme 1>

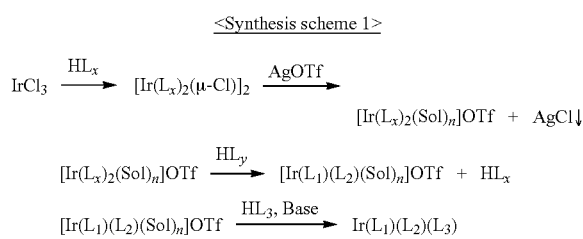

($L_x$ represents $L_1$ or $L_2$, Sol represents a solvent molecule, n represents an integer, when the solvent molecule is a monodentate ligand, n represents 2, when the solvent molecule is a ligand that is bidentate or more, n represents 1, when $L_x$ represents $L_1$, $L_y$ represents $L_2$, and when $L_x$ represents $L_2$, $L_y$ represents $L_1$.)

A synthesis process in the synthesis scheme 1 is described below.

First, a triflate form of an iridium complex having two $L_1$'s or $L_2$'s is synthesized according to a method described in Patent Literature 4.

Next, the triflate form of the iridium complex and a compound $HL_2$ or $HL_1$ including a ligand are heated in a solution. Thus, ligand exchange is performed. It should be noted that upon performance of a ligand exchange reaction, the concentration of the solution is properly adjusted before the reaction is performed because a form to which three luminous ligands coordinate is produced when the concentration is high. It should be noted that upon performance of the ligand exchange reaction, a reaction check is desirably performed as appropriate by taking out part of the solution and causing the solution to react with $HL_3$. In addition, while the reaction check is performed as appropriate, the heating is continued until the concentration of a product shows no change.

Next, the iridium complex of the present invention can be synthesized by adding $HL_3$ and a base to the reaction solution. It should be noted that the resultant may contain $Ir(L_1)_2 (L_3)$ or $Ir(L_2)_2 (L_3)$ as a by-product and hence the by-product needs to be appropriately removed by column purification.

Meanwhile, the iridium complex of the present invention can be synthesized according to a method described in Non Patent Literature 1. The method is specifically a method of synthesizing the complex by a synthesis scheme 2 shown below.

<Synthesis Scheme 2>

$$[Ir(COD)(\mu\text{-}Cl)]_2 \xrightarrow{HL_1, HL_2} [Ir(L_1)(L_2)(\mu\text{-}Cl)]_2$$

-continued

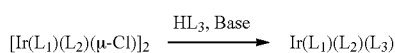

A synthesis process in the synthesis scheme 2 is described below.

First, $[Ir(COD)(\mu\text{-}Cl)]_2$ (COD: 1,5-cyclooctadiene), which is an iridium complex, is used as a starting raw material, and $HL_1$ and $HL_2$ are caused to react with the iridium complex simultaneously. Thus, the reaction product is obtained in the form of a mixture containing a chloro-crosslinked dimer ($[Ir(L_1)(L_2)(\mu\text{-}Cl)]_2$) having the ligands $L_1$ and $L_2$.

Next, the mixture and $HL_3$ are caused to react with each other under a basic condition. A crude product produced by the reaction is subjected to column purification to provide the iridium complex of the present invention.

Here, the employment of the second production method typically provides, as a main component, a complex in which nitrogen atoms in $L_1$ and $L_2$, and iridium are coaxially placed like N—Ir—N. At this time, a structural isomer is sometimes produced as a by-product but even a mixture containing the isomer as a by-product is used in some cases in terms of cost.

In addition, when the complex is obtained as a mixture of enantiomers, the mixture may be used without being treated or may be subjected to optical resolution depending on intended purposes.

(3) Metal Complex Compound Serving as Host

Next, the metal complex compound to be used as the host for the emission layer of the organic light-emitting element of the present invention is described. The metal complex compound serving as the host to be incorporated into the organic light-emitting element of the present invention is specifically a compound represented by the following general formula [9].

MLL'  [9]

In the formula [9], M represents a divalent metal atom selected from Zn, Be, Mg, Ca, Co, and Ni. Of those, Zn, Be, or Mg is preferred.

In the formula [9], L and L' each represent a bidentate ligand. It should be noted that L and L' may be identical to or different from each other.

In the formula [9], ML and ML' each represent any one of partial structures represented by the following general formulae [10] to [15].

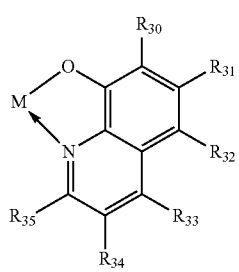

[10]

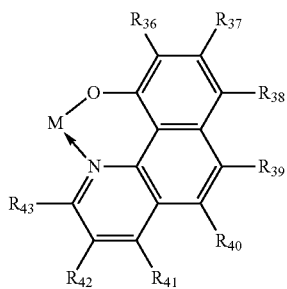

[11]

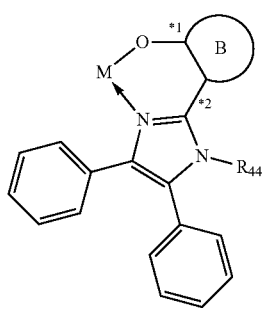

[12]

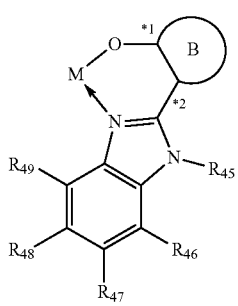

[13]

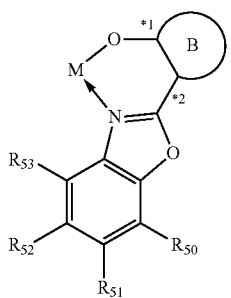

[14]

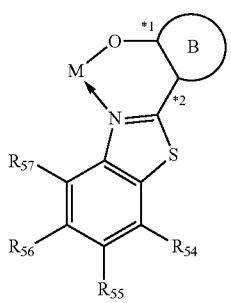

[15]

In the formulae [10] to [15], $R_{30}$ to $R_{57}$ each represent a hydrogen atom, a halogen atom, a substituted or unsubstituted alkyl group, an alkoxy group, an aryloxy group, an aralkyl group, a substituted amino group, a substituted or unsubstituted aromatic hydrocarbon group, or a substituted or unsubstituted heteroaromatic group.

Specific examples of the halogen atom represented by any one of $R_{30}$ to $R_{57}$ include fluorine, chlorine, bromine, and iodine atoms.

The alkyl group represented by any one of $R_{30}$ to $R_{57}$ is preferably an alkyl group having 1 or more and 6 or less carbon atoms. Specific examples of the alkyl group having 1 or more and 6 or less carbon atoms include a methyl group, an ethyl group, an n-propyl group, an i-propyl group, an n-butyl group, an i-butyl group, a sec-butyl group, a tert-butyl group, an n-pentyl group, an i-pentyl group, a tert-pentyl group, a neopentyl group, an n-hexyl group, and a cyclohexyl group. Of those alkyl groups, a methyl group or a tert-butyl group is particularly preferred.

Specific examples of the alkoxy group represented by any one of $R_{30}$ to $R_{57}$ include, but, of course, not limited to, a methoxy group, an ethoxy group, an i-propoxy group, an n-butoxy group, a tert-butoxy group, a 2-ethyl-octyloxy group, and a benzyloxy group. Of those alkoxy groups, a methoxy group or an ethoxy group is preferred.

Examples of the aryloxy group represented by any one of $R_{30}$ to $R_{57}$ include, but, of course, not limited to, a phenoxy group, a 4-tert-butylphenoxy group, and a thienyloxy group.

An example of the aralkyl group represented by any one of $R_{30}$ to $R_{57}$ is, but, of course, not limited to, a benzyl group.

Examples of the substituted amino group represented by any one of $R_{30}$ to $R_{57}$ include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisoylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Specific examples of the aromatic hydrocarbon group represented by any one of $R_{30}$ to $R_{57}$ include, but, of course, not limited to, a phenyl group, a naphthyl group, a phenanthryl group, an anthryl group, a fluorenyl group, a biphenylenyl group, an acenaphthylenyl group, a chrysenyl group, a pyrenyl group, a triphenylenyl group, a picenyl group, a fluoranthenyl group, a perylenyl group, a naphthacenyl group, a biphenyl group, and a terphenyl group. Of those aromatic hydrocarbon groups, a phenyl group, a naphthyl group, a fluorenyl group, or a biphenyl group is preferred, and a phenyl group is more preferred.

Specific examples of the heteroaromatic group represented by any one of $R_{30}$ to $R_{57}$ include, but, of course, not limited to, a thienyl group, a pyrrolyl group, a pyrazinyl group, a pyridyl group, an indolyl group, a quinolyl group, an isoquinolyl group, a naphthyridinyl group, an acridinyl group, a phenanthrolinyl group, a carbazolyl group, a benzo[a]carbazolyl group, a benzo[b]carbazolyl group, a benzo[c]carbazolyl group, a phenazinyl group, a phenoxazinyl group, a phenothiazinyl group, a benzothiophenyl group, a dibenzothiophenyl group, a benzofuranyl group, a dibenzofuranyl group, an oxazolyl group, and an oxadiazolyl group.

Examples of the substituent that the alkyl group, the aryl group, and the heterocyclic group each may further have include: alkyl groups such as a methyl group, an ethyl group, and a propyl group; aralkyl groups such as a benzyl group; aryl groups such as a phenyl group, a biphenyl group, and a tetrakis(9,9-dimethylfluorenyl) group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, and a propoxyl group; aryloxyl groups such as a phenoxyl group; halogen atoms such as fluorine, chlorine, bromine, and iodine atoms; and a cyano group.

The substituents represented in any one of the formulae [10] to [15], i.e., $R_{30}$ to $R_{57}$ each preferably represent a hydrogen atom, an alkyl group having 1 to 4 carbon atoms, or a phenyl group that may be substituted with an alkyl group having 1 to 4 carbon atoms.

In the formulae [11] to [15], *1 represents a bonding position with an oxygen atom and *2 represents a bonding position with a carbon atom sandwiched between heteroatoms in a heterocyclic five-membered ring skeleton represented below.

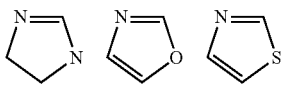

In the formulae [12] to [15], a ring B is any one of cyclic structures represented by the following general formulae [16] to [18].

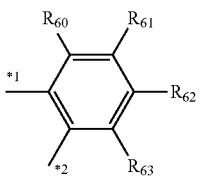

[16]

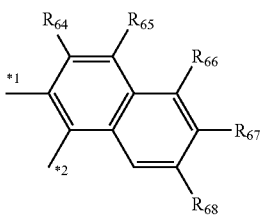

[17]

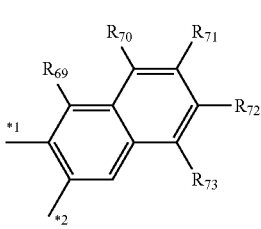

[18]

In the formulae [16] to [18], $R_{60}$ to $R_{73}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

Specific examples of the halogen atom, alkyl group, alkoxy group, aryloxy group, aralkyl group, substituted amino group, aromatic hydrocarbon group, and heteroaromatic group represented by $R_{60}$ to $R_{73}$, and the substituent that the alkyl group, the aromatic hydrocarbon group, and the heteroaromatic group each may further have are the same as the specific examples in $R_{30}$ to $R_{57}$ in the general formulae [10] to [15].

The substituents represented in any one of the formulae [16] to [18], i.e., $R_{60}$ to $R_{73}$ each preferably represent a hydrogen atom, an alkyl group having 1 to 4 carbon atoms, or a phenyl group that may be substituted with an alkyl group having 1 to 4 carbon atoms.

By the way, in the organic light-emitting element according to this embodiment, the basic skeleton of each of both the iridium complex represented by the general formula [1] and the metal complex represented by the general formula [9] can be appropriately provided with a substituent, which can change an emission wavelength, a band gap, an HOMO-LUMO, or the like. It should be noted that the provision of the basic skeleton with an excessively large number of substituents may reduce the sublimability of the complex itself.

From the viewpoint, $R_1$ to $R_8$ in the general formula [1] each preferably represent a substituent having a molecular weight of 100 or less such as an alkyl group having 1 to 4 carbon atoms, a methoxy group, an ethoxy group, a phenyl group, a pyridyl group, a fluorine group, or a cyano group.

(4) Actions Exhibited by Host and Guest

Next, actions exhibited by the host and guest to be incorporated into the emission layer in the organic light-emitting element of the present invention are described.

(4-1) Action Exhibited by Guest

The iridium complex represented by the general formula [1] as the guest is a complex compound formed of trivalent iridium and three kinds of ligands ($L_1$, $L_2$, and $L_3$) that are not identical to one another in structure. In the iridium complex represented by the general formula [1], the three kinds of ligands in the complex are different from one another particularly from a structural viewpoint. Accordingly, the iridium complex represented by the general formula [1] becomes a complex having no symmetry. Therefore, the iridium complex represented by the general formula [1] has low crystallinity in a solid state and an energy for bonding molecules of the complex is small. As a result, the iridium complex represented by the general formula [1] has high sublimability. It should be noted that details about the sublimability of the complex are described later.

First, the three kinds of ligands of the iridium complex are described.

Of the three kinds of ligands, $L_1$ and $L_2$ each have a carbon atom that forms a covalent bond with iridium and a nitrogen atom that forms a coordinate bond with iridium. In addition, $L_1$ and $L_2$ each serve as a ligand that coordinates to iridium to form a five-membered ring formed of iridium and a partial skeleton N—C—C—C, thereby affecting the phosphorescence characteristics of the complex. That is, the ligands $L_1$ and $L_2$ are each a ligand called a luminous ligand. On the other hand, $L_3$ is called an auxiliary ligand because of its small contribution to the phosphorescence characteristics, though $L_3$ is a monovalent bidentate ligand as in $L_1$ and $L_2$.

First, $L_1$ as a luminous ligand is described. $L_1$ is a ligand having a benzo[f]quinoline skeleton as a basic skeleton and the ring $A_1$ that is an aromatic ring or an aromatic heterocycle. The selection of a predetermined aromatic ring or aromatic heterocycle as the ring $A_1$ causes the partial structure $IrL_1$ including $L_1$ to form a triplet energy level that generates phosphorescence having a wavelength equal to or longer than that of an orange color. In the present invention, the phosphorescence having a wavelength equal to or longer than that of an orange color refers to such light that the maximum peak wavelength of a phosphorescence spectrum is 580 nm or more.

Here, proper selection of the ring $A_1$ causes the partial structure $IrL_1$ to form a triplet energy level that generates phosphorescence whose color ranges from an orange color to a red color. In the present invention, the phosphorescence whose color ranges from an orange color to a red color refers to such light that the maximum peak wavelength of a phosphorescence spectrum is 580 nm or more and 650 nm or less. Phosphorescence having a wavelength in the region can be suitably applied to a display apparatus, a lighting apparatus, or an exposure light source for an image-forming apparatus of an electrophotographic system.

By the way, the benzo[f]quinoline skeleton in the ligand $L_1$ is liable to interact with a benzo[f]quinoline skeleton in an adjacent complex. That is, ring planes in the benzo[f]quinoline skeletons may overlap each other to cause $\pi$-$\pi$ stacking. As a result, an energy for bonding molecules of the complex to each other increases to reduce the sublimability.

In order that the $\pi$-$\pi$ stacking may be suppressed, the benzo[f]quinoline skeleton is preferably provided with a substituent as appropriate to inhibit the approach of the ring planes. In particular, a substituent (preferably an alkyl group having 1 to 4 carbon atoms or a phenyl group) is introduced into a substituent bonded to a carbon atom distant from iridium out of the carbon atoms in the benzo[f]quinoline skeleton, specifically, any one of $R_5$ to $R_8$ in the general formula [2]. Thus, the approach of the ring planes can be additionally inhibited.

Next, the ligand $L_2$ is described. $L_2$ is a luminous ligand as in $L_1$, and is a ligand formed of two kinds of ring structures, i.e., the ring $A_2$ and the ring B. The ring $A_2$ is appropriately selected from an aromatic ring and an aromatic heterocyclic group, and the ring B is appropriately selected from nitrogen-containing aromatic rings depending on desired purposes. Of those, a skeleton capable of forming a stable complex with trivalent iridium is preferred.

The iridium complex of the present invention generates only phosphorescence derived from a partial structure having the lower triplet energy level out of the partial structures $IrL_1$ and $IrL_2$. This is because energy transfer from the partial structure having the higher triplet energy level to the partial structure having the lower triplet energy level occurs. Which partial structure is caused to emit phosphorescence can be appropriately selected depending on desired purposes.

Here, when the luminescent color is changed from an orange color to a red color, molecular design is preferably performed so that phosphorescence may be generated from the partial structure ($IrL_1$) including the benzo[f]quinoline skeleton. This is because the phosphorescence quantum yield of the complex having the partial structure $IrL_1$ is high as described in Patent Literature 5. On the other hand, when phosphorescence is extracted from the partial structure $IrL_2$, the number of heteroatoms in the basic skeleton of each of the ring $A_2$ and the ring B is preferably as small as possible in consideration of the chemical stability of the ligand $L_2$. This is because of the following reason: a carbon atom and a heteroatom are different from each other in electronegativity, and hence charge bias occurs in a bond between both the atoms and the decomposition of the bond by a chemical reaction is liable to occur. In addition, the molecular weight of the basic skeleton of each of the ring $A_2$ and the ring B is preferably as small as possible in consideration of the sublimability of the iridium complex represented by the general formula [1]. Therefore, in consideration of the number of heteroatoms in the basic skeleton of each of the ring $A_2$ and the ring B, and the molecular weight of the basic skeleton, a preferred aspect of the partial structure $IrL_2$ is such a structure that the ring $A_2$ is a benzene ring and the ring B is a pyridine ring, specifically, the partial structure represented by the general formula [5].

Next, the ligand $L_3$ is described. The ligand $L_3$ is not particularly limited as long as the ligand forms a stable complex with trivalent iridium and does not largely reduce the emission quantum yield. The ligand is preferably a ligand that is formed of a skeleton having a smaller molecular weight than those of the luminous ligands ($L_1$ and $L_2$), and that improves the sublimability of the complex. The ligand $L_3$ that satisfies the requirements is preferably $\beta$-diketonate, more preferably a ligand constituting the partial structure represented by the general formula [6].

Next, the sublimability of the iridium complex is described.

In the related art, when a complex having the partial structure $IrL_1$ is obtained, a complex including one kind of luminous ligand represented by the following general formula [7], or a complex including at least one luminous ligand represented by the following general formula [8] and at least one auxiliary ligand is general.

$$Ir(L_1)_3 \qquad [7]$$

$$Ir(L_1)_2(L_3) \qquad [8]$$

($L_1$ represented in each of the formula [7] and the formula [8], and $L_3$ represented in the formula [8] are the same as $L_1$ and $L_3$ in the general formula [1], respectively.)

Here, the iridium complex represented by the general formula [8] is improved in sublimability as compared to the iridium complex represented by the general formula [7] because the auxiliary ligand ($L_3$) is used. In view of the foregoing, both the iridium complex of the present invention and the iridium complex represented by the general formula [8] were compared from the viewpoints of sublimability and heat stability.

Here, the molecular weight, sublimation temperature ($T_{sub}$), decomposition temperature ($T_d$), and difference between the decomposition temperature and the sublimation temperature ($\Delta T = T_d - T_{sub}$) of each of the iridium complex of the present invention and the iridium complex represented by the general formula [8] are shown.

TABLE 1

| | Structure | Molecular weight | Sublimation temperature $T_{sub}/°C$ | Decomposition temperature $T_d/°C$ | $\Delta T/°C$ |
|---|---|---|---|---|---|
| Exemplified Compound Ir-113 | 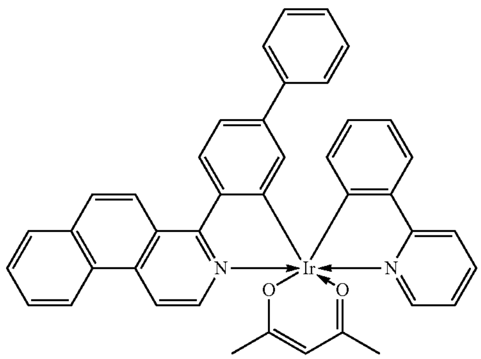 | 775.9 | 300 | 355 | 55 |
| Complex 2 | 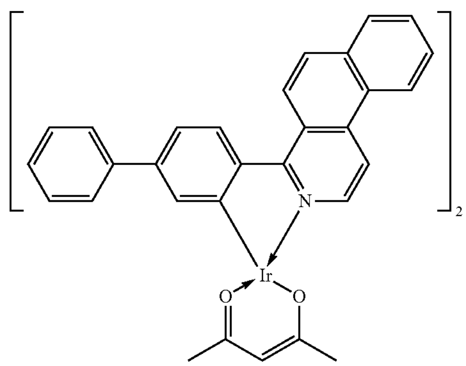 | 952.1 | 370 | 400 | 30 |
| Exemplified Compound Ir-106 | 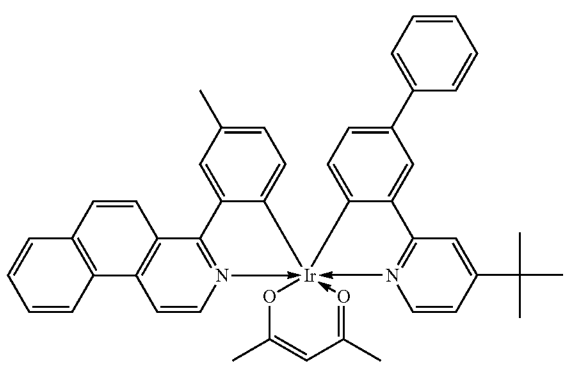 | 846.1 | 290 | 375 | 85 |
| Complex 3 | 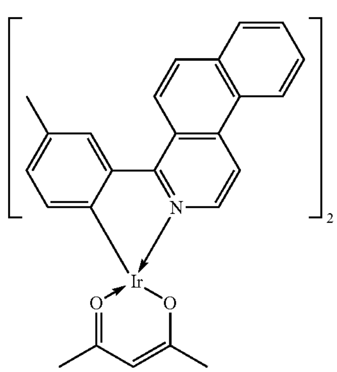 | 828.0 | 345 | 375 | 30 |

Here, the $T_d$ is an indicator of the heat stability of the complex itself and the $\Delta T$ ($=T_d-T_{sub}$) is an indicator of heat stability in a step involving sublimation. Therefore, the $\Delta T$ becomes more important than the $T_d$ is upon sublimation purification or vacuum deposition. This is because when the $\Delta T$ is small, thermal decomposition gradually progresses even at a temperature equal to or lower than the $T_d$ upon sublimation to produce impurities. In addition, a small $\Delta T$ is industrially disadvantageous because the range of regulation of a sublimation rate is small, i.e., step tolerance is small.

Table 1 shows that the $T_{sub}$ of Exemplified Compound Ir-113 is lower than that of Complex 2 by 70° C. and is hence largely improved in sublimability.

A first possible factor for the foregoing is a reduction in crystallinity. While Complex 2 has a $C_2$ symmetrical structure, Exemplified Compound Ir-113 is asymmetrical. Therefore, in Exemplified Compound Ir-113, π-π stacking caused by the approach of $L_1$'s in complex molecules adjacent to each other hardly occurs as compared to Complex 2.

A second possible factor therefor is the fact that the molecular weight of Exemplified Compound Ir-113 is smaller than the molecular weight of Complex 2 by 176.2. The molecular weight of Exemplified Compound Ir-113 was smaller than that of Complex 2, and hence its $T_d$ was lower than that of Complex 2 by 45° C., while its $\Delta T$ ($T_d-T_{sub}$) was larger than that of Complex 2 by 25° C. In other words, it can be said that Exemplified Compound Ir-113 is improved not only in sublimability but also in heat stability at the time of a sublimation operation.

On the other hand, the $T_{sub}$ of Exemplified Compound Ir-106 is lower than that of Complex 3 by 55° C. despite the fact that its molecular weight is larger than that of Complex 3 by 18.1. The foregoing means that an intermolecular interaction between complex molecules significantly reduced. A possible factor for the foregoing is the fact that the ligand $L_2$, i.e., a phenyl group and tert-butyl group introduced into 2-phenylpyridine as well as the asymmetry of the complex itself inhibit the intermolecular interaction between the complex molecules.

In addition, the $\Delta T$ ($T_d-T_{sub}$) of Exemplified Compound Ir-106 was larger than that of Complex 3 by 55° C. because values for the $T_d$'s of both the materials were the same. Accordingly, Exemplified Compound Ir-106 is a ligand largely improved in heat stability.

As described above, the iridium complex of the present invention is reduced in crystallinity and improved in sublimability because the complex has three kinds of ligands structurally different from one another to become an asymmetrical complex. Further, the degree of freedom in molecular design of the complex can be increased as long as the complex has a predetermined partial structure. Specifically, the complex can be additionally improved in sublimability and heat stability as compared to a conventional iridium complex by reducing its molecular weight or introducing a substituent.

(4-2) Action Exhibited by Host

The iridium complex represented by the general formula [1] to be incorporated as the guest in the organic light-emitting element of the present invention has a phenylbenzo[f]isoquinoline skeleton. The conjugate plane of the π orbital of the phenylbenzo[f]isoquinoline skeleton is extended as compared to a phenylquinoline skeleton or phenylisoquinoline skeleton as the basic skeleton of a ligand of a conventional and typical red light-emitting material because a benzene ring condenses to quinoline. As a result, an interaction with a material (especially the host) near the light-emitting material is liable to occur, with the result that the light-emitting material captures the charge of the host to form a radical state or form an exciplex with the host. Thus, the light-emitting efficiency or durability of the organic light-emitting element itself may be liable to reduce.

Therefore, in order that a situation where the light-emitting material is excessively brought into a radical state may be avoided, a difference in energy level between the HOMO and LUMO of the host is preferably made smaller than that between the HOMO and LUMO of the light-emitting material. That is, a host having a small $\Delta S-T$ (difference between the lowest singlet energy level and the lowest triplet energy level), and a small band gap is preferred.

In addition, the emission peak wavelength of the iridium complex represented by the general formula [1] to be used as the guest mainly falls within the range of 580 nm to 650 nm (1.9 eV to 2.1 eV in terms of the lowest triplet energy level ($T_1$)). Therefore, the $T_1$ energy of the host needs to be made higher than that of the guest.

In general, the $\Delta S-T$ of a metal complex is small owing to an influence of a spin-orbit interaction. In view of the foregoing, the light-emitting material to be used as a constituent material for the organic light-emitting element of the present invention preferably uses the metal complex represented by the general formula [9] as the host.

(5) Specific Examples of Iridium Complex

Specific examples of the iridium complex serving as the guest are shown below.

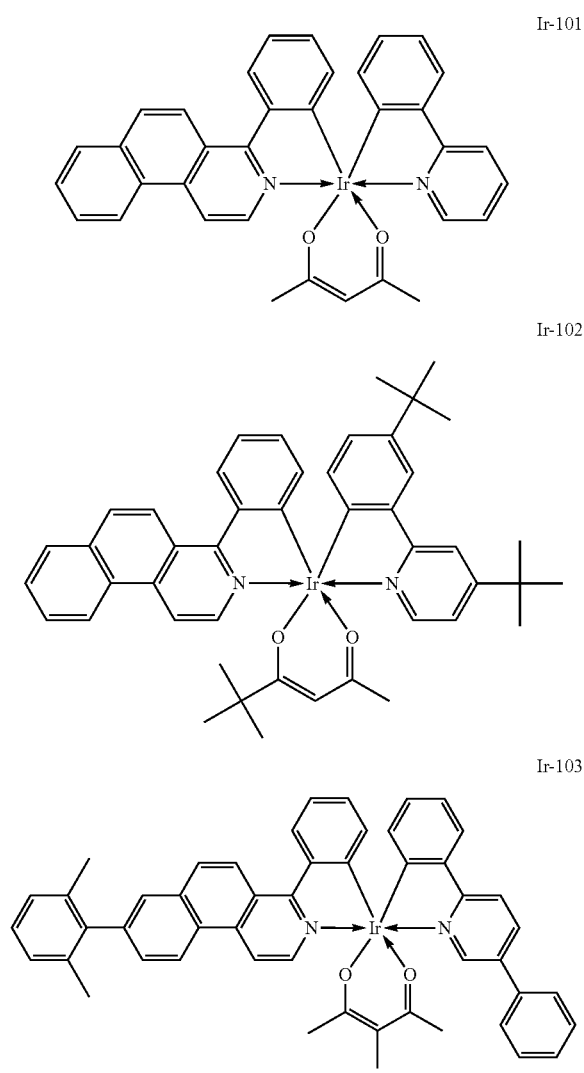

Ir-104
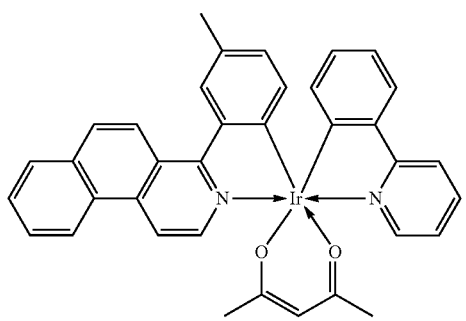
Ir-105
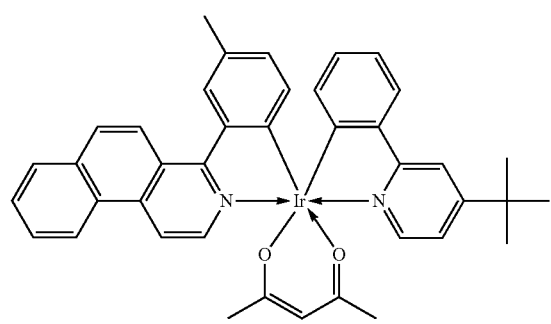
Ir-106
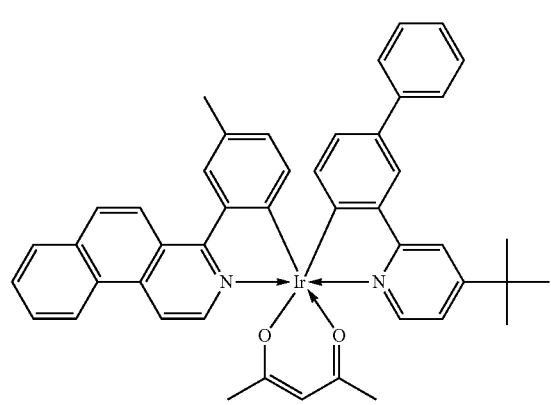
Ir-107
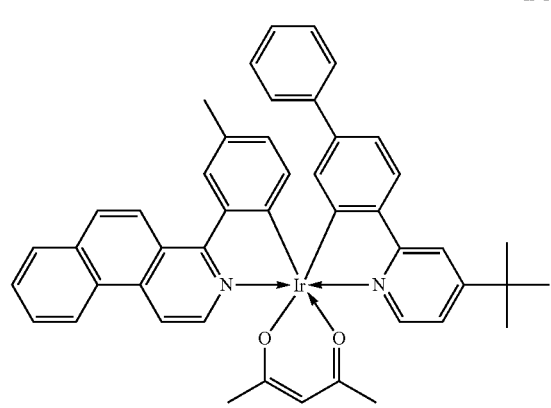
Ir-108
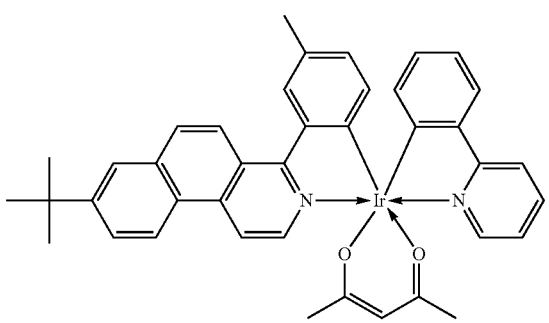
Ir-109
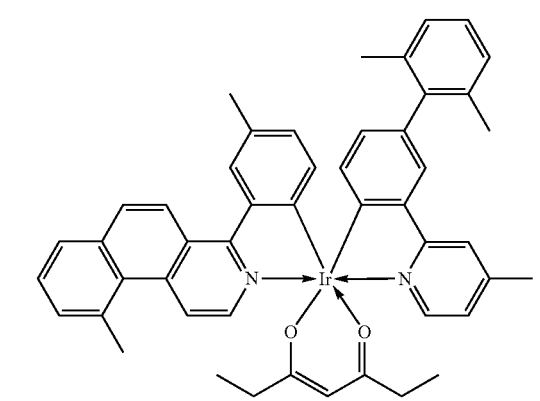
Ir-110
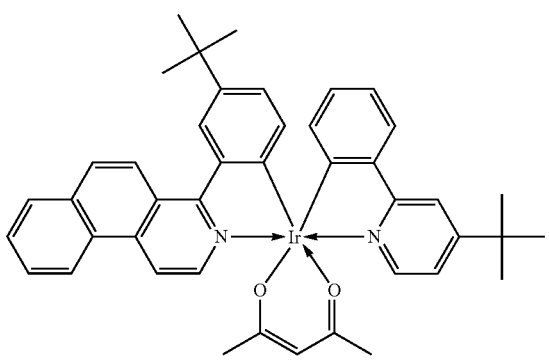
Ir-111

Ir-112
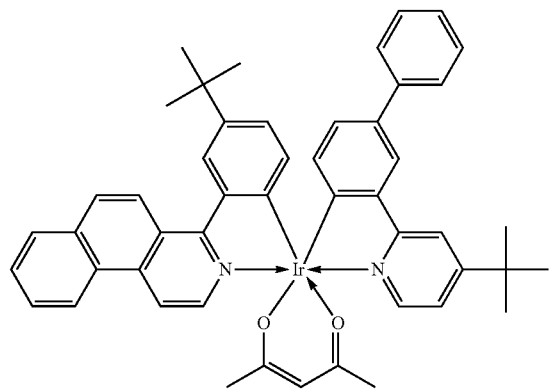
Ir-113
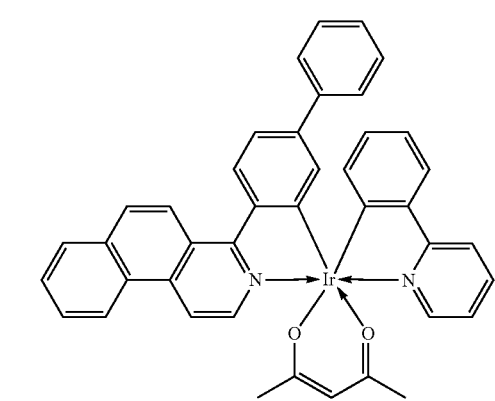
Ir-114
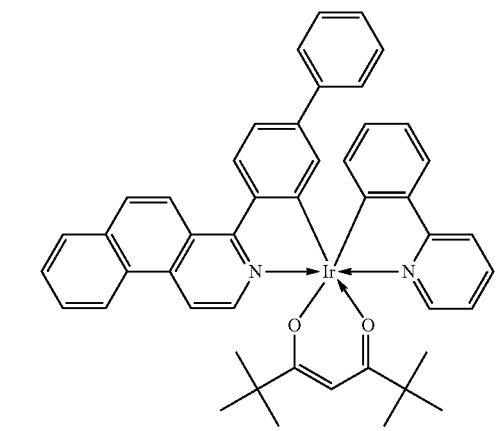
Ir-115
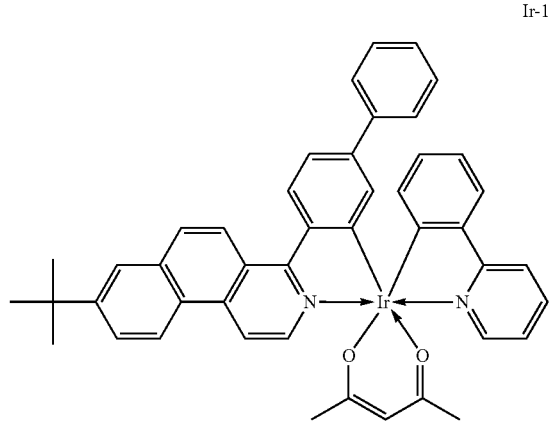
Ir-116
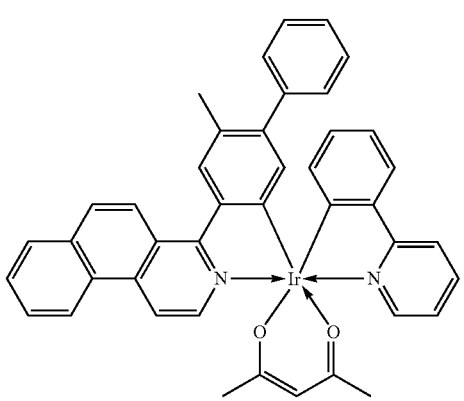
Ir-117
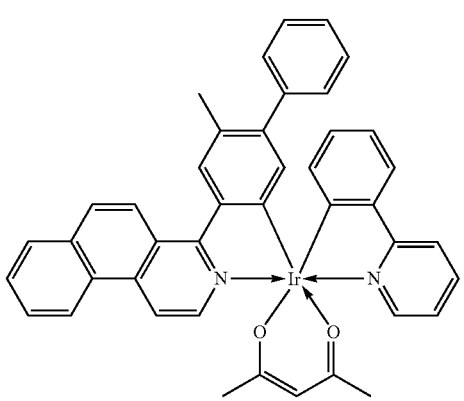
Ir-118
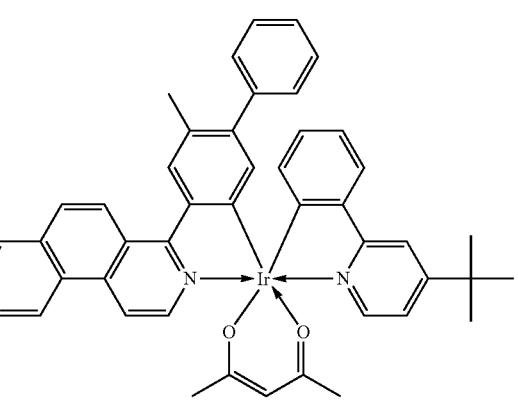
Ir-119
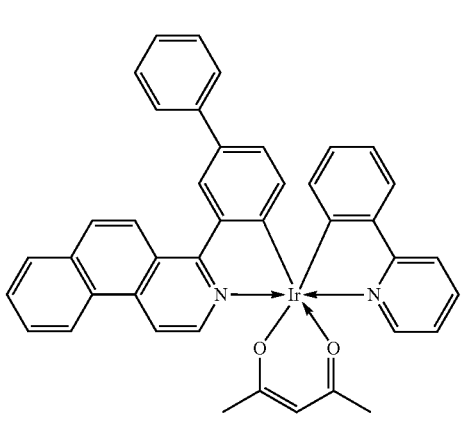

Ir-120
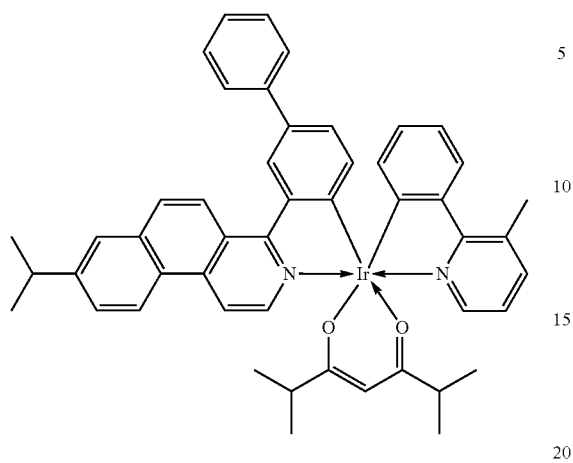
Ir-121
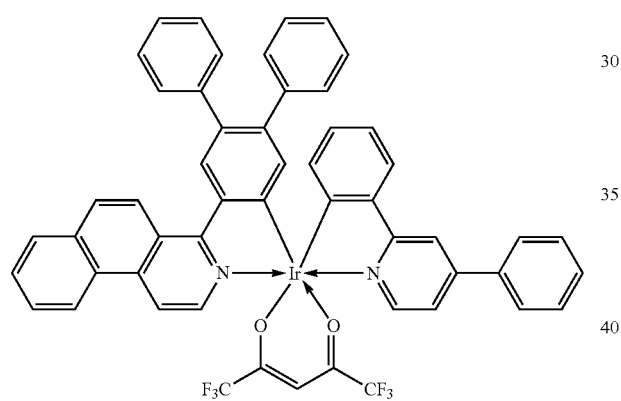
Ir-122
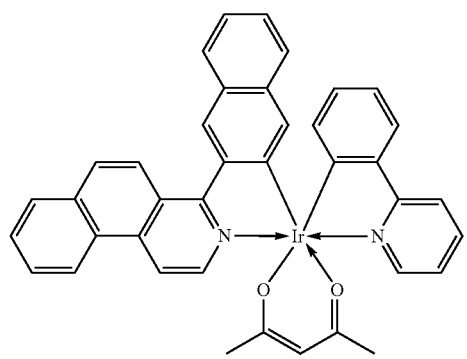
Ir-123
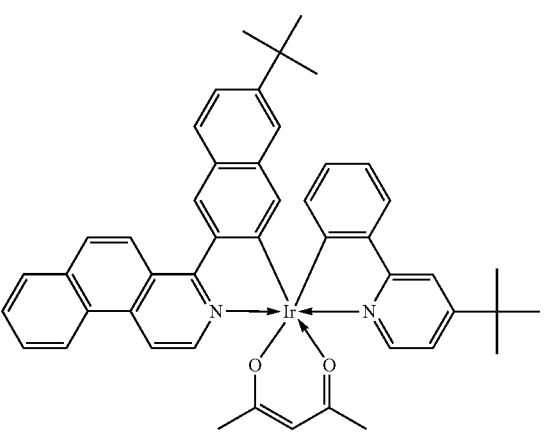
Ir-124
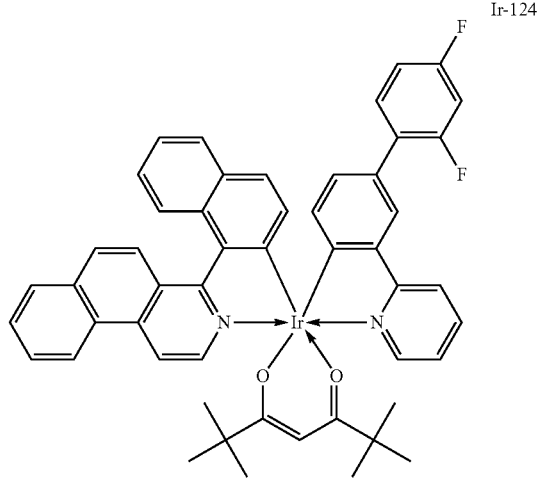
Ir-125
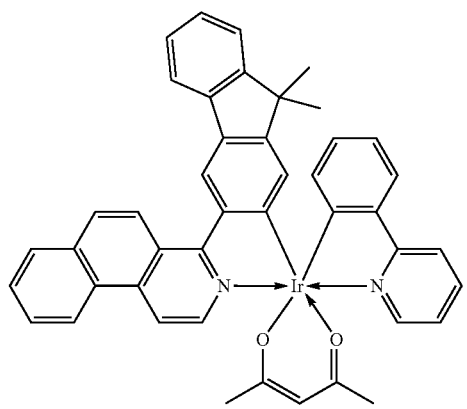

Ir-126
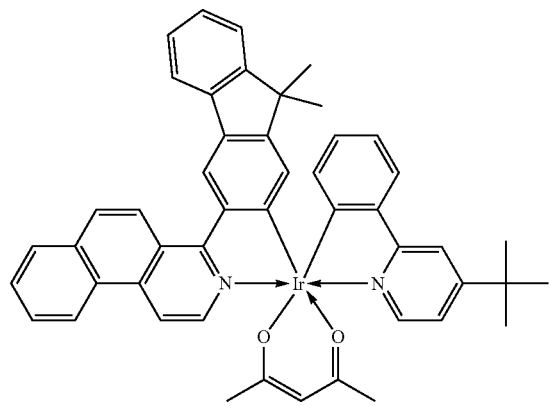
Ir-127
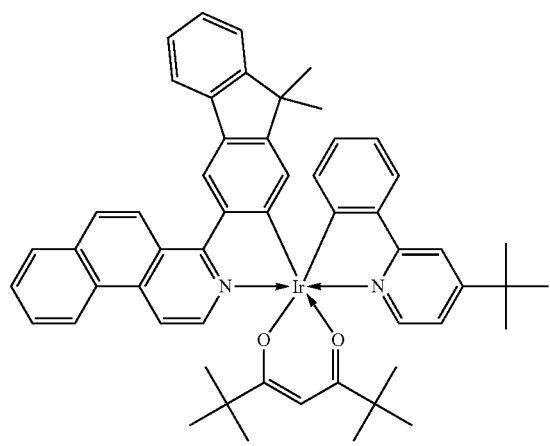
Ir-128
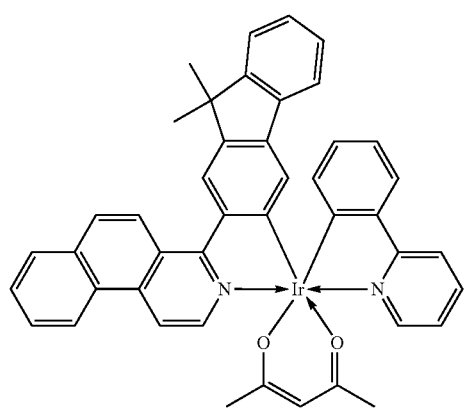
Ir-129
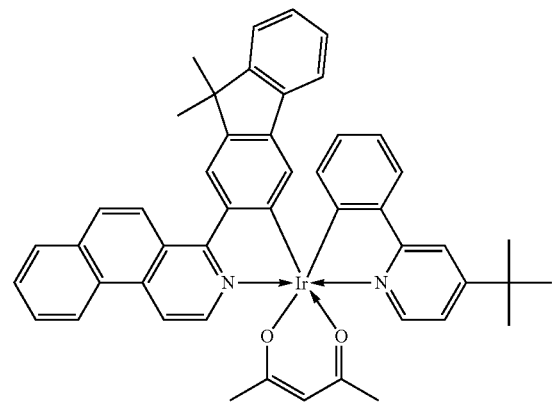
Ir-130
Ir-131

Ir-132
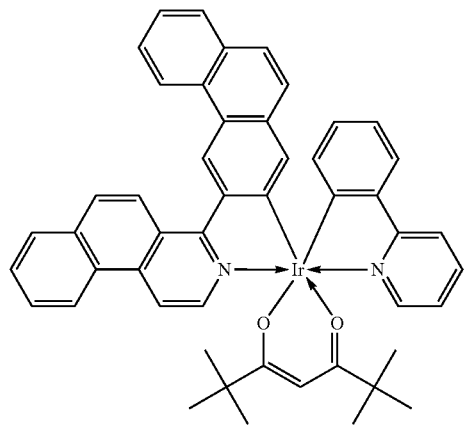
Ir-133
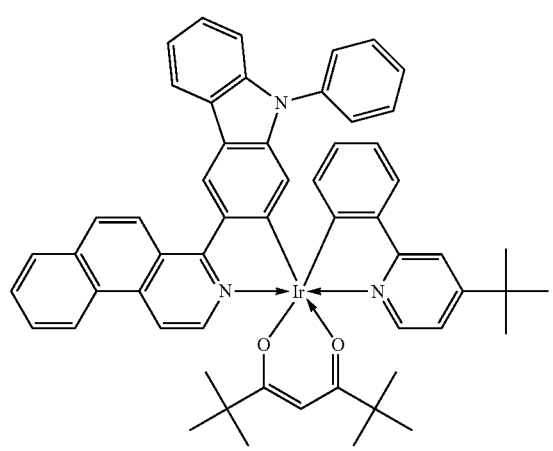
Ir-134
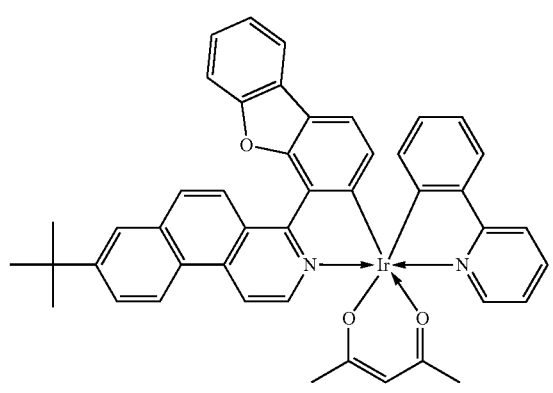
Ir-135
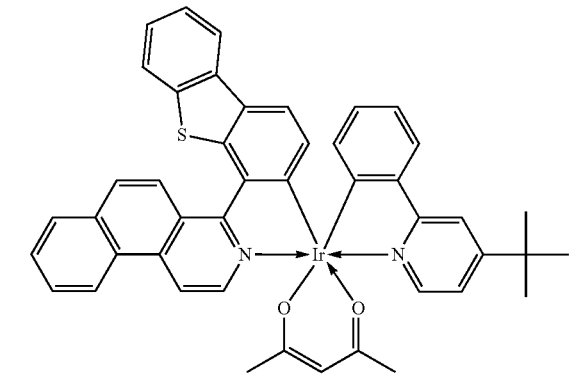
Ir-136
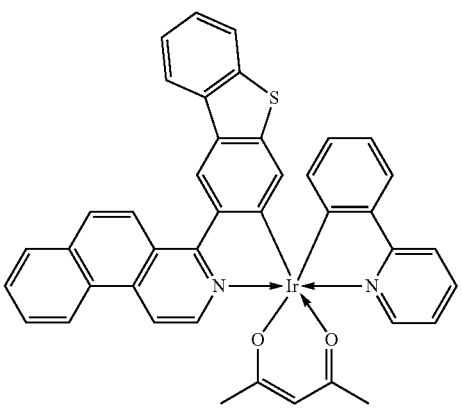
Ir-201
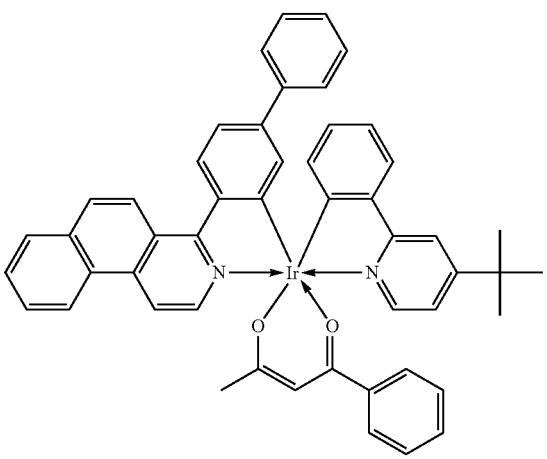
Ir-202

Ir-203
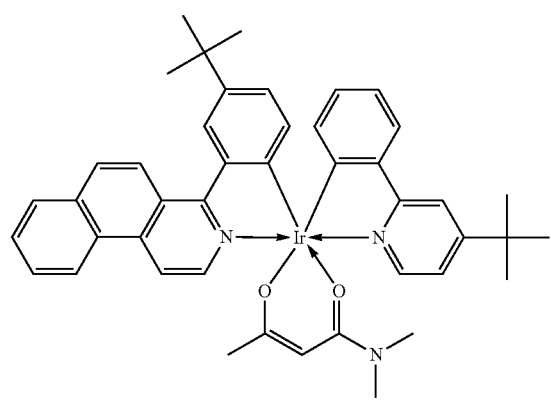
Ir-204
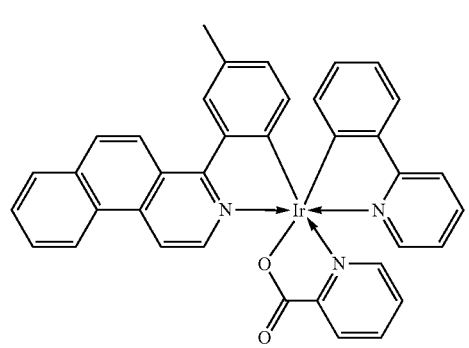
Ir-205
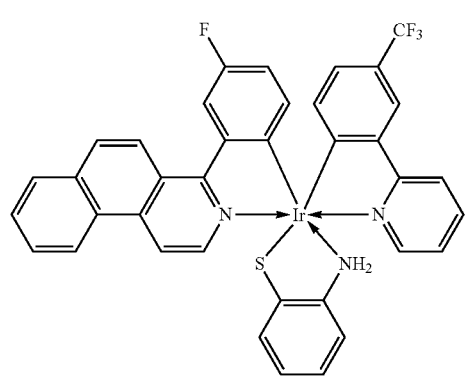
Ir-206
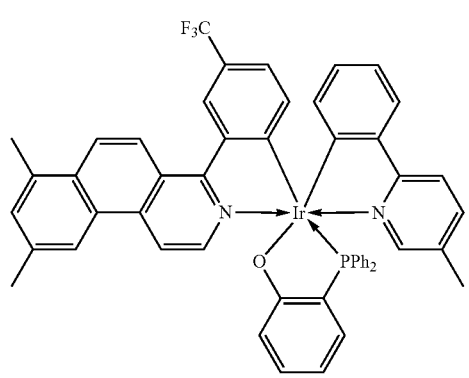
Ir-301
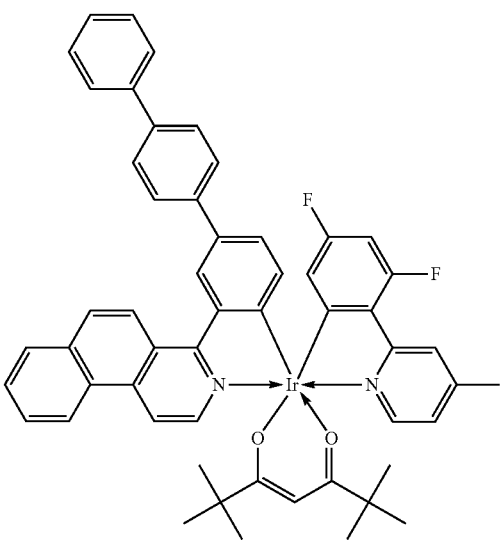
Ir-302
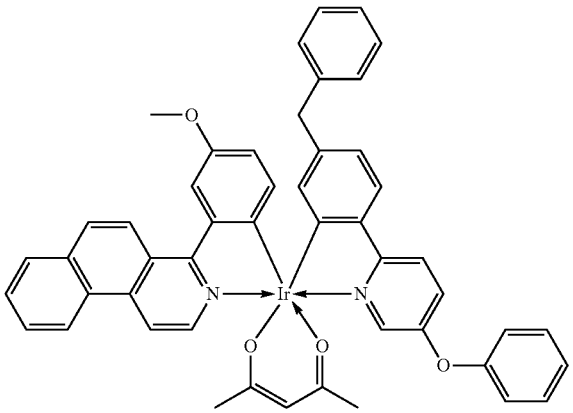
Ir-303
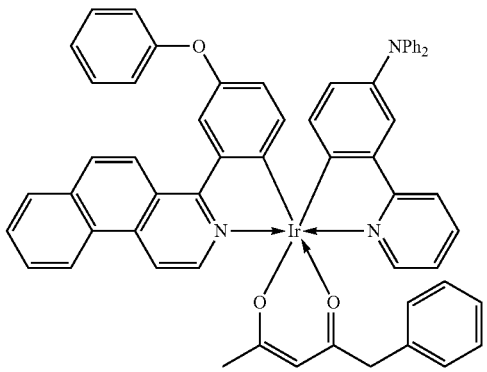

Ir-304
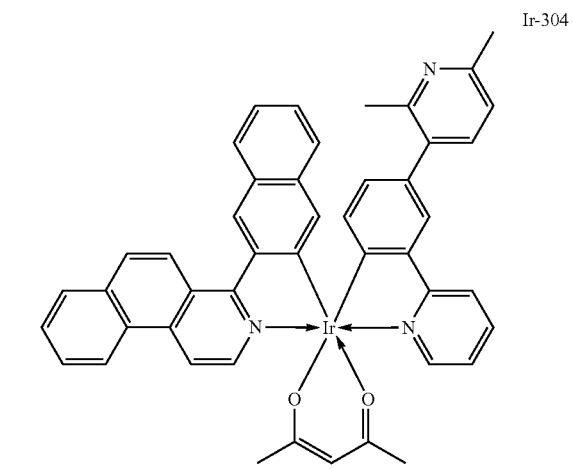
Ir-305
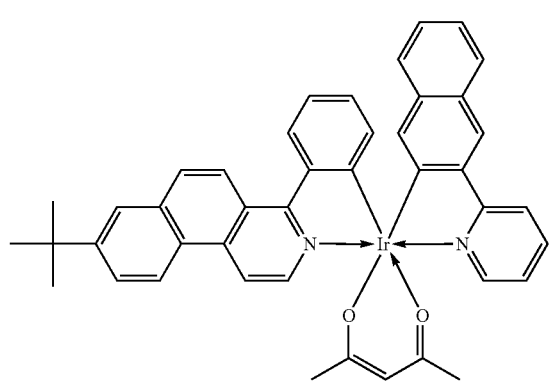
Ir-306
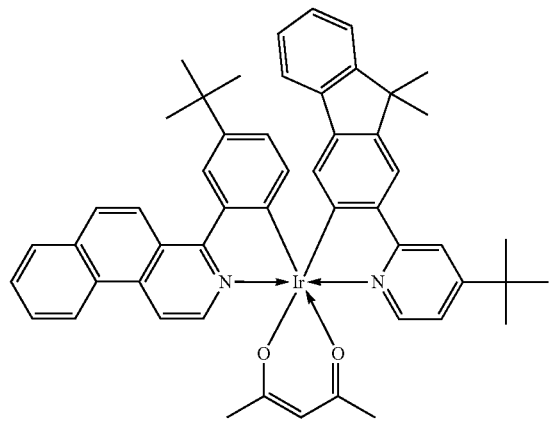
Ir-307
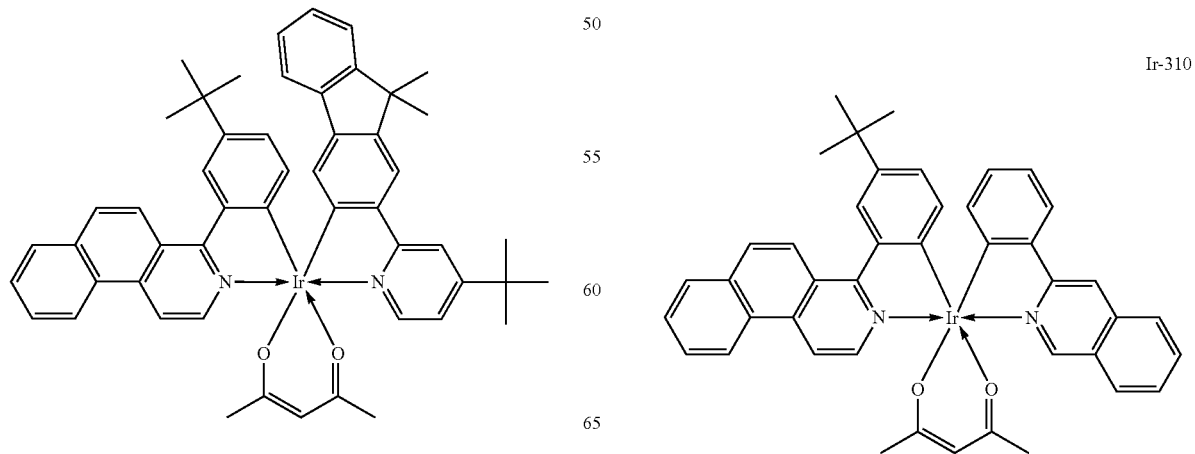
Ir-308
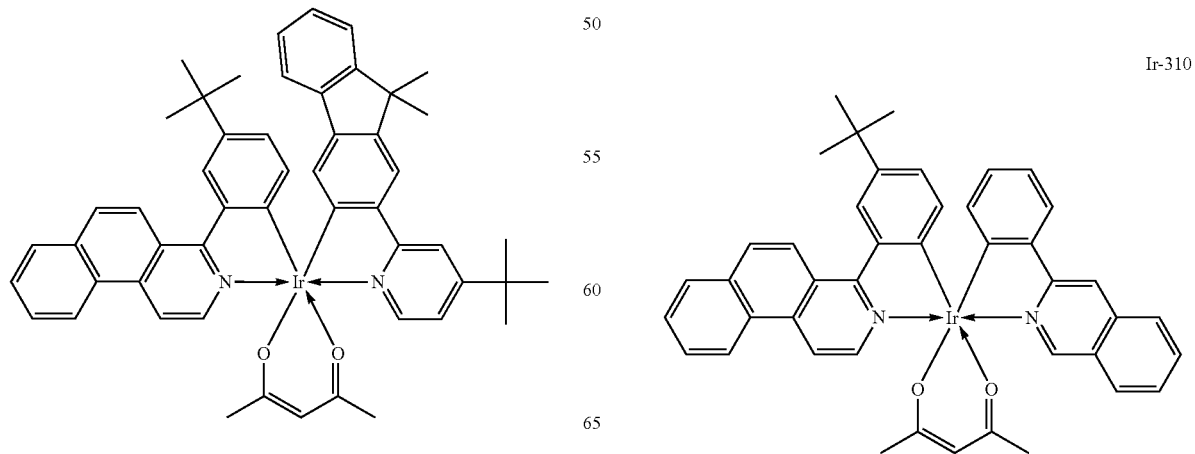
Ir-309
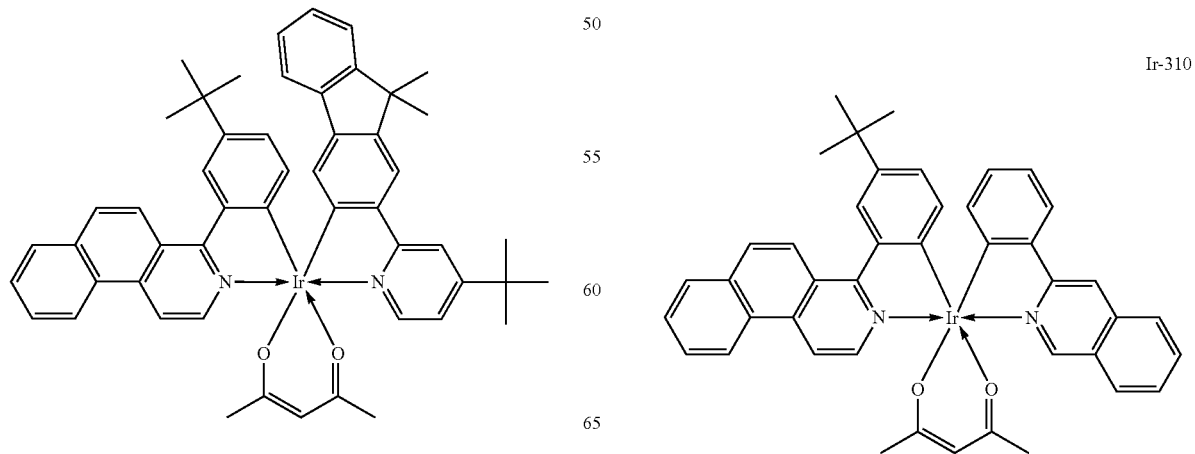
Ir-310
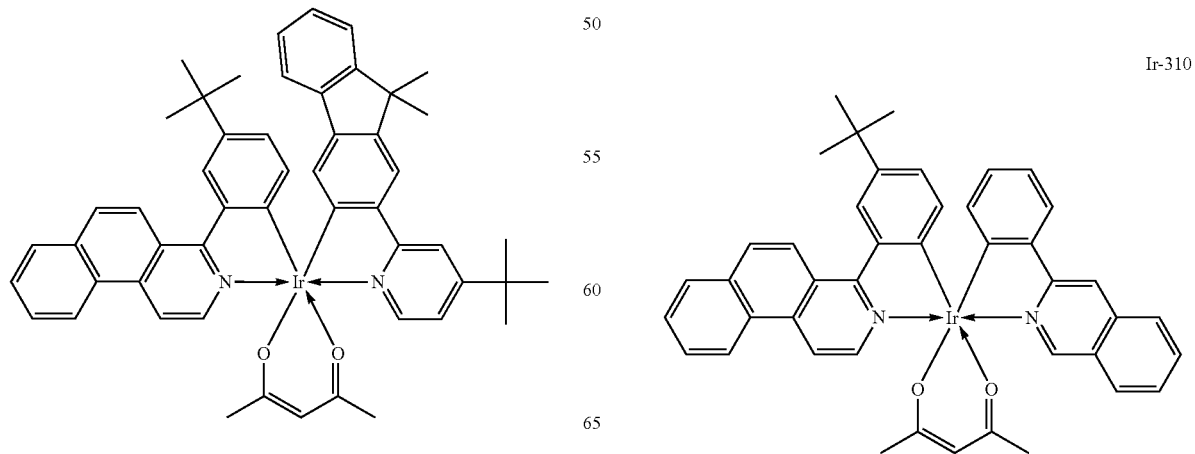

Ir-311
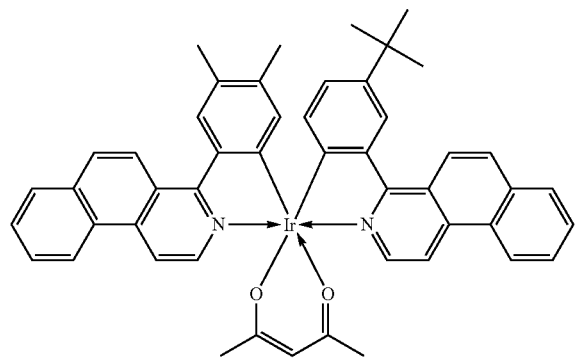
Ir-312
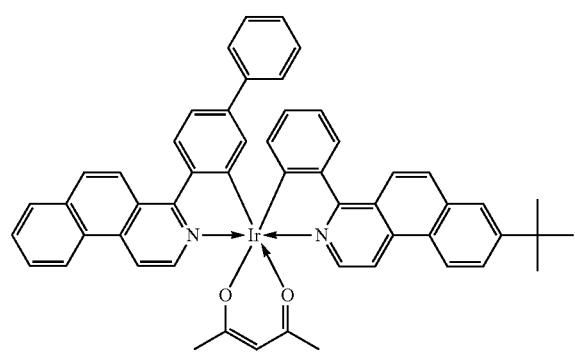
Ir-401
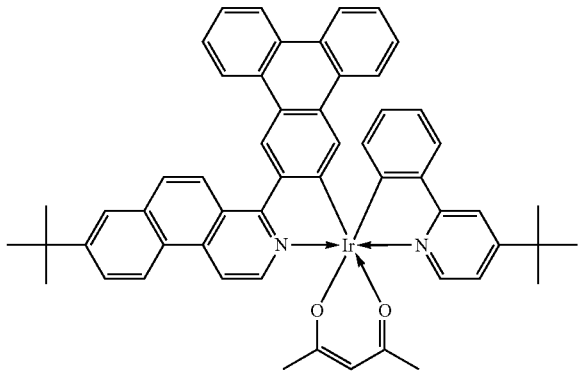
Ir-402
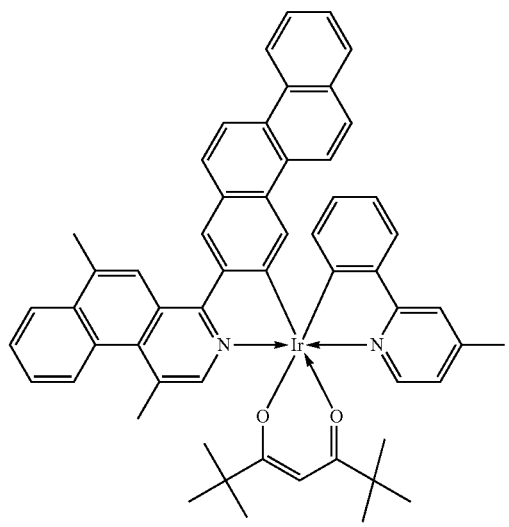
Ir-403
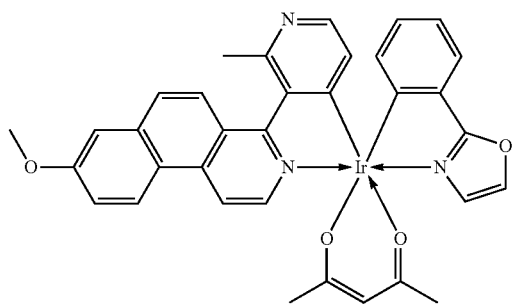
Ir-404
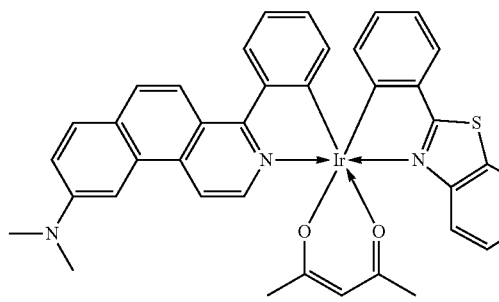
Ir-405
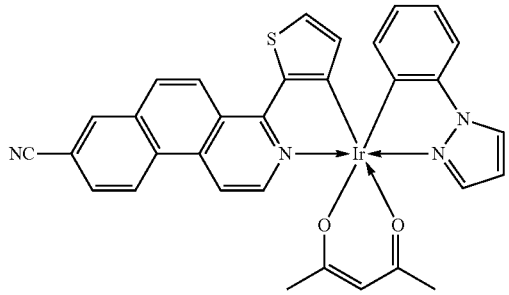

Ir-406

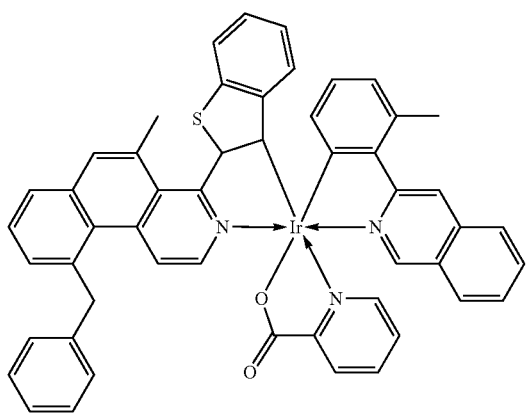

Of the exemplified iridium complexes, Ir-101 to Ir-136 each have a structure given below.

The partial structure including the ligand $L_1$ is the structure represented by the general formula [4]. The partial structure including the ligand $L_2$ is the structure represented by the general formula [5], and $R_{13}$ to $R_{20}$ in the formula [5] each represent a hydrogen atom, an alkyl group having 1 or more and 4 or less carbon atoms, or a phenyl group.

The partial structure including the ligand $L_3$ is the structure represented by the general formula [6], and $R_{21}$ to $R_{23}$ in the formula [6] each represent a hydrogen atom or an alkyl group having 1 or more and 4 or less carbon atoms.

Therefore, Ir-101 to Ir-136 are each particularly excellent in sublimability because preferred aspects of the three kinds of ligands to be incorporated into the iridium complex of the present invention are combined. In addition, the complexes each generate phosphorescence whose color ranges from an orange color to a red color resulting from the partial structure $IrL_1$.

Of the exemplified iridium complexes, Ir-201 to Ir-206 each use β-diketonate or any other bidentate ligand having a specific substituent as the ligand $L_3$. The phosphorescence characteristics of any such iridium complex such as an emission peak wavelength and the waveform of an emission spectrum can be appropriately regulated by changing $L_3$ as the auxiliary ligand.

Of the exemplified iridium complexes, Ir-301 to 312 are each such that the ligand $L_2$ is the ligand represented by the general formula [3] or [5]. In the present invention, the ligand $L_2$ can be selected from a wider range of alternatives as long as its basic structure is represented by the general formula [3]. Here, the (energy level of the) HOMO or LUMO of any such iridium complex can be changed, or phosphorescence based mainly on the partial structure $IrL_2$ can be generated by appropriately selecting the ligand $L_2$.

Of the exemplified iridium complexes, Ir-401 to Ir-406 each have a structure given below.

The partial structure including the ligand $L_1$ is the structure represented by the general formula [2].

The partial structure including the ligand $L_2$ is the structure represented by the general formula [3].

In addition, not only phosphorescence whose color ranges from an orange color to a red color but also phosphorescence having a longer wavelength can be generated by $L_1$ represented in each of Ir-401 to Ir-406. In addition, a complex having various physical properties can be designed by appropriately combining $L_1$ and $L_2$ represented in each of Ir-401 to Ir-406.

(6) Specific Examples of Metal Complex

Specific structural formulae of the metal complex compound to be used as the host are exemplified below.

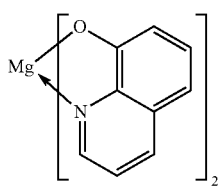

H101

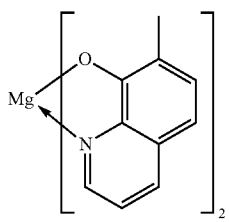

H102

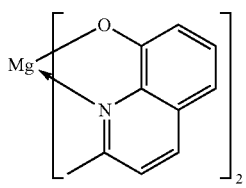

H103

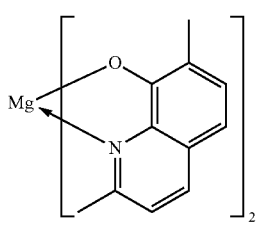

H104

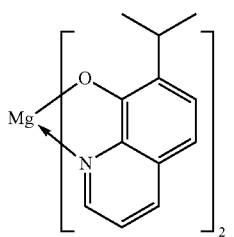

H105

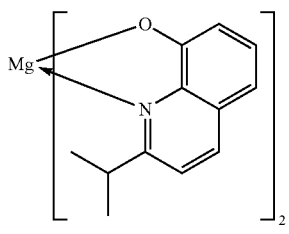

H106

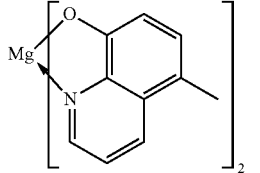

H107

-continued
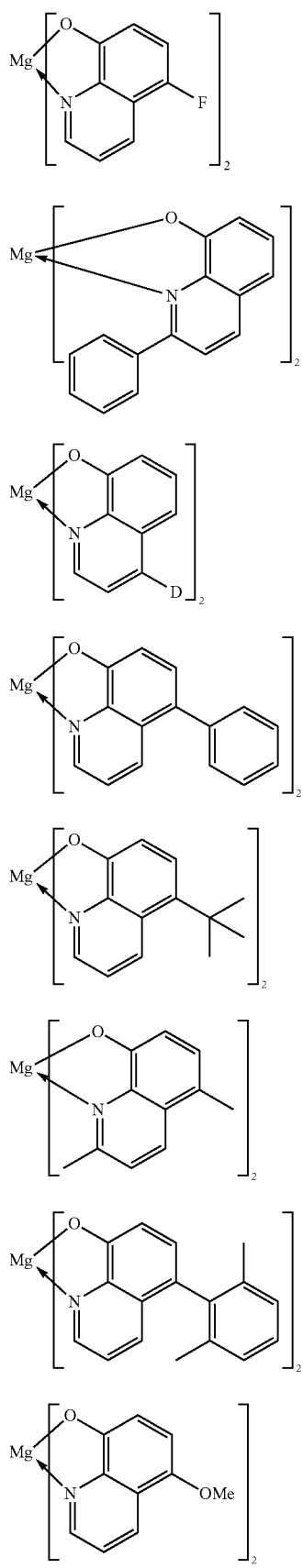
H108
H109
H110
H111
H112
H113
H114
H115
-continued
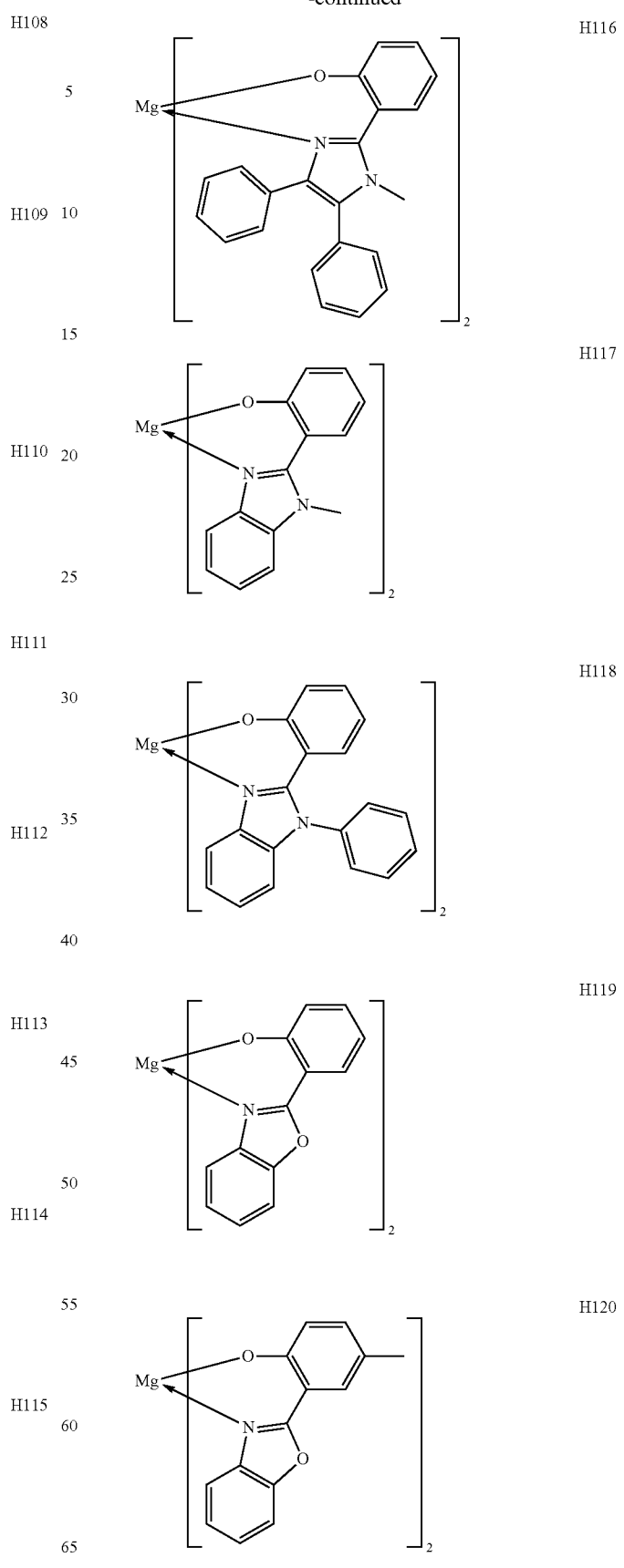
H116
H117
H118
H119
H120

H121
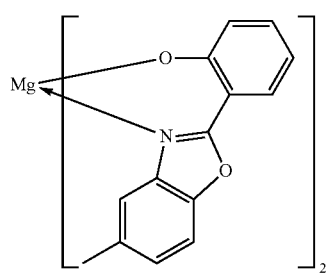
H122
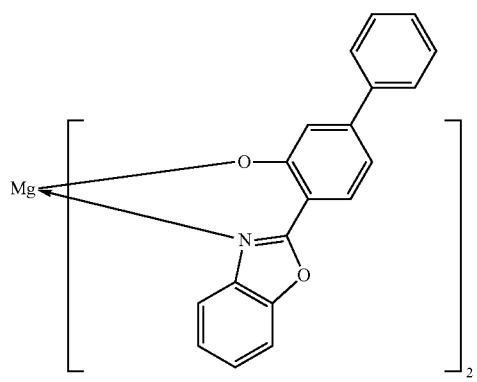
H123
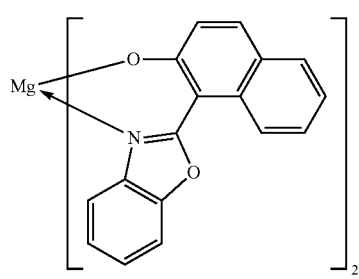
H124
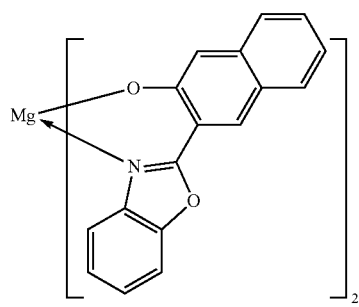
H125
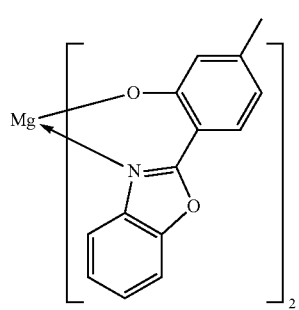
H126
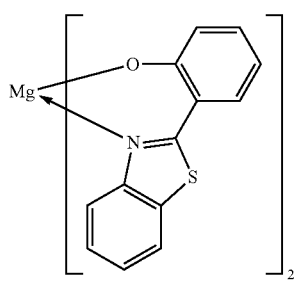
H127
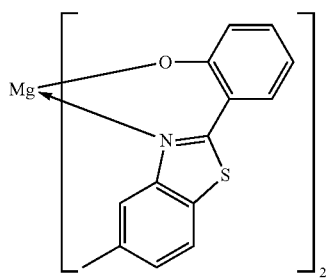
H128
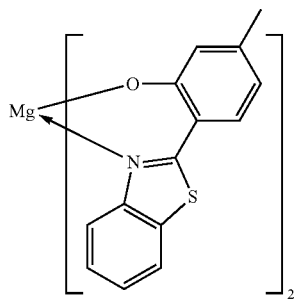
H129
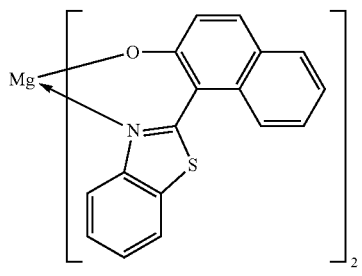
H130
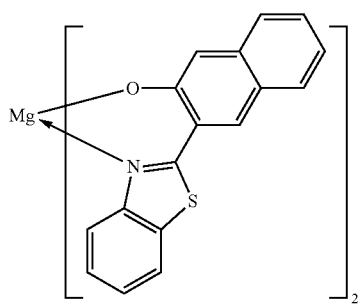

H131 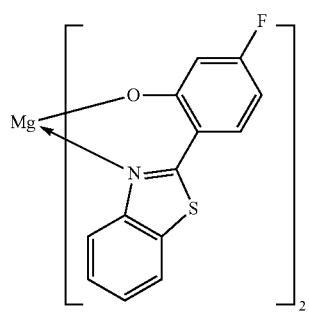
H132 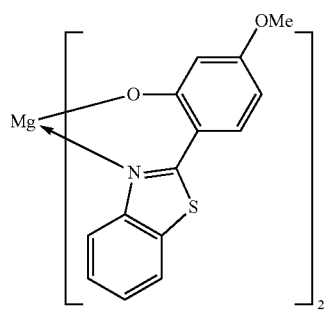
H133 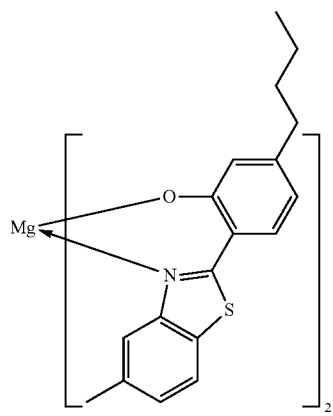
H134 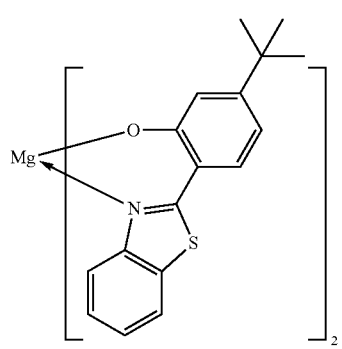
H135 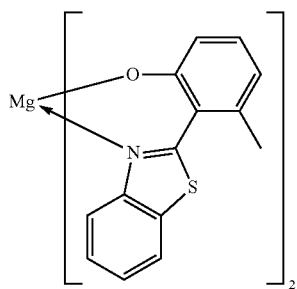
H136 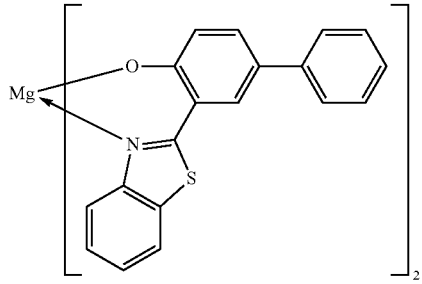
H201 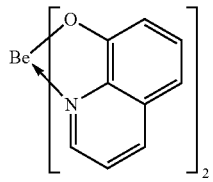
H202 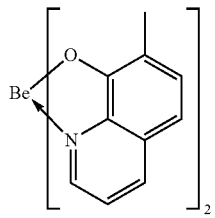
H203 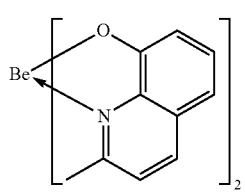
H204 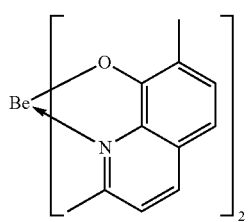

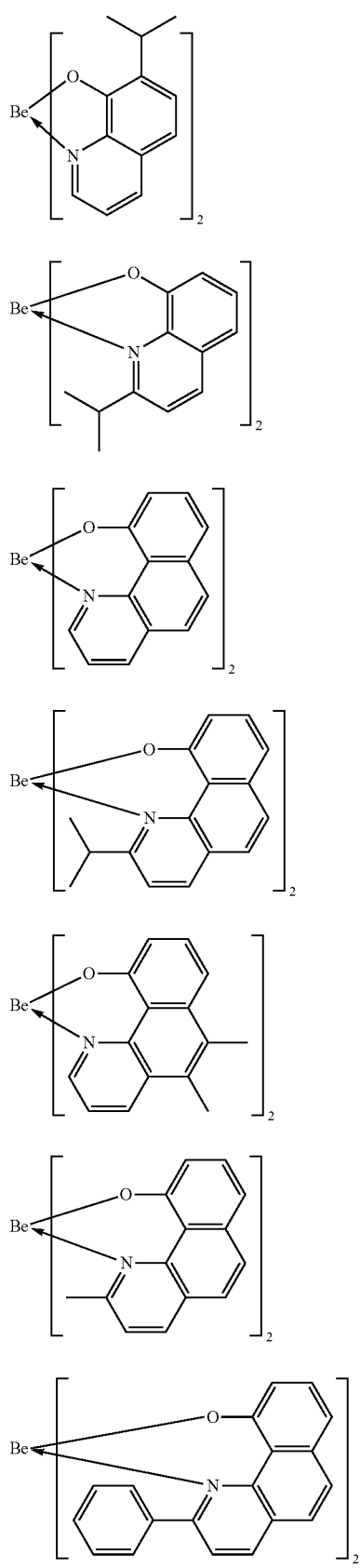
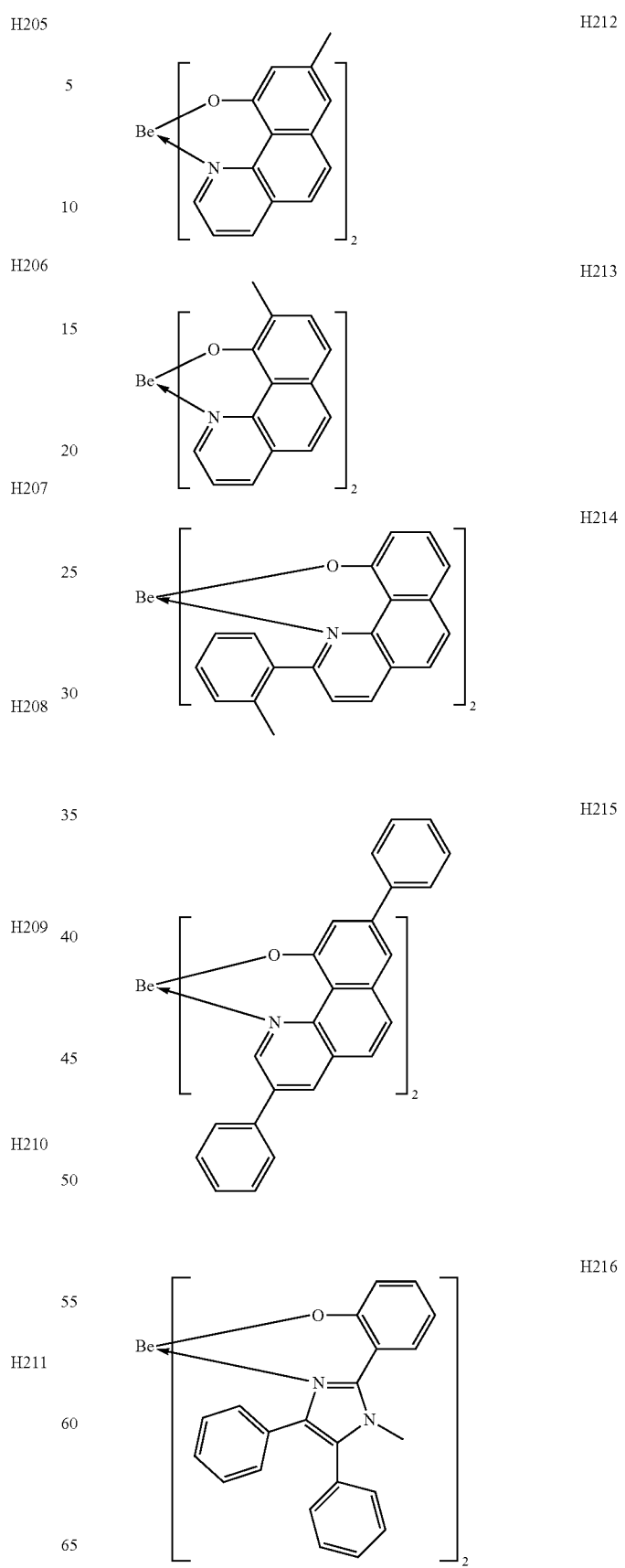

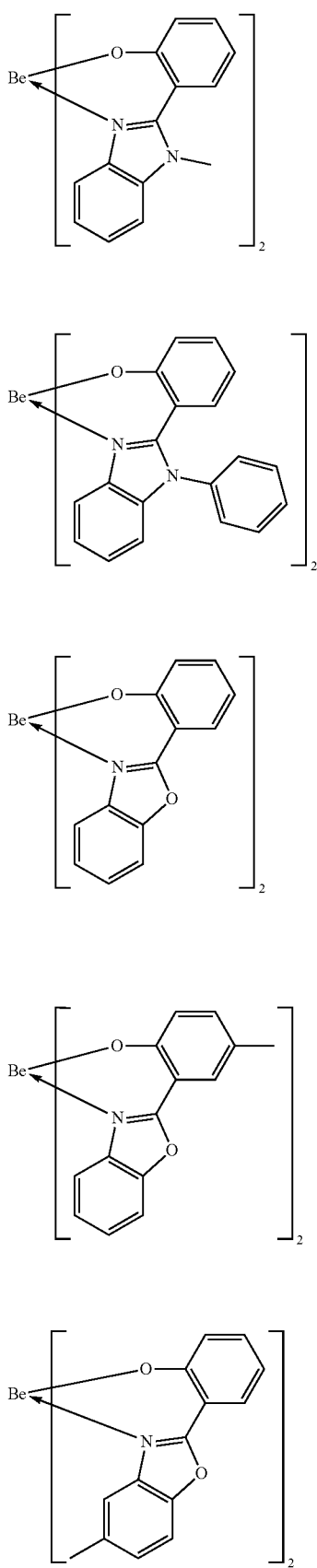
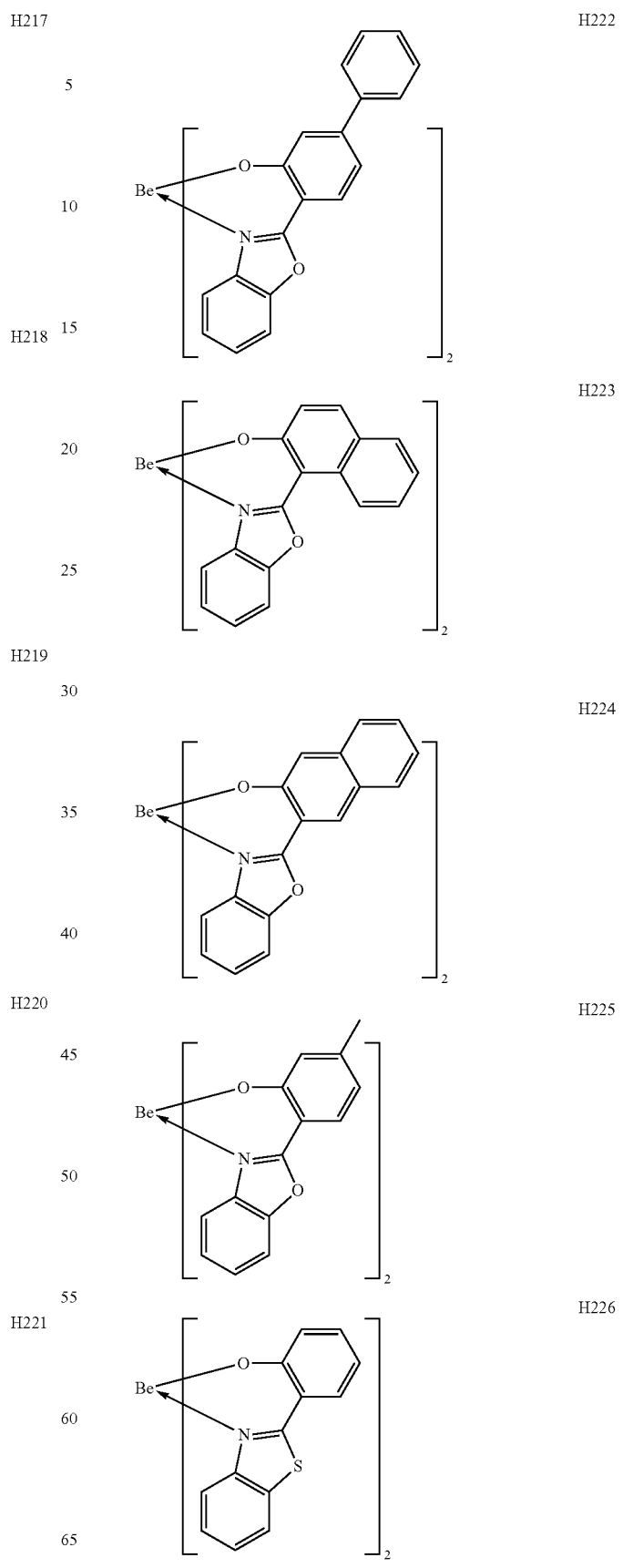

H227 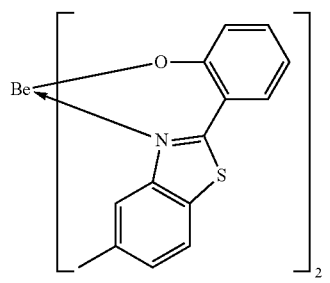
H228 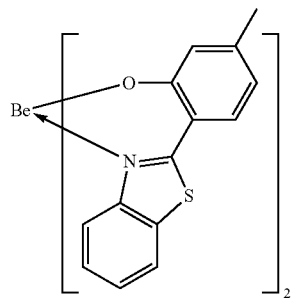
H229 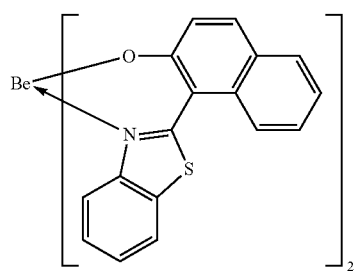
H230 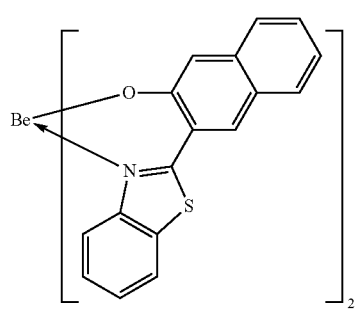
H231 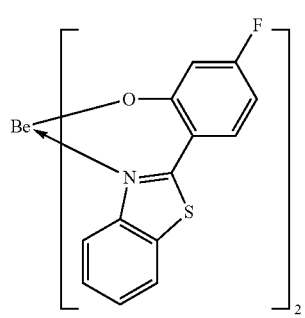
H232 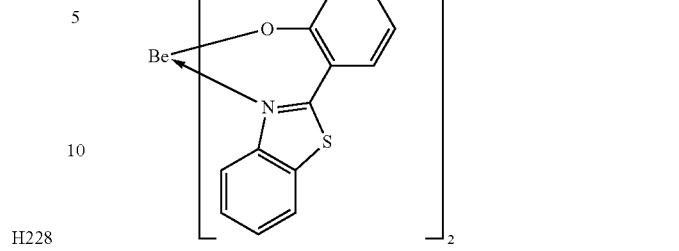
H233 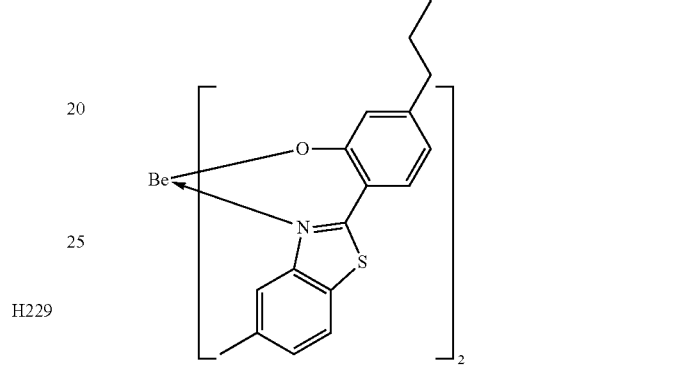
H234 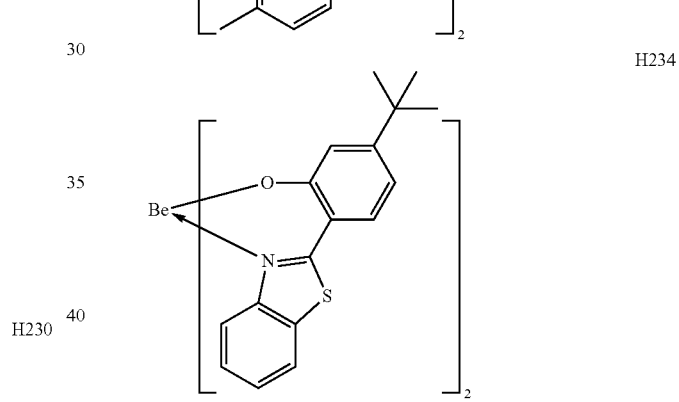
H235 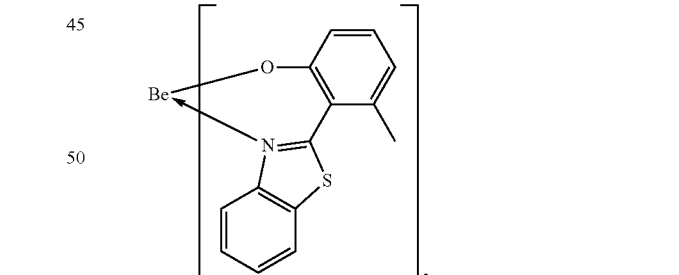
H236 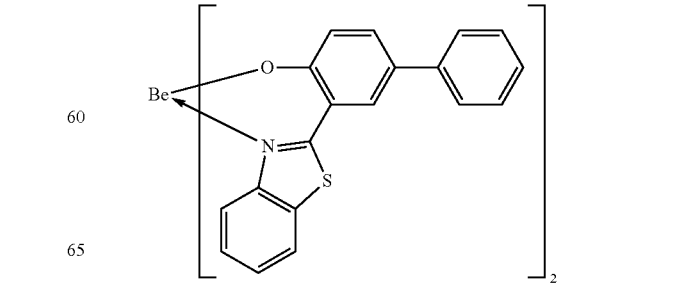

H301
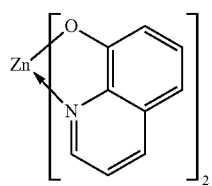
H302
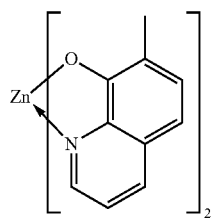
H303
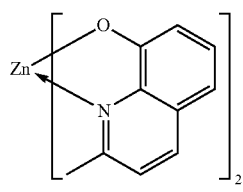
H304
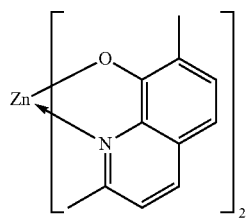
H305
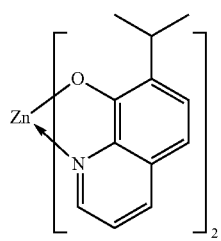
H306
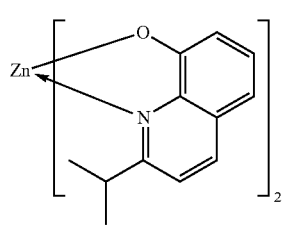
H307
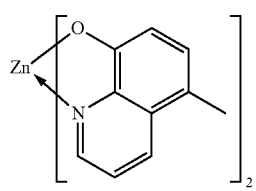
H308
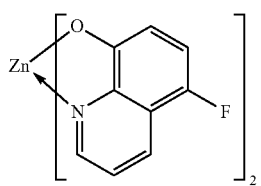
H309
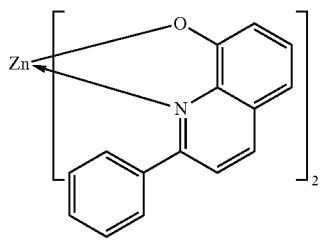
H310
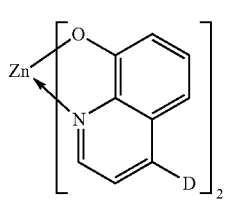
H311
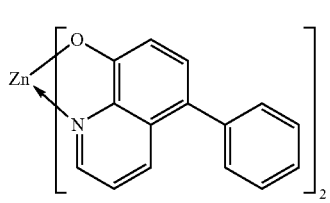
H312
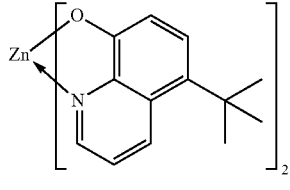
H313
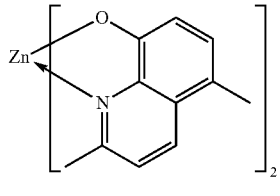
H314
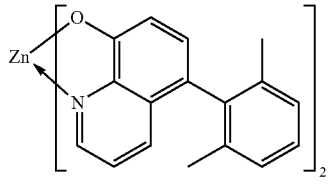
H315
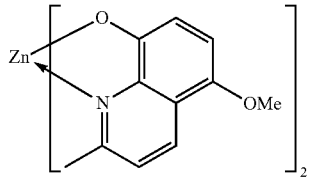

H316
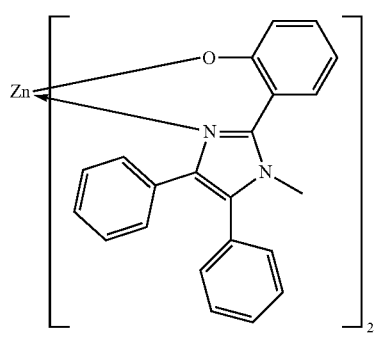
H317
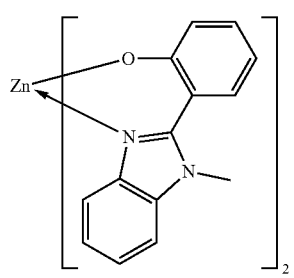
H318
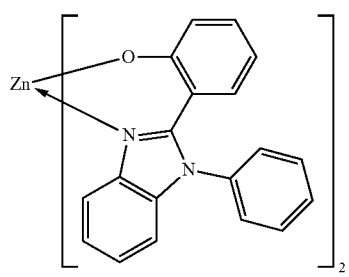
H319
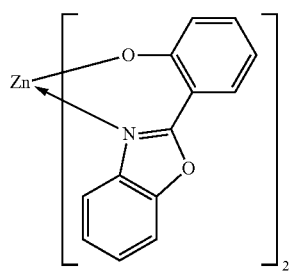
H320
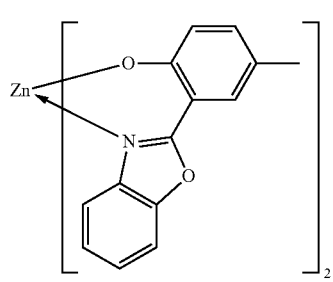
H321
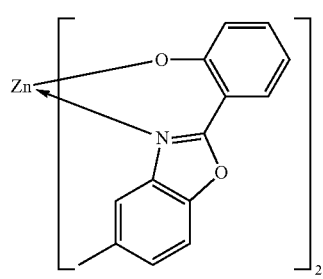
H322
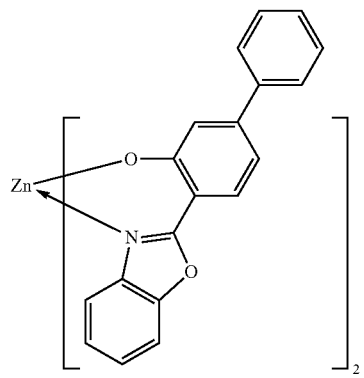
H323
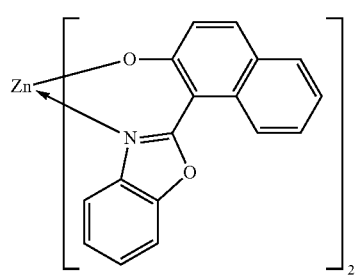
H324
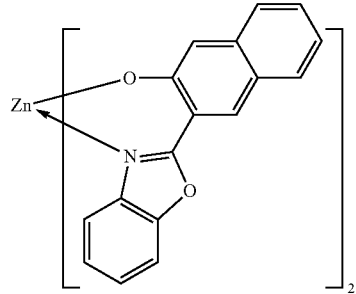
H325
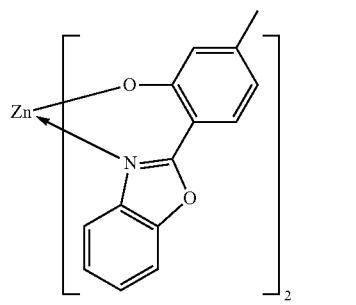

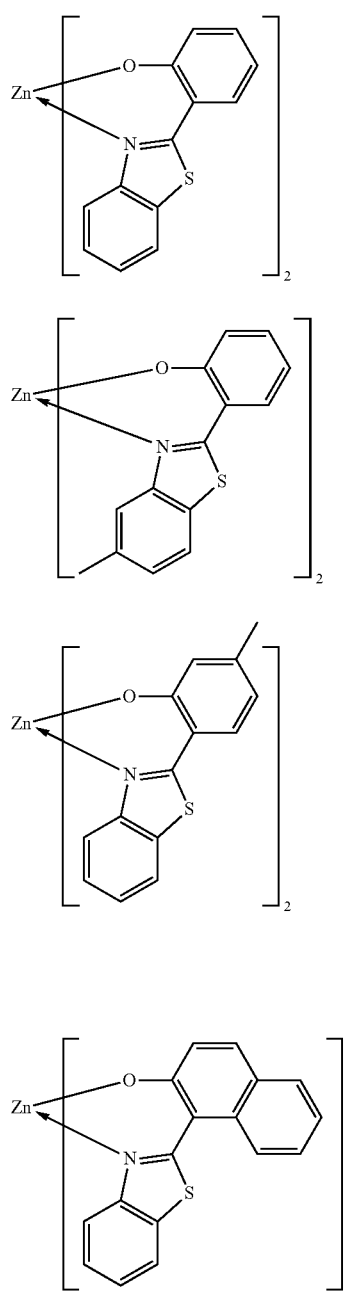
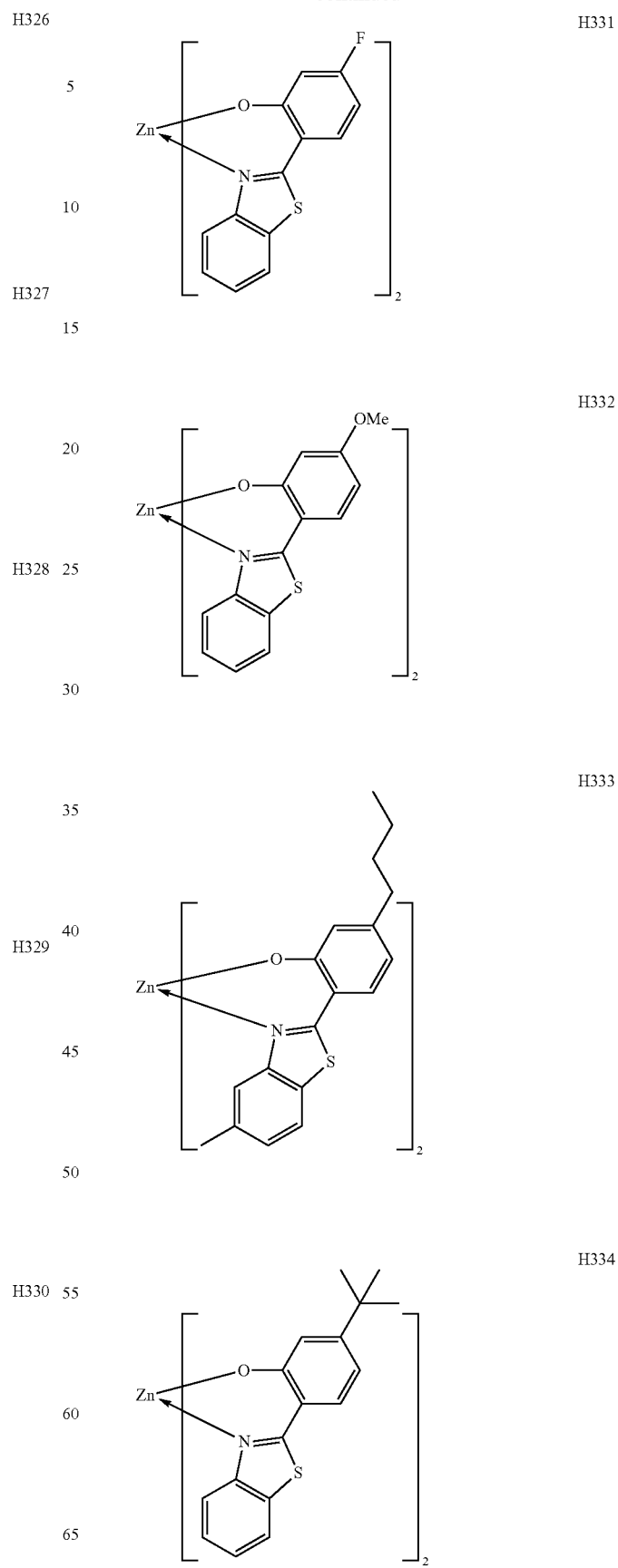

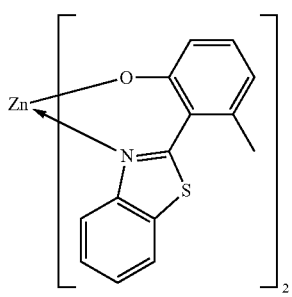

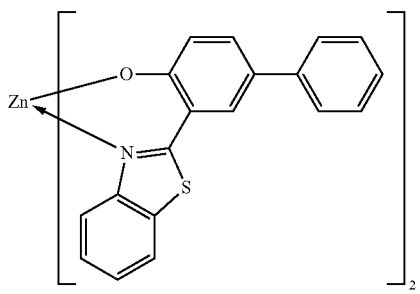

The exemplified compounds can be classified into several groups depending on a relationship between a ligand and a metal from the viewpoint of the stability of a metal complex itself.

Here, for ligands represented in the following type I to type III, distances between a nitrogen atom and oxygen atom included in each of the ligands and serving to coordinate to a metal atom are compared. The distances were each determined as follows: the stable structure of each of the ligands was calculated by employing an MM2 method as molecular mechanical calculation, and then the distance between the nitrogen atom and the oxygen atom was calculated from the structure.

the benzoquinolinol ligand in which the distance between the nitrogen atom and the oxygen atom is long.

The metal complexes represented by Exemplified Compounds H101 to H115 are each a complex in which a central metal is Mg and a ligand is a quinolinol derivative. The quinolinol derivative is a ligand capable of producing a stable complex based on the ionic radius of Mg and is a compound having a small molecular weight. Accordingly, the complex can sublimate at a low sublimation temperature. The metal complexes represented by H116 to H118 are each a complex in which a central metal is Mg and a ligand is a phenylimidazole derivative. According to calculation, a distance between a nitrogen atom and oxygen atom in the phenylimidazole derivative is 2.56 Å, and hence the ligand can complex Mg. The ligand itself has a wide bang gap and hence the ligand is suitable for obtaining a high $T_1$ energy. The metal complexes represented by H119 to H125 are each a complex in which a central metal is Mg and a ligand is a phenylbenzoxazole derivative. A benzoxazole ring is a stable heterocycle. In addition, according to calculation, a distance between a nitrogen atom and oxygen atom in the benzoxazole derivative is 2.69 Å, and hence the ligand can produce a stable Mg complex. In addition, the ligand is a ligand suitable for the utilization of a high $T_1$ energy because of its wide bang gap. Therefore, an organic light-emitting element having high light-emitting efficiency can be obtained. The metal complexes represented by H126 to H136 are each a complex in which a central metal is Mg and a ligand is a phenylbenzothiazole derivative. A benzothiazole ring is a stable heterocycle and is a ligand capable of producing the most stable complex. Accordingly, the ligand is suitable for improving the stability and element lifetime of an element. By the way, the introduction of a substituent into any one of the ligands described above can suppress its stacking. Accordingly, the introduction can improve the sublimability of a complex and can change the band gap of the complex. It should be noted that a carbon atom adjacent to the nitrogen atom has high activity and hence the activity of the carbon atom can be controlled through substitution with a methyl group or an isopropyl group.

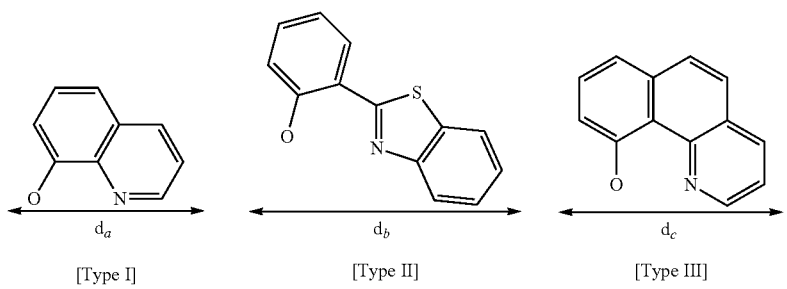 [SMILES: Oc1cccc2cccnc12 ; Oc1ccccc1-c1nc2ccccc2s1 ; Oc1cccc2ccc3cccnc3c12]

[Type I]   [Type II]   [Type III]

As a result of the calculation, the $d_a$ of a quinolinol ligand (type I) was found to be 2.68 Å, the $d_b$ of a phenylbenzothiazole ligand (type II) was found to be 2.60 Å, and the $d_c$ of a benzoquinolinol ligand (type III) was found to be 2.52 Å.

Meanwhile, the respective metal ionic radii of Mg, Zn, and Be are 0.75 Å, 0.83 Å, and 0.30 Å, respectively. In that case, Mg and Zn as metals having large ionic radii are suitable for the quinolinol ligand as the type I, and Be as a metal having a small metal ionic radius is suitable for the phenylbenzoxazole ligand as the type III. By the same reason, Be is also suitable for the phenylbenzothiazole ligand or the benzoquinolinol ligand. In actuality, when Mg or Zn is selected as a metal atom to be incorporated into a complex, it is difficult to synthesize a complex containing H201 to H206 are each a complex in which a central metal is Be and a ligand is a quinolinol derivative. Although the stability of each of the complexes is not very high in consideration of the ionic radius of a Be atom, the complex can sublimate at a low sublimation temperature because of its small molecular weight. H207 to H215 are each a complex in which a central metal is Be and a ligand is a benzoquinolinol derivative. A benzoquinolinol ring is a stable heterocycle. In addition, in consideration of the ionic radius of Be, the complex containing the benzoquinolinol ligand is a stable complex out of the Be complexes, and hence can provide a high-efficiency and long-lifetime organic light-emitting element. H216 to H218 are each a metal complex in which a central metal is Be, and each have a ligand having a wide band gap and suitable upon utilization of a high $T_1$ energy. Therefore, a high-efficiency organic light-emitting element can be obtained. H219 to H225 are each a complex in which a central metal is Be and a ligand is a phenylbenzoxazole derivative. A benzoxazole ligand is a stable heterocycle and is hence a ligand capable of producing a stable Be complex. In addition, the benzoxazole ligand is suitable for the utilization of a high $T_1$ energy and hence can provide a high-efficiency organic light-emitting element. H226 to H236 are each a complex in which a central metal is Be and a ligand is a phenylbenzothiazole derivative. A benzothiazole ligand is a stable heterocycle and is a ligand capable of producing the most stable Be complex. In addition, the complex has a $T_1$ energy suitable for red phosphorescence, and hence can provide a high-efficiency and long-lifetime organic light-emitting element. By the way, the introduction of a substituent into any one of the ligands described above can suppress its stacking. Accordingly, the introduction can improve the sublimability of a complex and can change the band gap of the complex. It should be noted that a carbon atom adjacent to the nitrogen atom has high activity and hence the activity of the carbon atom can be controlled through substitution with a methyl group or an isopropyl group.

H301 to H315 are each a complex in which a central metal is Zn and a ligand is a quinolinol derivative. The ligand can produce an extremely stable complex based on the ionic radius of a Zn complex and has a small molecular weight, and hence the complex can sublimate at a low sublimation temperature. In addition, the introduction of a substituent suppresses the stacking of the ligand, and hence can improve the sublimability of the complex and can change the band gap of the complex. H316 to H318 are each a complex in which a central metal is Zn and a ligand is a phenylimidazole derivative. A distance between a nitrogen atom and oxygen atom in the ligand is 2.56 Å, and hence the ligand can complex Zn. The ligand itself has a wide bang gap and hence the ligand is suitable upon utilization of a high $T_1$ energy. The introduction of a substituent into any one of the ligands described above can suppress its stacking. Accordingly, the introduction can improve the sublimability of a complex and can change the band gap of the complex. It should be noted that a carbon atom adjacent to the nitrogen atom has high activity and hence the activity of the carbon atom can be controlled through substitution with a methyl group or an isopropyl group.

(7) Other Materials

As described above, in the organic light-emitting element of the present invention, the emission layer contains at least the iridium complex represented by the general formula [1] as a guest and the heterocycle-containing compound as a host. It should be noted that in the present invention, conventionally known low-molecular weight and high-molecular weight materials can each be used as required in addition to those compounds. More specifically, a hole-injectable/transportable material, a host, a light emission assist material, an electron-injectable/transportable material, or the like can be used together with the iridium complex and the heterocycle-containing compound.

Examples of those materials are listed below.

The hole-injectable/transportable material is preferably a material having a high hole mobility so that the injection of a hole from the anode may be facilitated and the injected hole can be transported to the emission layer. In addition, the material is preferably a material having a high glass transition point for preventing the deterioration of film quality such as crystallization in the organic light-emitting element. Examples of the low-molecular weight and high-molecular weight materials each having hole-injecting/transporting performance include a triarylamine derivative, an arylcarbazole derivative, a phenylenediamine derivative, a stilbene derivative, a phthalocyanine derivative, a porphyrin derivative, poly(vinyl carbazole), poly(thiophene), and other conductive polymers. Further, the hole-injectable/transportable material is suitably used for the electron blocking layer as well.

Specific examples of a compound to be used as the hole-injectable/transportable material are shown below. However, the compound is of course not limited thereto.

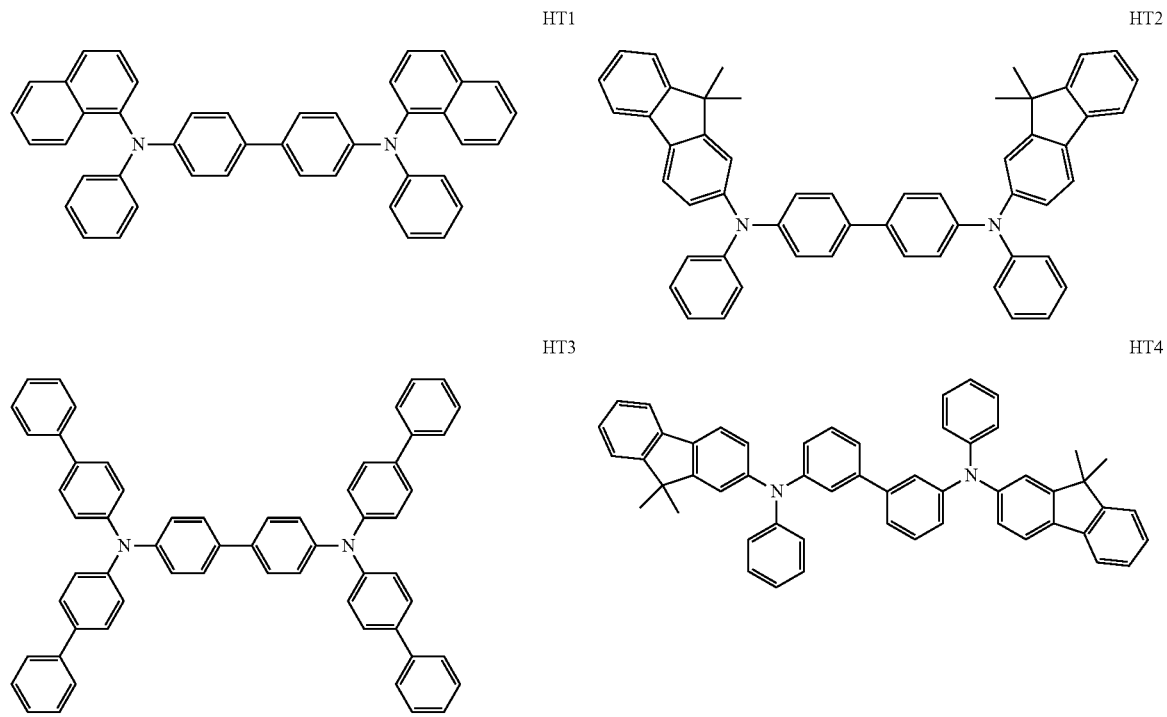

-continued
HT5
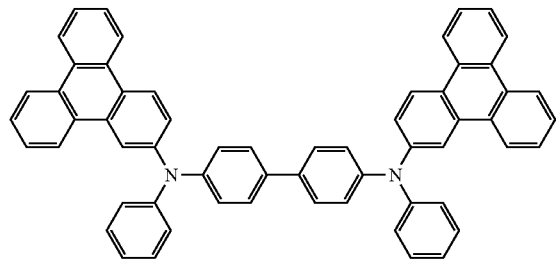
HT6
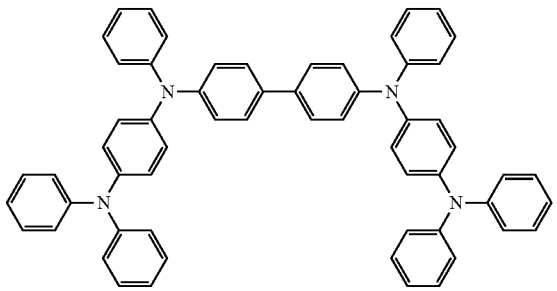
HT7
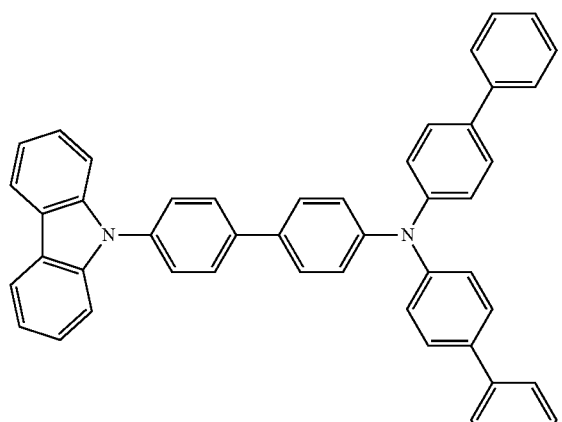
HT8
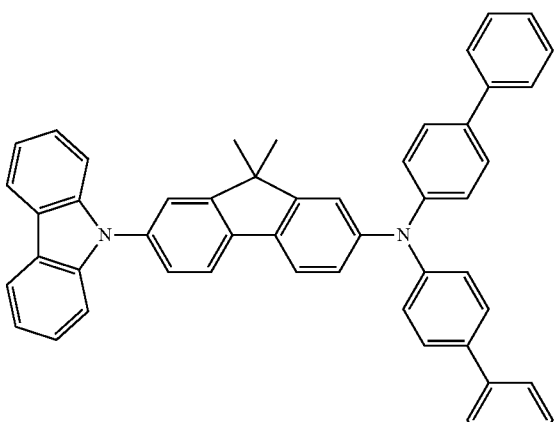
HT9
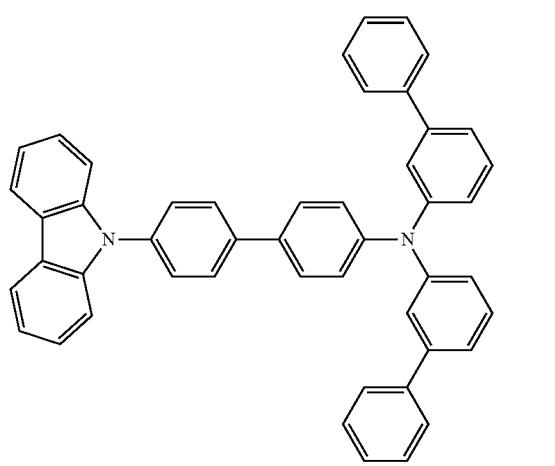
HT10
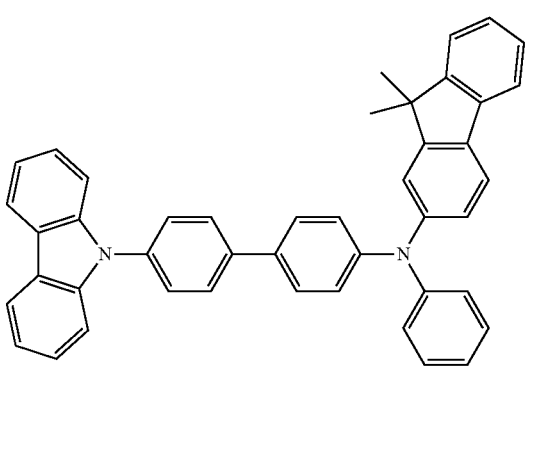
HT11
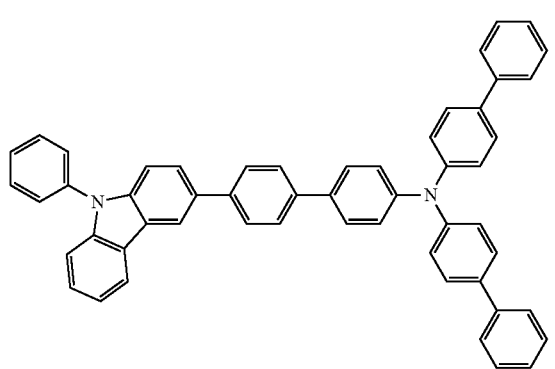
HT12
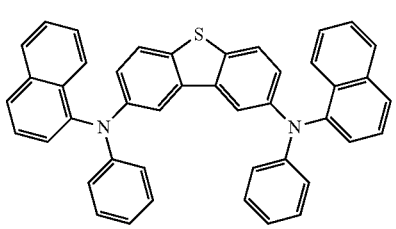

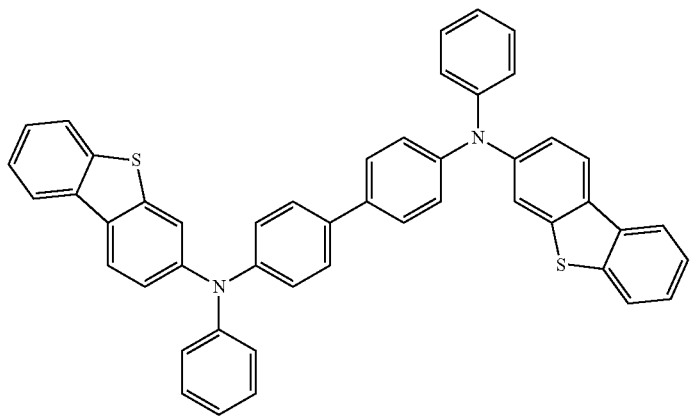

HT13

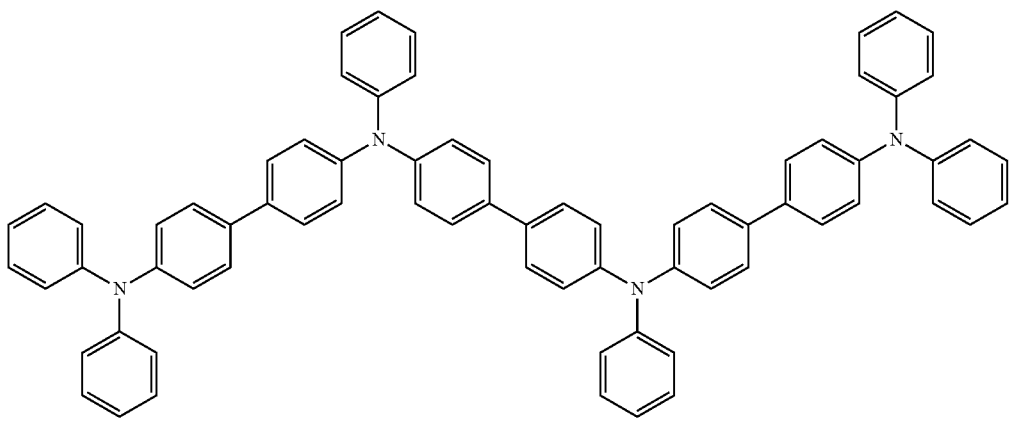

HT14

Examples of the light-emitting material mainly involved in a light-emitting function include: condensed ring compounds (such as a fluorene derivative, a naphthalene derivative, a pyrene derivative, a perylene derivative, a tetracene derivative, an anthracene derivative, and rubrene); a quinacridone derivative; a coumarin derivative; a stilbene derivative; an organic aluminum complex such as tris(8-quinolinolato)aluminum; a platinum complex; a rhenium complex; a copper complex; a europium complex; a ruthenium complex; and polymer derivatives such as a poly(phenylene vinylene) derivative, a poly(fluorene) derivative, and a poly(phenylene) derivative in addition to the iridium complex represented by the general formula [1] or a derivative thereof.

Specific examples of a compound to be used as the light-emitting material are shown below. However, the compound is of course not limited thereto.

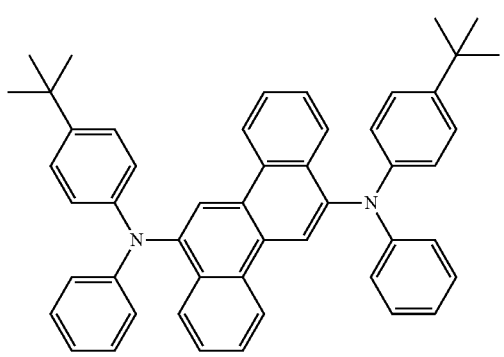

BD1

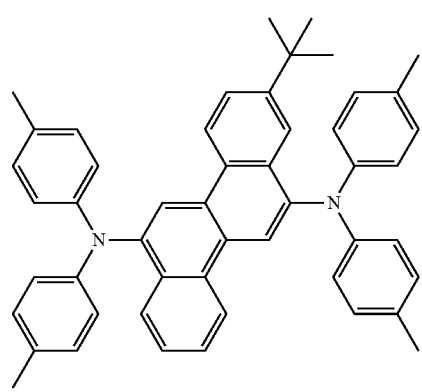

BD2

-continued
BD3
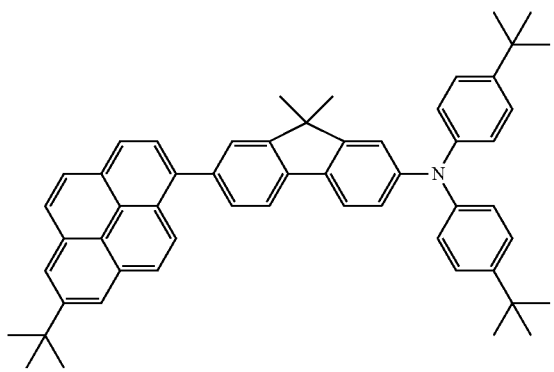
BD4
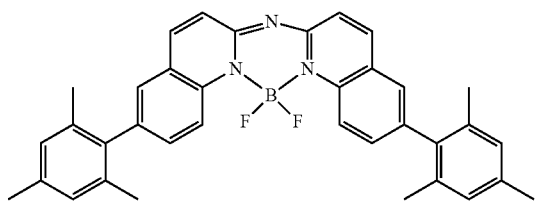
BD5
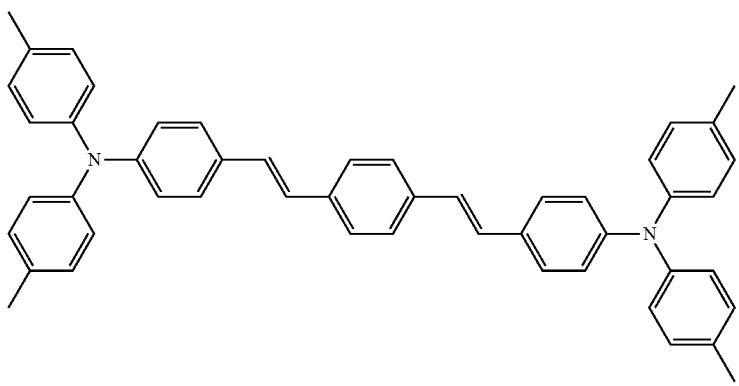
BD6
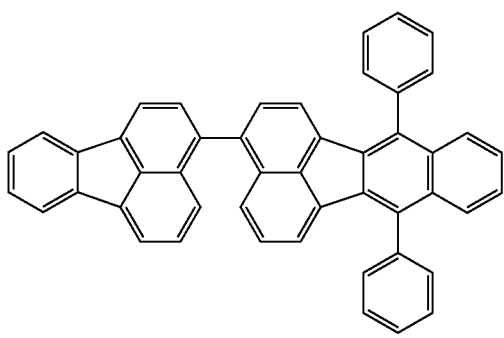
BD7
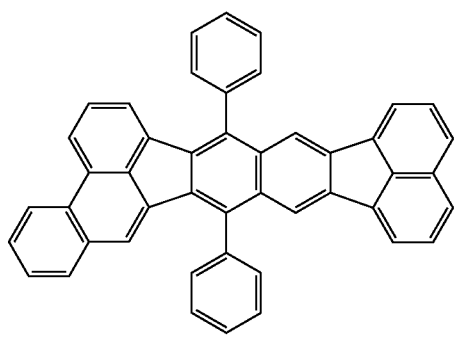
BD8
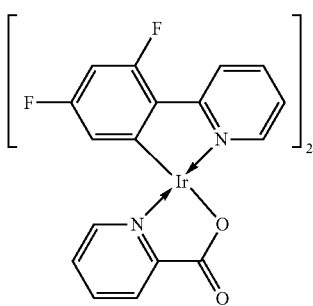
GD1
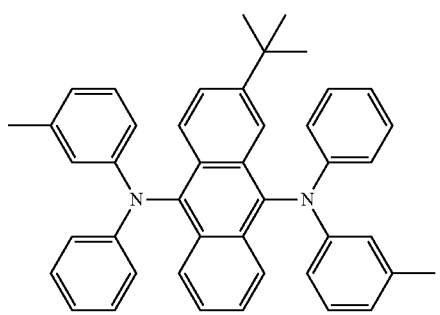

-continued
GD2
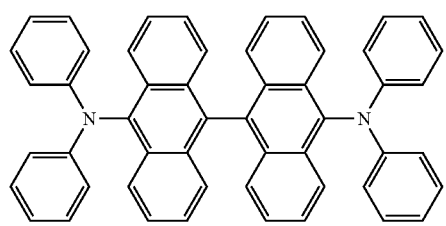
GD3
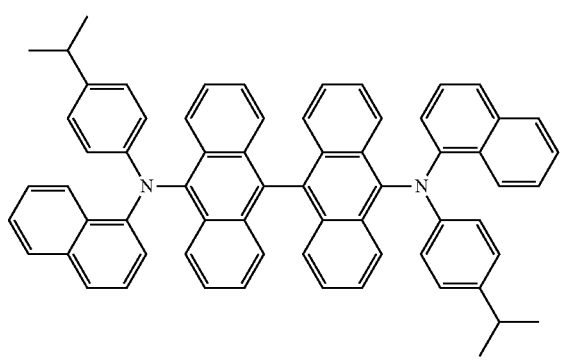
GD4
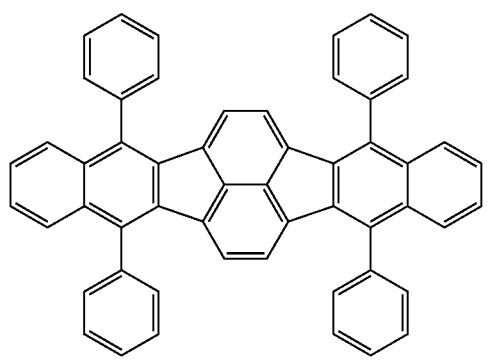
GD5
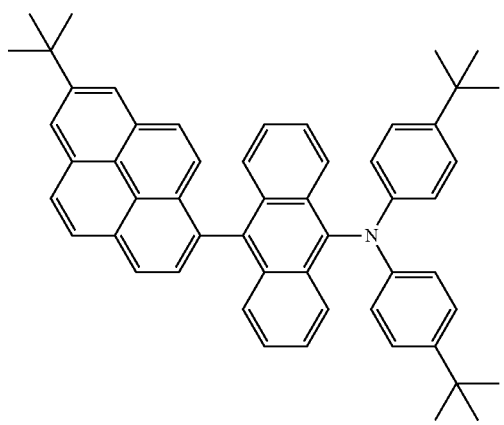
GD6
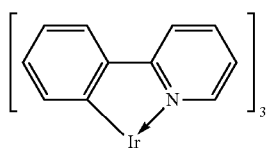
GD7
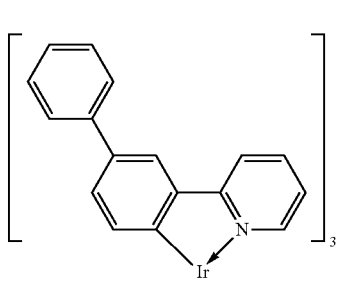
GD8
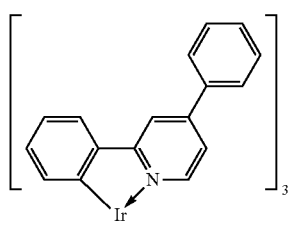
RD1
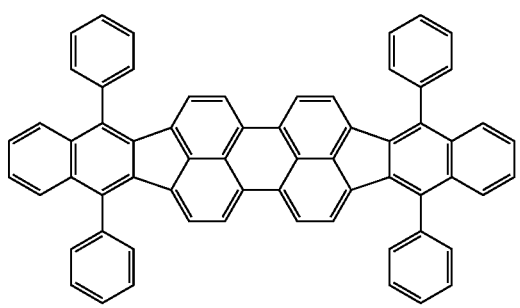

-continued

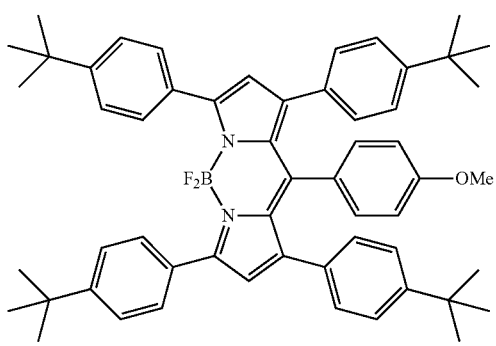
RD2

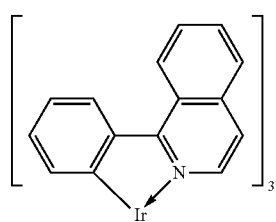
RD3

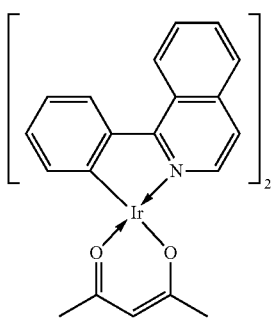
RD4

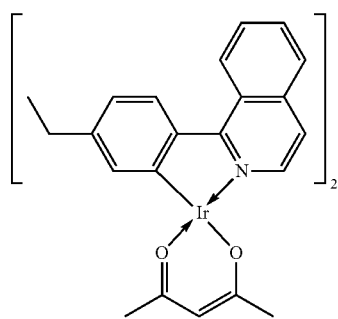
RD5

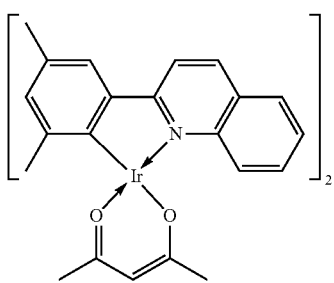
RD6

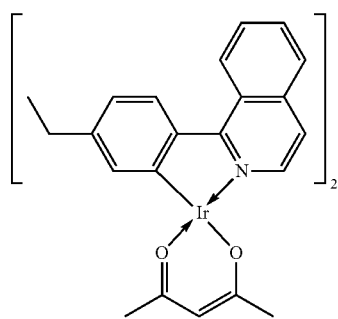

RD7

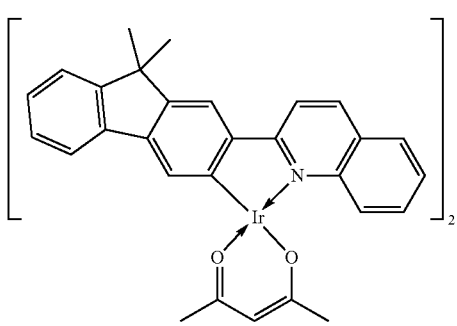
RD8

Examples of the host or assist material to be incorporated into the emission layer include: an aromatic hydrocarbon compound or a derivative thereof; a carbazole derivative; a dibenzofuran derivative; a dibenzothiophene derivative; an organic aluminum complex such as tris(8-quinolinolato) aluminum; and an organic beryllium complex in addition to the heterocycle-containing compound.

Specific examples of a compound to be used as the host or assist material to be incorporated into the emission layer are shown below. However, the compound is of course not limited thereto.

EM1
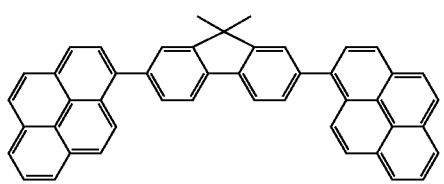
EM2
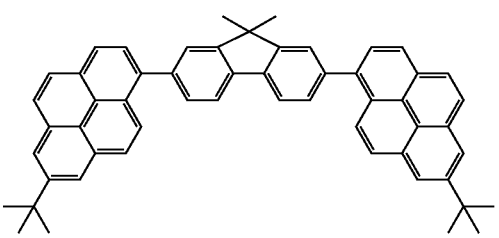
EM3
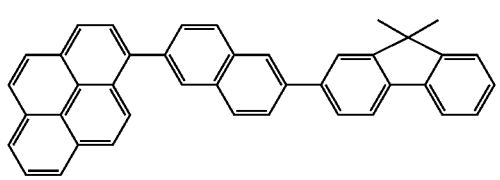
EM4
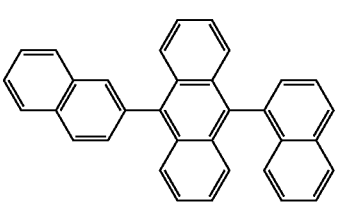
EM5
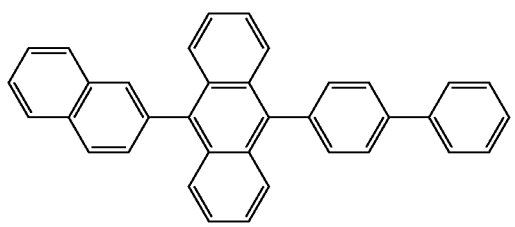
EM6
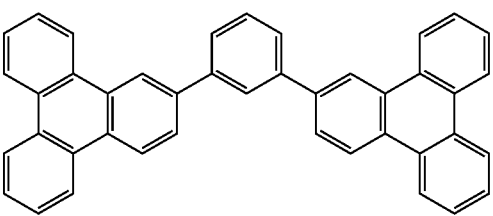
EM7
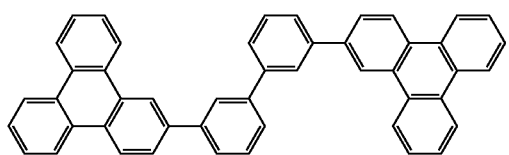
EM8
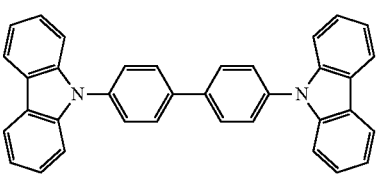
EM9
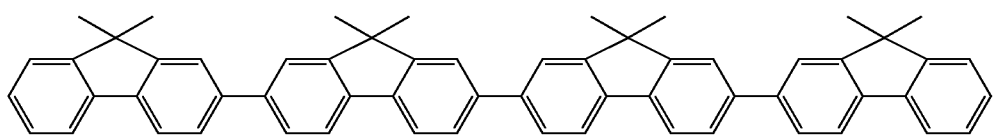
EM10
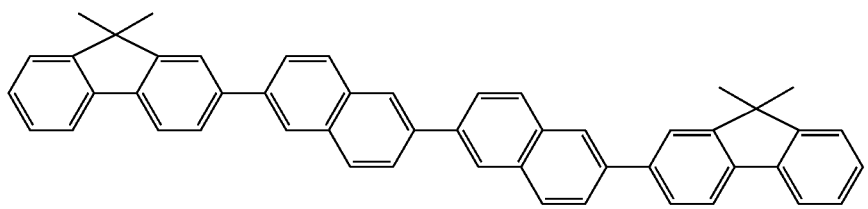
EM11
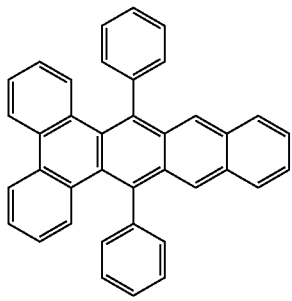
EM12
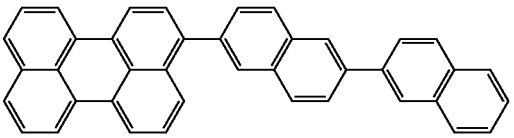

EM13

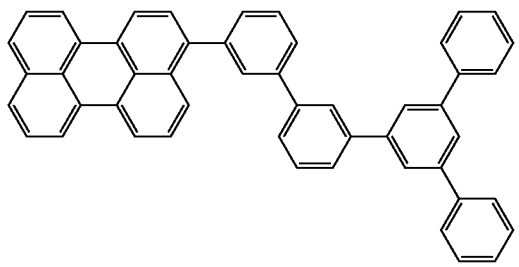

EM14

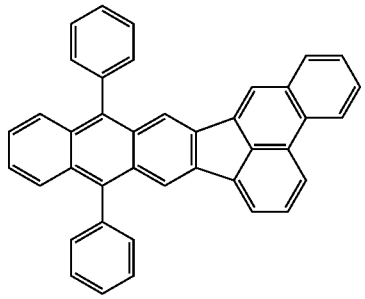

EM15

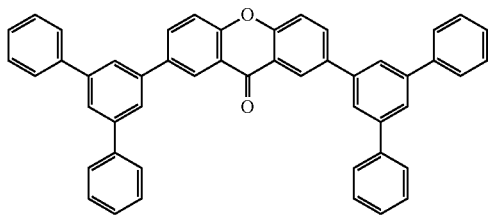

EM16

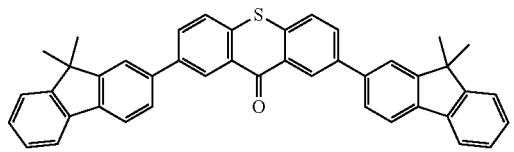

EM17

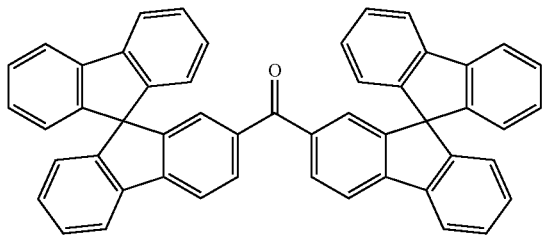

The electron-injectable/transportable material can be arbitrarily selected from materials that allow electrons to be easily injected from the cathode and can transport the injected electrons to the emission layer in consideration of, for example, the balance with the hole mobility of the hole-transportable material. Examples of the material having electron-injecting performance and electron-transporting performance include an oxadiazole derivative, an oxazole derivative, a pyrazine derivative, a triazole derivative, a triazine derivative, a quinoline derivative, a quinoxaline derivative, a phenanthroline derivative, and an organic aluminum complex. Further, the electron-injectable/transportable material is suitably used for the hole blocking layer as well.

Specific examples of a compound to be used as the electron-injectable/transportable material are shown below. However, the compound is of course not limited thereto.

-continued

ET2

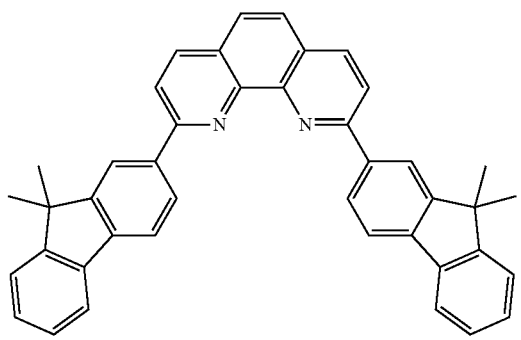

ET1

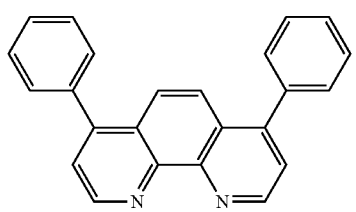

ET3

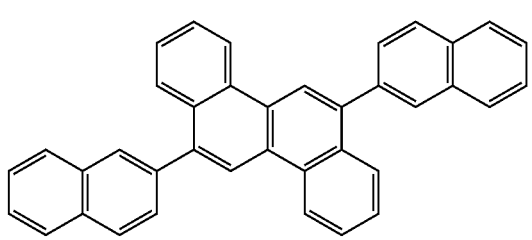

ET4
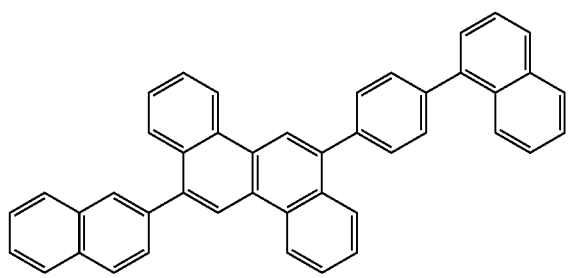

ET5
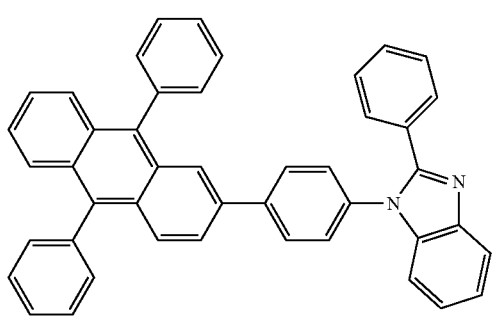

ET6
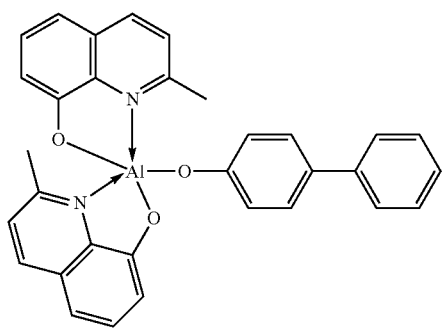

ET7
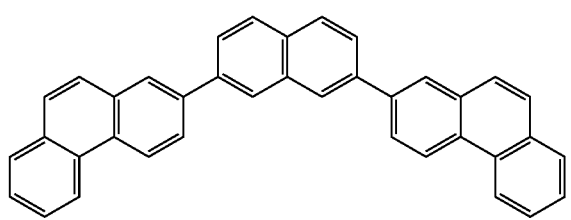

ET8
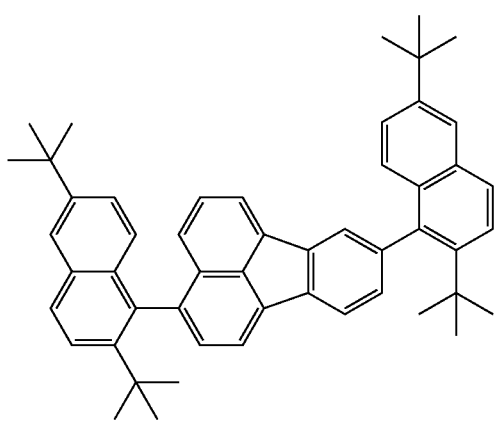

In addition, a mixture obtained by mixing the electron-injectable/transportable material and a compound of an alkali metal or an alkaline earth metal may be used as the electron-injectable/transportable material. Examples of the metal compound to be mixed with the electron-injectable/transportable material include LiF, KF, $Cs_2CO_3$, and CsF.

A constituent material for the anode desirably has as large a work function as possible. For example, there can be used: metal simple substances such as gold, platinum, silver, copper, nickel, palladium, cobalt, selenium, vanadium, and tungsten or alloys obtained by combining these metal simple substances; metal oxides such as tin oxide, zinc oxide, indium oxide, indium tin oxide (ITO), indium zinc oxide, gallium zinc oxide, and indium gallium zinc oxide; and conductive polymers such as polyaniline, polypyrrole, and polythiophene. In particular, a transparent oxide semiconductor (e.g., indium tin oxide (ITO), indium zinc oxide, or indium gallium zinc oxide) has a high mobility, and hence is suitable for an electrode material.

One kind of those electrode substances may be used alone, or two or more kinds thereof may be used in combination. In addition, the anode may be of a single-layer construction or may be of a multilayer construction.

On the other hand, a constituent material for the cathode desirably has as small a work function as possible. Examples thereof include: alkali metals such as lithium; alkaline earth metals such as calcium; and metal simple substances such as aluminum, titanium, manganese, silver, lead, and chromium. Alternatively, alloys obtained by combining those metal simple substances can be used. For example, a magnesium-silver alloy, an aluminum-lithium alloy, or an aluminum-magnesium alloy can be used. A metal oxide such as indium tin oxide (ITO) can also be utilized. One kind of those electrode substances may be used alone, or two or more kinds thereof may be used in combination. In addition, the cathode may be of a single-layer construction or may be of a multilayer construction.

The organic compound layer (such as the hole injection layer, the hole transport layer, the electron blocking layer, the emission layer, the hole blocking layer, the electron transport layer, or the electron injection layer) for forming the organic light-emitting element of the present invention is formed by the following method.

A dry process such as a vacuum vapor deposition method, an ionized vapor deposition method, sputtering, or a plasma process can be used for the formation of the organic compound layer for forming the organic light-emitting element of the present invention. In addition, a wet process involving dissolving the constituent materials in an appropriate solvent and forming a layer by a known application method (such as spin coating, dipping, a casting method, an LB method, or an ink jet method) can be used instead of the dry process.

Here, when the layer is formed by the vacuum vapor deposition method, the solution application method, or the like, the layer hardly undergoes crystallization or the like and is excellent in stability over time. In addition, when the layer is formed by the application method, the film can be formed by using the constituent materials in combination with an appropriate binder resin.

Examples of the binder resin include, but not limited to, a polyvinyl carbazole resin, a polycarbonate resin, a polyester resin, an ABS resin, an acrylic resin, a polyimide resin, a phenol resin, an epoxy resin, a silicone resin, and a urea resin.

In addition, one kind of those binder resins may be used alone as a homopolymer or a copolymer, or two or more kinds thereof may be used as a mixture. Further, a known additive such as a plasticizer, an antioxidant, or a UV absorber may be used in combination as required.

(10) Application of Organic Light-Emitting Element of the Present Invention

The organic light-emitting element of the present invention can be used as a constituent member for a display apparatus or lighting apparatus. In addition, the element finds use in applications such as an exposure light source for an image-forming apparatus of an electrophotographic system, a backlight for a liquid crystal display apparatus, and a light-emitting apparatus including a white light source and a color filter. Examples of the color filter include filters that transmit light beams having three colors, i.e., red, green, and blue colors.

A display apparatus of the present invention includes the organic light-emitting element of the present invention in its display portion. It should be noted that the display portion includes multiple pixels.

In addition, the pixels each have the organic light-emitting element of the present invention and a transistor as an example of an active element (switching element) or amplifying element for controlling emission luminance, and the anode or cathode of the organic light-emitting element and the drain electrode or source electrode of the transistor are electrically connected to each other. Here, the display apparatus can be used as an image display apparatus for a PC or the like. The transistor is, for example, a TFT element and the TFT element is provided on, for example, the insulating surface of a substrate.

The display apparatus may be an information processing apparatus that includes an image input portion for inputting image information from, for example, an area CCD, a linear CCD, or a memory card, and displays an input image on its display portion.

In addition, the display portion of an imaging apparatus or inkjet printer may have a touch panel function. The drive system of the touch panel function is not particularly limited.

In addition, the display apparatus may be used in the display portion of a multifunction printer.

A lighting apparatus is an apparatus for lighting, for example, the inside of a room. The lighting apparatus may emit light having any one of the following colors: a white color (having a color temperature of 4,200 K), a daylight color (having a color temperature of 5,000 K), and colors ranging from blue to red colors.

A lighting apparatus of the present invention includes the organic light-emitting element of the present invention and an inverter circuit connected to the organic light-emitting element. It should be noted that the lighting apparatus may further include a color filter.

An image-forming apparatus of the present invention is an image-forming apparatus including: a photosensitive member; a charging unit for charging the surface of the photosensitive member; an exposing unit for exposing the photosensitive member to form an electrostatic latent image; and a developing unit for developing the electrostatic latent image formed on the surface of the photosensitive member. Here, the exposing unit to be provided in the image-forming apparatus includes the organic light-emitting element of the present invention.

In addition, the organic light-emitting element of the present invention can be used as a constituent member for an exposing apparatus for exposing a photosensitive member. An exposing apparatus including a plurality of the organic light-emitting elements of the present invention is, for example, an exposing apparatus in which the organic light-emitting elements of the present invention are placed to form a line along a predetermined direction.

Next, the display apparatus of the present invention is described with reference to the drawing. FIG. 1 is a schematic sectional view illustrating an example of a display apparatus including an organic light-emitting element and a TFT element connected to the organic light-emitting element. It should be noted that the organic light-emitting element of the present invention is used as the organic light-emitting element constituting a display apparatus 1 of FIG. 1.

The display apparatus 1 of FIG. 1 includes a substrate 11 made of glass or the like and a moisture-proof film 12 for protecting a TFT element or organic compound layer, the film being provided on the substrate. In addition, a metal gate electrode 13 is represented by reference numeral 13, a gate insulating film 14 is represented by reference numeral 14, and a semiconductor layer is represented by reference numeral 15.

A TFT element 18 includes the semiconductor layer 15, a drain electrode 16, and a source electrode 17. An insulating film 19 is provided on the TFT element 18. An anode 21 constituting the organic light-emitting element and the source electrode 17 are connected to each other through a contact hole 20.

It should be noted that a system for the electrical connection between the electrode (anode or cathode) in the organic light-emitting element and the electrode (source electrode or drain electrode) in the TFT is not limited to the aspect illustrated in FIG. 1. In other words, one of the anode and the cathode, and one of the source electrode and drain electrode of the TFT element have only to be electrically connected to each other.

Although multiple organic compound layers are illustrated like one layer in the display apparatus 1 of FIG. 1, an organic compound layer 22 may be multiple layers. A first protective layer 24 and second protective layer 25 for suppressing the deterioration of the organic light-emitting element are provided on a cathode 23.

When the display apparatus 1 of FIG. 1 is a display apparatus that emits white light, an emission layer in the organic compound layer 22 in FIG. 1 may be a layer obtained by mixing a red light-emitting material, a green light-emitting material, and a blue light-emitting material. In addition, the layer may be a laminated emission layer obtained by laminating a layer formed of the red light-emitting material, a layer formed of the green light-emitting material, and a layer formed of the blue light-emitting material. Further, alternatively, the following aspect is permitted: the layer formed of the red light-emitting material, the layer formed of the green light-emitting material, and the layer formed of the blue light-emitting material are, for example, arranged side by side to form domains in one emission layer.

Although the transistor is used as a switching element in the display apparatus 1 of FIG. 1, an MIM element may be used instead of the transistor as the switching element.

In addition, the transistor to be used in the display apparatus 1 of FIG. 1 is not limited to a transistor using a monocrystalline silicon wafer and may be a thin-film transistor including an active layer on the insulating surface of a substrate. A thin-film transistor using monocrystalline silicon as the active layer, a thin-film transistor using non-monocrystalline silicon such as amorphous silicon or microcrystalline silicon as the active layer, or a thin-film transistor using a non-monocrystalline oxide semiconductor such as an indium zinc oxide or an indium gallium zinc oxide as the active layer is also permitted. It should be noted that the thin-film transistor is also called a TFT element.

The transistor in the display apparatus 1 of FIG. 1 may be formed in a substrate such as an Si substrate. Here, the phrase "formed in a substrate" means that the transistor is produced by processing the substrate itself such as an Si substrate. In other words, the presence of the transistor in the substrate can be regarded as follows: the substrate and the transistor are integrally formed.

Whether the transistor is provided in the substrate is selected depending on definition. In the case of, for example, a definition of about a QVGA per inch, the organic light-emitting element is preferably provided in the Si substrate.

As described above, the driving of the display apparatus using the organic light-emitting element of the present invention enables display that has good image quality and is stable over a long time period.

EXAMPLES

Hereinafter, the present invention is described in detail by way of Examples. However, the present invention is not limited to Examples below.

Synthesis Example 1

Synthesis of Exemplified Compound Ir-113

(2) Synthesis of Exemplified Compound Ir-113

The following reagents and solvent were loaded in a 100-ml recovery flask.

Intermediate 1: 0.864 g (1.21 mmol)
Ligand 1: 0.802 g (2.42 mmol)
Diethylene glycol dimethyl ether: 50 ml Next, the reaction solution was heated to 160° C. under nitrogen. After that, the reaction solution was stirred at the temperature (160° C.) for 6 hours. At this time, the color of the reaction solution changed from a yellow color to a dark red color. Next, the temperature of the reaction solution was reduced to 120° C. and then the following reagents were added. Acetylacetone (manufactured by Tokyo Chemical Industry Co., Ltd.): 0.606 g (6.05 mmol)

Sodium carbonate: 0.641 g (6.05 mmol)

Next, the reaction solution was heated to 120° C. under nitrogen. After that, the reaction solution was stirred at the temperature (120° C.) for 2 hours. Next, water was added to a viscous body, which had been produced by removing the solvent of the reaction solution by distillation under reduced pressure, to precipitate a solid. Next, the solid was filtered and then vacuum-dried, followed by purification with a neutral alumina gel column (toluene:ethyl acetate=10:1). Thus, 0.160 g of Exemplified Compound Ir-113 was obtained (yield: 17%).

Matrix-assisted laser desorption/ionization time-of-flight mass spectrometry (MALDI-TOF MS, Autoflex LRF manufactured by Bruker) confirmed that the compound had an M+ of 776.2.

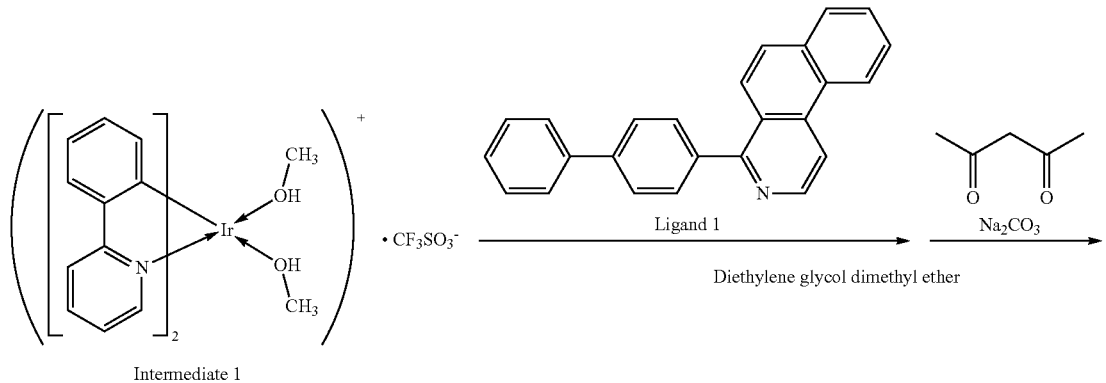

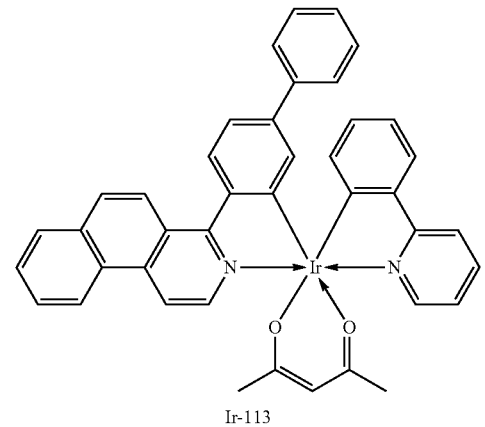

Ir-113

(1) Synthesis of Intermediate 1 and Ligand 1

Intermediate 1 was synthesized according to the method described in Patent Literature 4. In addition, Ligand 1 was synthesized according to a method described in Patent Literature 5.

Further, the structure of the compound was identified by $^1$H-NMR measurement.

$^1$H-NMR {(CD$_3$)$_2$S=O, 500 MHz} δ (ppm): 8.98-8.96 (1H, m), 8.86 (1H, d), 8.73 (1H, d), 8.60 (1H, d), 8.51 (1H, d), 8.26 (1H, d), 8.20-8.17 (3H, m), 7.99 (1H, t), 7.89-7.85

(2H, m), 7.70 (1H, d), 7.45 (1H, t), 7.36-7.33 (2H, m), 7.28-7.24 (3H, m), 7.20 (1H, dd), 6.74 (1H, t), 6.54 (1H, t), 6.48 (1H, d), 5.99 (1H, d), 5.30 (1H, s), 1.77 (3H, s), 1.70 (3H, s)

The phosphorescence spectrum of a dilute toluene solution ($1\times10^{-5}$ M) of Exemplified Compound Ir-113 was measured with an F-4500 manufactured by Hitachi, Ltd. It should be noted that the measurement was performed under the following conditions: the measurement was performed under a nitrogen atmosphere at room temperature and an excitation wavelength was set to 450 nm. As a result of the measurement, the peak wavelength of the phosphorescence spectrum was 609 nm.

The vacuum thermogravimetric analysis of Exemplified Compound Ir-113 was performed with a TG-DTA 2410SA manufactured by Bruker and then its sublimation temperature ($T_{sub}$) was determined by the following procedure. First, the thermogravimetric change of the sample was measured under a vacuum of $1\times10^{-3}$ Pa. Next, the resultant measured result was substituted into the following calculation equation (i) to determine a change in saturated vapor pressure P [Pa] with temperature:

$$P = m/\{4.38\times10^{-3}\cdot(M/T)^{1/2}\} \quad (i)$$

(m: an evaporation rate per unit area [kg/m²·s], M: the molecular weight of the complex, T: the temperature of an evaporation surface [K]).

It should be noted that m is determined from the following equation (ii):

$$m = (1/U)\cdot(d\Delta W/dt) \quad (ii)$$

(U: the area of a sample dish [m²], $d\Delta W/dt$: the first derivation of a thermogravimetric curve with respect to time).

Here, a weight change rate within 20 seconds {(amount of weight change)/(20 seconds)} was used as the $d\Delta W/dt$. In addition, a temperature after a lapse of 20 seconds was used as the temperature T.

A saturated vapor pressure curve is obtained by plotting the P obtained by the calculation against the T. In the saturated vapor pressure curve, the P starts to increase immediately after the initiation of the sublimation of the complex. Here, the temperature at which the P exceeded $5\times10^{-4}$ Pa was defined as the $T_{sub}$. As a result, the $T_{sub}$ in Exemplified Compound Ir-113 was 300° C.

The atmospheric thermogravimetric/differential thermal analysis of Exemplified Compound Ir-113 was performed with a TG-DTA 2000SA manufactured by Bruker. In the resultant differential thermal curve, the temperature at which an exothermic peak started to appear was defined as the decomposition temperature ($T_d$). It should be noted that a weight reduction simultaneously occurred at the $T_d$ and hence the reaction was confirmed to be a decomposition reaction. As a result, in Exemplified Compound Ir-113, the $T_d$ was 355° C.

Synthesis Example 2

Synthesis of Exemplified Compound Ir-114

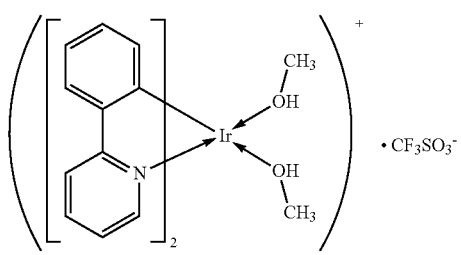

Intermediate 1

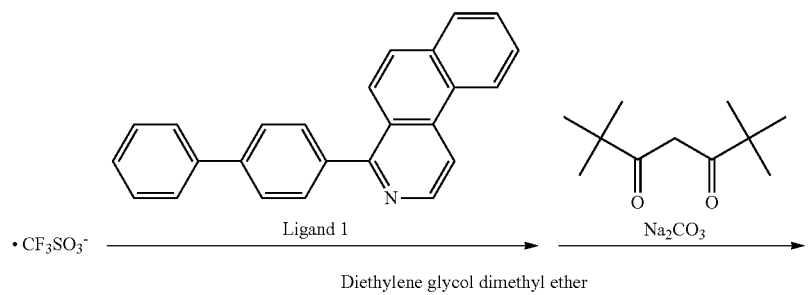

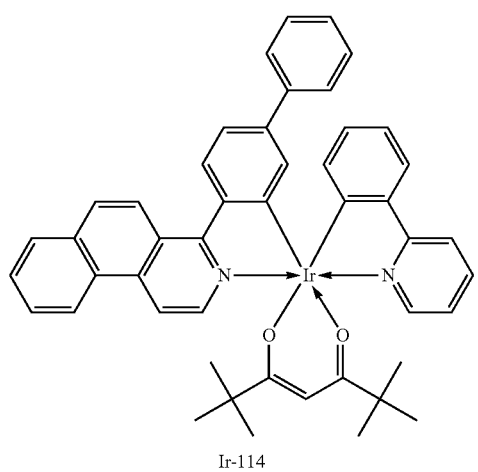

Ir-114

Exemplified Compound Ir-114 was obtained by the same method as that of Synthesis Example 1 except that in the section (2) of Synthesis Example 1, dipivaloylmethane (manufactured by Tokyo Chemical Industry Co., Ltd.) was used instead of acetylacetone.

MALDI-TOF MS confirmed that the compound had an M+ of 860.3.

Further, the structure of the compound was identified by $^1$H-NMR measurement.

$^1$H-NMR {(CD$_3$)$_2$S=O, 500 MHz} δ (ppm): 8.99-8.97 (1H, m), 8.86 (1H, d), 8.70 (1H, d), 8.50 (1H, d), 8.37 (1H, d), 8.26 (1H, d), 8.19-8.15 (3H, m), 7.96 (1H, t), 7.86-7.83 (2H, m), 7.73 (1H, d), 7.40 (1H, t), 7.36-7.28 (4H, m), 7.25 (1H, t), 7.20 (1H, dd), 6.75 (1H, t), 6.58-6.55 (2H, m), 6.20 (1H, d), 5.50 (1H, s), 0.89 (9H, s), 0.77 (9H, s)

In addition, the phosphorescence spectrum of Exemplified Compound Ir-114 in a dilute toluene solution state was measured in the same manner as in Synthesis Example 1. As a result, its peak wavelength was 612 nm. Further, the T$_{sub}$ of Exemplified Compound Ir-114 was determined in the same manner as in Example 1. As a result, the T$_{sub}$ was 270° C.

Synthesis Example 3

Synthesis of Exemplified Compound Ir-125

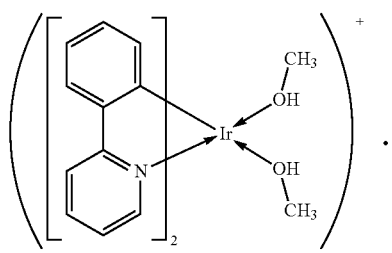

Intermediate 1

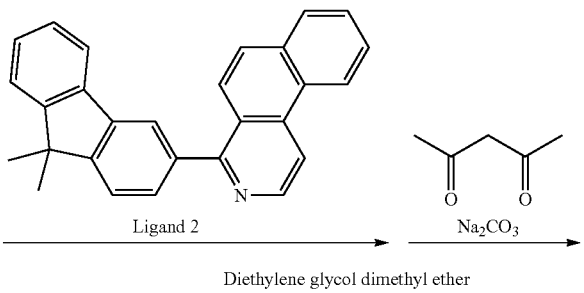

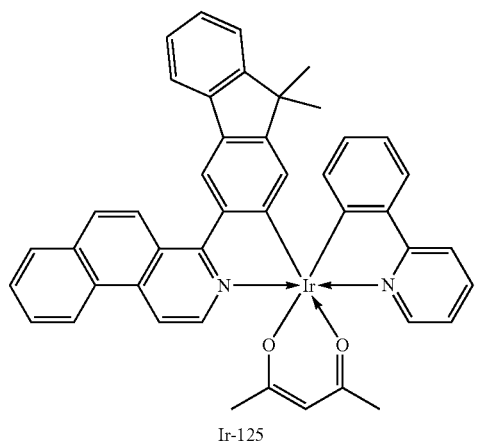

Ir-125

Exemplified Compound Ir-125 was obtained by the same method as that of Synthesis Example 1 except that in Synthesis Example 1, Ligand 2 was used instead of Ligand 1. It should be noted that Ligand 2 is a ligand synthesized with reference to Patent Literature 5.

MALDI-TOF MS confirmed that the compound had an M+ of 816.2.

In addition, the phosphorescence spectrum of Exemplified Compound Ir-125 in a dilute toluene solution state was measured in the same manner as in Synthesis Example 1. As a result, its peak wavelength was 613 nm.

Synthesis Example 4

Synthesis of Exemplified Compound Ir-106

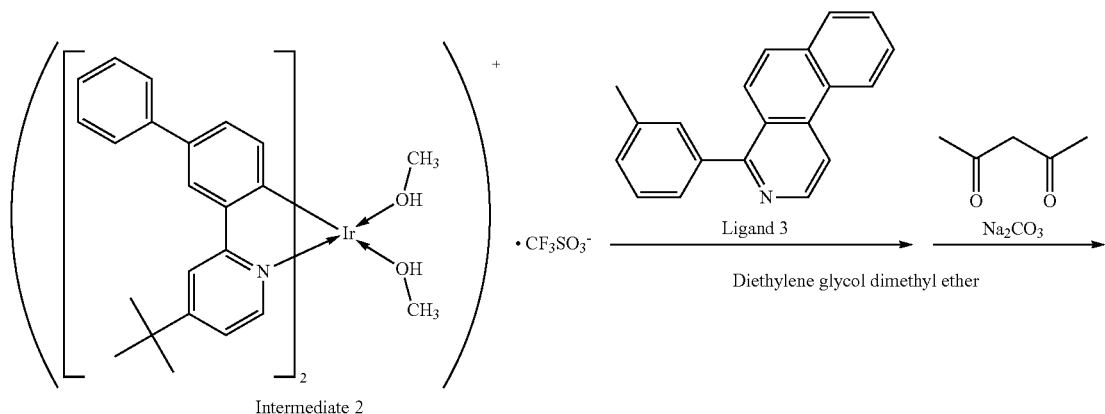

Intermediate 2

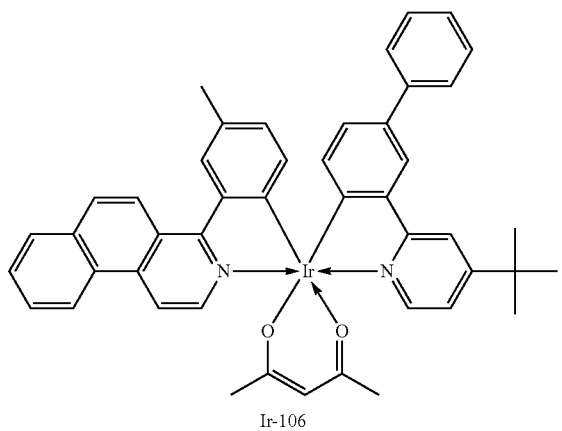

Ir-106

(1) Synthesis of Intermediate 2 and Ligand 3

Intermediate 2 (2-(biphenyl-3-yl)-4-tert-butylpyridine) was synthesized according to a method described in Patent Literature 6. In addition, Ligand 3 was synthesized according to the method described in Patent Literature 5.

(2) Synthesis of Exemplified Compound Ir-106

Exemplified Compound Ir-106 was obtained by the same method as that of Synthesis Example 1 except that in the section (2) of Synthesis Example 1, Intermediate 2 was used instead of Intermediate 1 and Ligand 3 was used instead of Ligand 1.

MALDI-TOF MS confirmed that the compound had an M+ of 846.3.

Further, the structure of the compound was identified by $^1$H-NMR measurement.

$^1$H-NMR {$(CD_3)_2S=O$, 500 MHz} δ (ppm): 8.96-8.94 (1H, m), 8.85 (1H, d), 8.69 (1H, d), 8.58 (1H, d), 8.35 (1H, d), 8.28 (1H, d), 8.18-8.15 (2H, m), 8.06 (1H, d), 7.99 (1H, s), 7.87-7.85 (2H, m), 7.59 (2H, d), 7.48 (1H, dd), 7.36 (2H, t), 7.23 (1H, t), 6.82 (1H, dd), 6.53 (1H, d), 6.18 (1H, d), 6.03 (1H, d), 5.27 (1H, s), 2.23 (3H, s), 1.75 (3H, s), 1.68 (3H, s), 1.47 (9H, s)

In addition, the phosphorescence spectrum of Exemplified Compound Ir-106 in a dilute toluene solution state was measured in the same manner as in Synthesis Example 1. As a result, its peak wavelength was 606 nm.

Further, the $T_{sub}$ and $T_d$ of Exemplified Compound Ir-106 were determined in the same manner as in Synthesis Example 1. As a result, the $T_{sub}$ and the $T_d$ were 290° C. and 375° C., respectively.

Synthesis Example 5

Synthesis of Exemplified Compound Ir-136

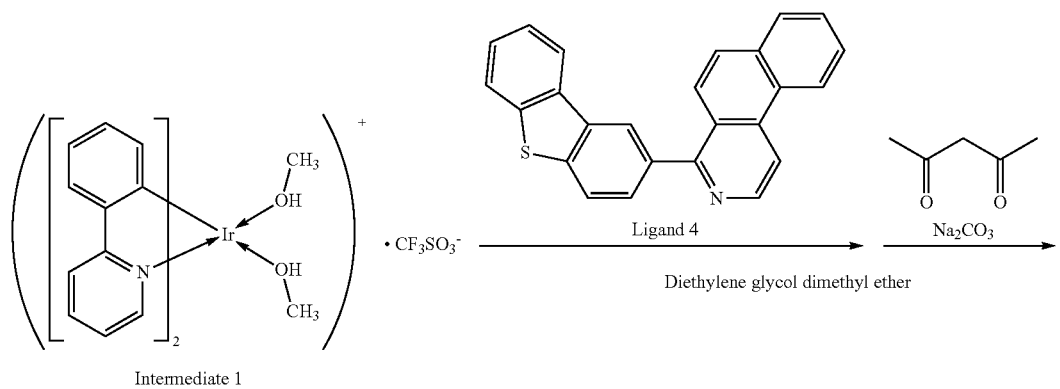

Intermediate 1

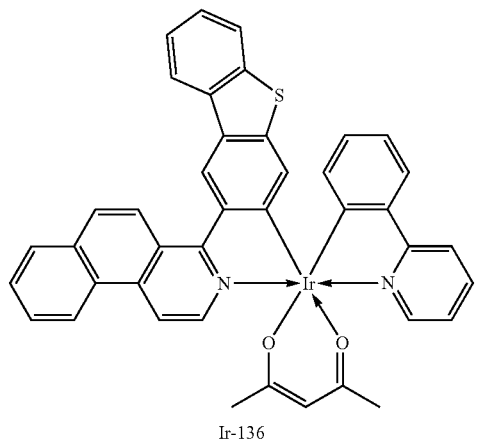

Ir-136

Exemplified Compound Ir-136 was obtained by the same method as that of Synthesis Example 1 except that in Synthesis Example 1, Ligand 4 was used instead of Ligand 1. It should be noted that Ligand 4 was synthesized according to the method described in Patent Literature 3.

MALDI-TOF MS confirmed that the compound had an $M^+$ of 806.2.

In addition, the phosphorescence spectrum of Exemplified Compound Ir-136 in a dilute toluene solution state was measured in the same manner as in Synthesis Example 1. As a result, its peak wavelength was 610 nm.

Synthesis Example 6

Synthesis of Exemplified Compound Ir-108

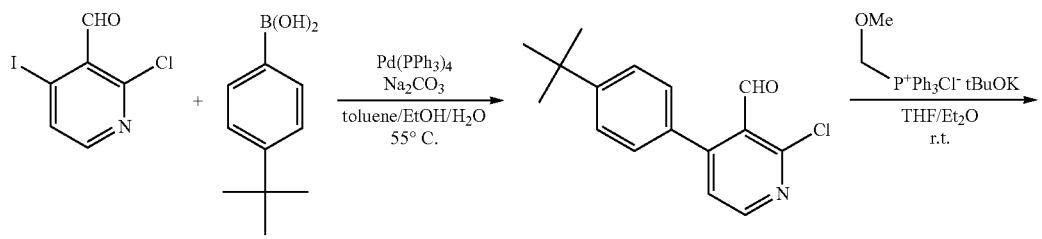

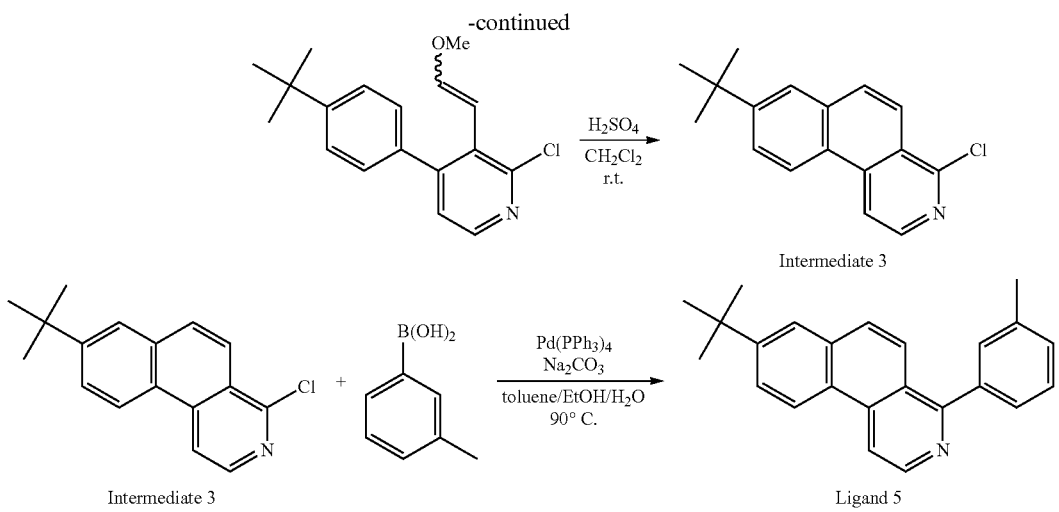

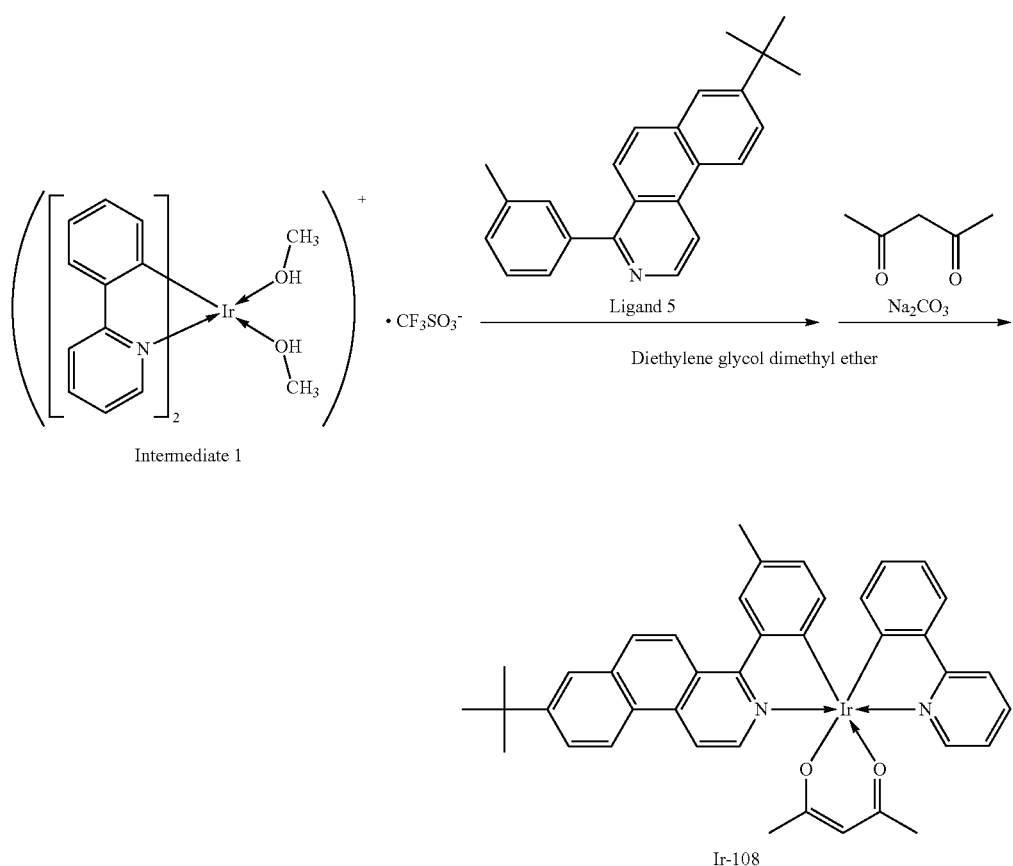

(1) Synthesis of Intermediate 3

Intermediate 3 was synthesized according to the synthesis scheme by using 2-chloro-4-iodonicotinaldehyde (manufactured by Shanghai P&T Fine Chemical) and 4-tert-butylphenylboronic acid (manufactured by Tokyo Chemical Industry Co., Ltd.) as starting raw materials.

(2) Synthesis of Ligand 5

Ligand 5 was synthesized according to the scheme by using Intermediate 3 and 3-methylphenylboronic acid (manufactured by Tokyo Chemical Industry Co., Ltd.).

(3) Synthesis of Exemplified Compound Ir-108

Exemplified Compound Ir-108 was obtained by the same method as that of Synthesis Example 1 except that in the section (2) of Synthesis Example 1, Ligand 5 was used instead of Ligand 1.

MALDI-TOF MS confirmed that the compound had an $M^+$ of 770.3.

In addition, the phosphorescence spectrum of Exemplified Compound Ir-108 in a dilute toluene solution state was measured in the same manner as in Synthesis Example 1. As a result, its peak wavelength was 605 nm.

Synthesis Example 7

Synthesis of Exemplified Compound Ir-134

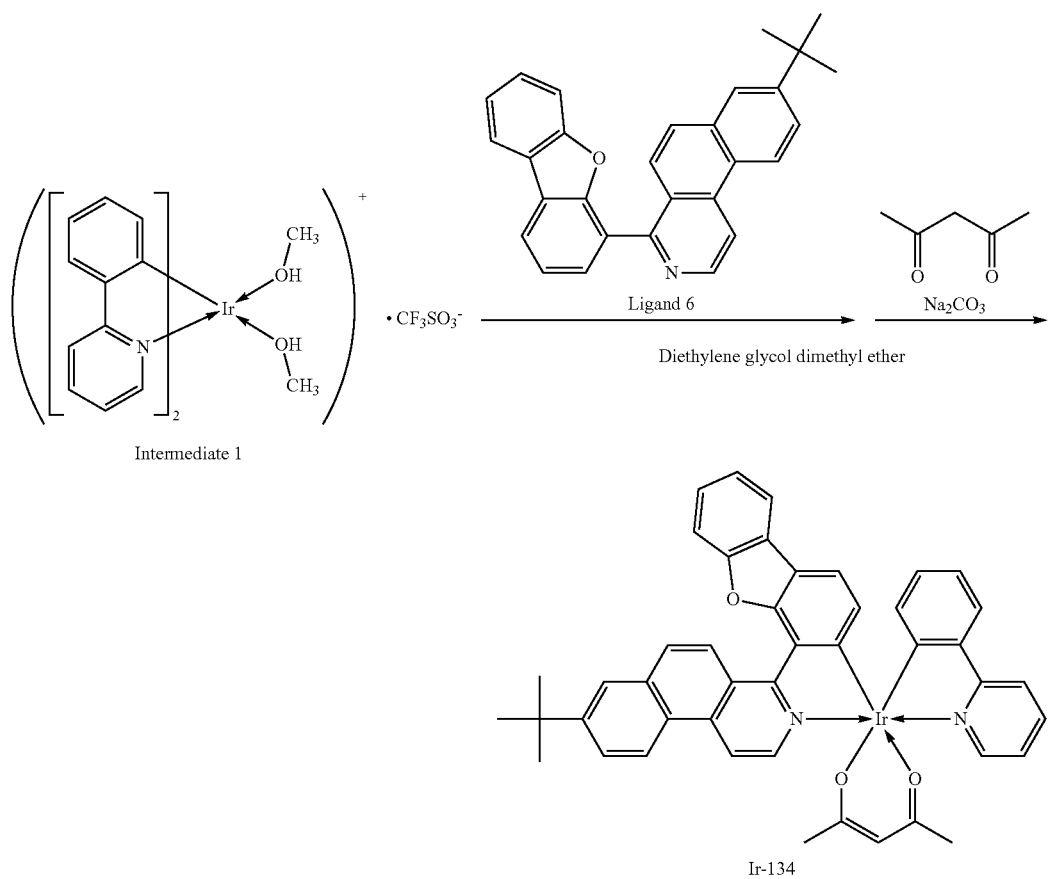

(1) Synthesis of Ligand 6

Ligand 6 was obtained by the same method as that of the section (2) of Synthesis Example 6 except that in the section (2) of Synthesis Example 6, 4-(dibenzofuranyl)boronic acid (manufactured by Sigma-Aldrich) was used instead of 3-methylphenylboronic acid.

(2) Synthesis of Exemplified Compound Ir-134

Exemplified Compound Ir-134 was obtained by the same method as that of Synthesis Example 1 except that in the section (2) of Synthesis Example 1, Ligand 6 was used instead of Ligand 1.

MALDI-TOF MS confirmed that the compound had an $M^+$ of 846.2.

In addition, the phosphorescence spectrum of Exemplified Compound Ir-134 in a dilute toluene solution state was measured in the same manner as in Synthesis Example 1. As a result, its peak wavelength was 608 nm.

Synthesis Example 8

Synthesis of Exemplified Compound Ir-116

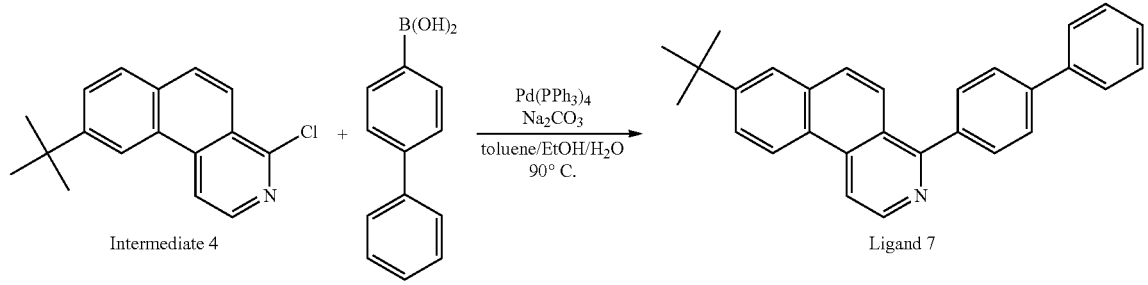

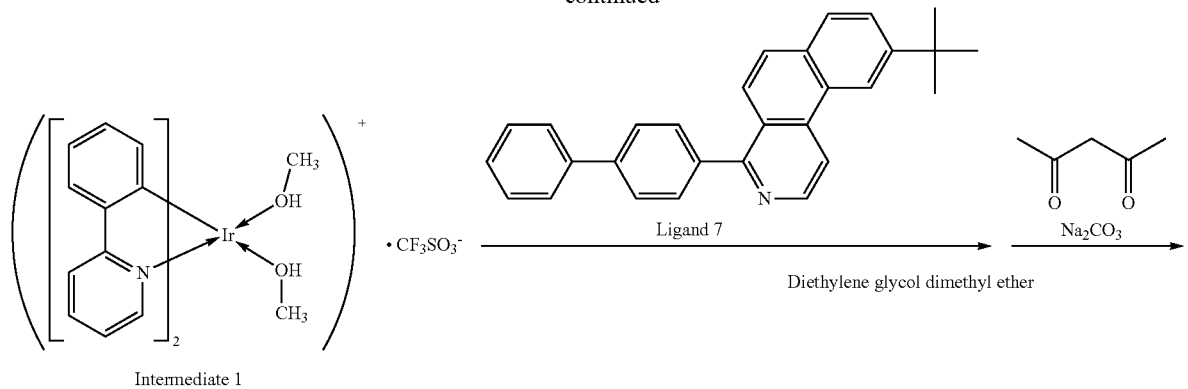

(1) Synthesis of Ligand 7

Intermediate 4 was obtained by the same method as that of the section (1) of Synthesis Example 6 except that in the section (1) of Synthesis Example 6, 3-tert-butylphenylboronic acid (manufactured by Wako Pure Chemical Industries, Ltd.) was used instead of 4-tert-butylphenylboronic acid.

Next, Ligand 7 was obtained by the same method as that of the section (2) of Synthesis Example 6 except that in the section (2) of Synthesis Example 6, Intermediate 4 was used instead of Intermediate 3 and 4-biphenylboronic acid (manufactured by Tokyo Chemical Industry Co., Ltd.) was used instead of 3-methylphenylboronic acid.

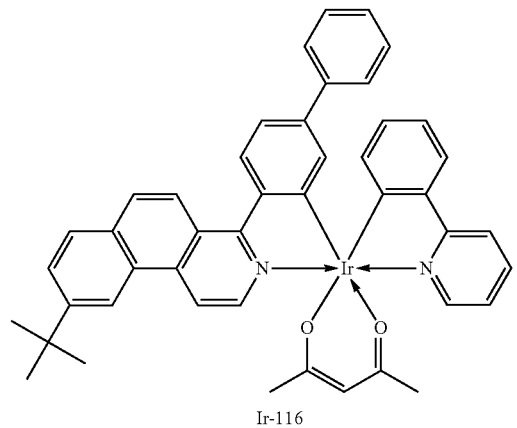

Ir-116

(2) Synthesis of Exemplified Compound Ir-116

Exemplified Compound Ir-116 was obtained by the same method as that of Synthesis Example 1 except that in Synthesis Example 1, Ligand 7 was used instead of Ligand 1.

MALDI-TOF MS confirmed that the compound had an $M^+$ of 832.3.

In addition, the phosphorescence spectrum of Exemplified Compound Ir-116 in a dilute toluene solution state was measured in the same manner as in Synthesis Example 1. As a result, its peak wavelength was 609 nm.

Synthesis Example 9

Synthesis of Exemplified Compound Ir-201

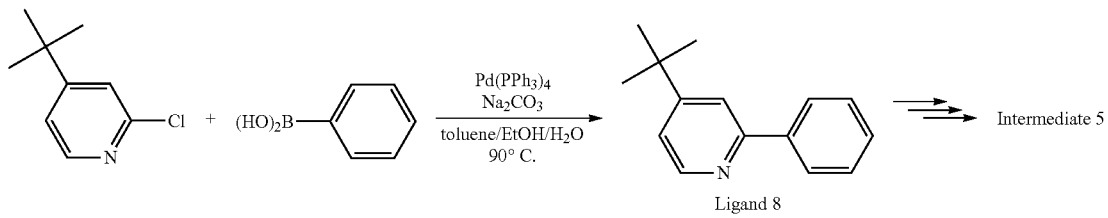

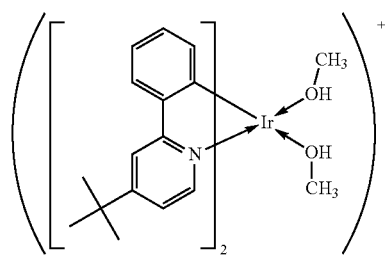

Intermediate 5

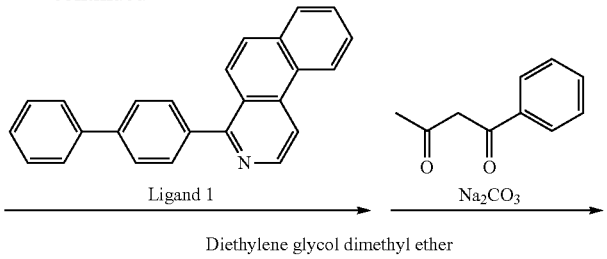

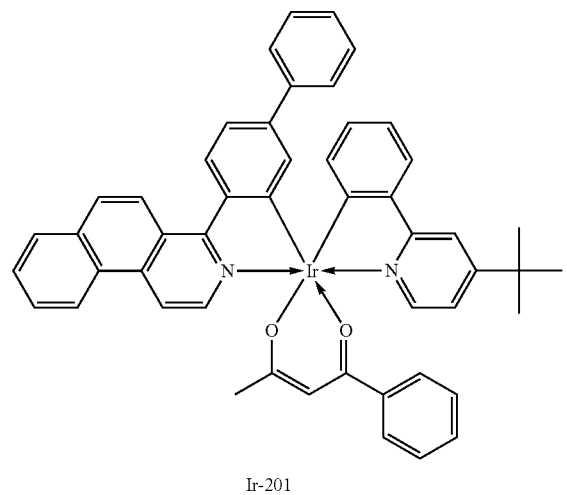

Ir-201

(1) Synthesis of Ligand 8

Ligand 8 was synthesized according to the scheme by using 2-chloro-4-tert-butylpyridine synthesized by the method described in Non Patent Literature 1 and phenylboronic acid (Tokyo Chemical Industry Co., Ltd.) as starting raw materials.

(2) Synthesis of Exemplified Compound Ir-201

Intermediate 5 was obtained by the same method as that of the section (1) of Synthesis Example 1 except that in the section (1) of Synthesis Example 1,2-phenyl-4-tert-butylpyridine was used instead of 2-phenylpyridine.

Next, Exemplified Compound Ir-201 was obtained by the same method as that of Synthesis Example 1 except that in the section (2) of Synthesis Example 1, Intermediate 5 was used instead of Intermediate 1 and 1-phenyl-1,3-butanedione (manufactured by Tokyo Chemical Industry Co., Ltd.) was used instead of acetylacetone.

MALDI-TOF MS confirmed that the compound had an $M^+$ of 894.3.

In addition, the phosphorescence spectrum of Exemplified Compound Ir-201 in a dilute toluene solution state was measured in the same manner as in Synthesis Example 1. As a result, its peak wavelength was 610 nm.

Synthesis Example 10

Synthesis of Exemplified Compound Ir-204

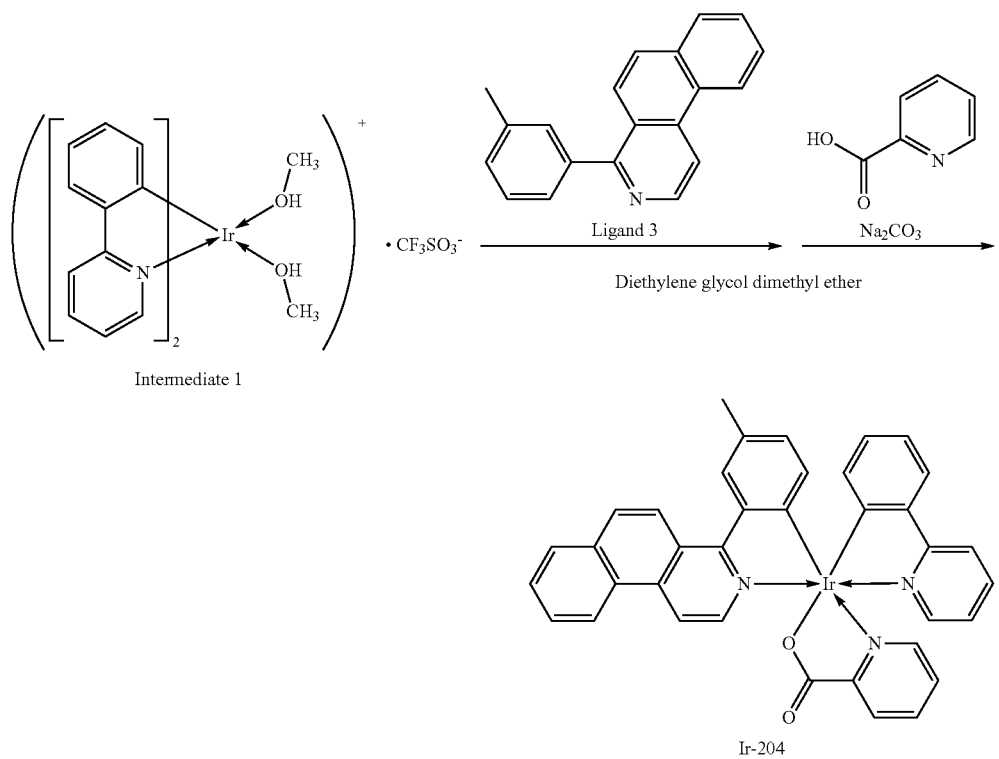

Exemplified Compound Ir-204 was obtained by the same method as that of Synthesis Example 1 except that in the section (2) of Synthesis Example 1, Ligand 3 was used instead of Ligand 1 and pyridine-2-carboxylic acid (manufactured by Tokyo Chemical Industry Co., Ltd.) was used instead of acetylacetone.

MALDI-TOF MS confirmed that the compound had an $M^+$ of 737.2.

In addition, the phosphorescence spectrum of a dilute toluene solution of Exemplified Compound Ir-204 was measured in the same manner as in Synthesis Example 1. As a result, its peak wavelength was 597 nm.

Synthesis Example 11

Synthesis of Exemplified Compound H201

Exemplified Compound H201 was synthesized by a synthesis scheme shown below, specifically, by performing a complexation reaction in methanol involving using quinolin-8-ol as a staring raw material.

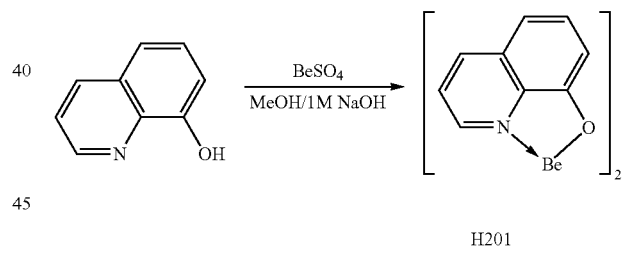

Synthesis Example 12

Synthesis of Metal Complex Serving as Host

Exemplified compounds shown below can each be synthesized by appropriately changing the starting raw material (compound serving as a ligand) in Synthesis Example 11.

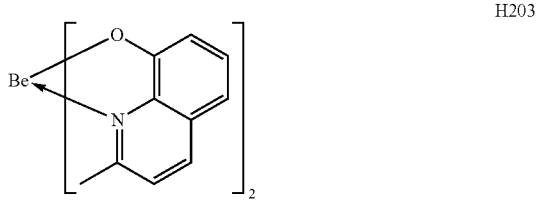

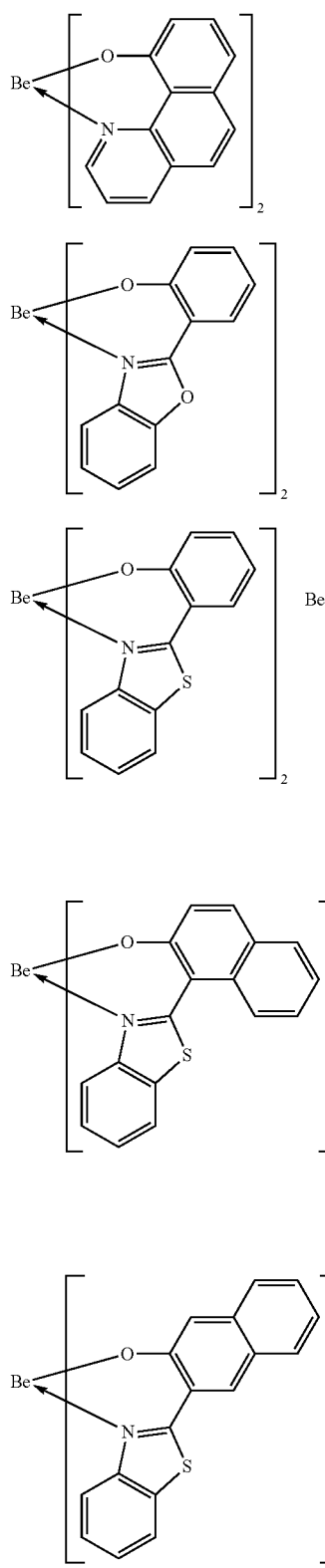

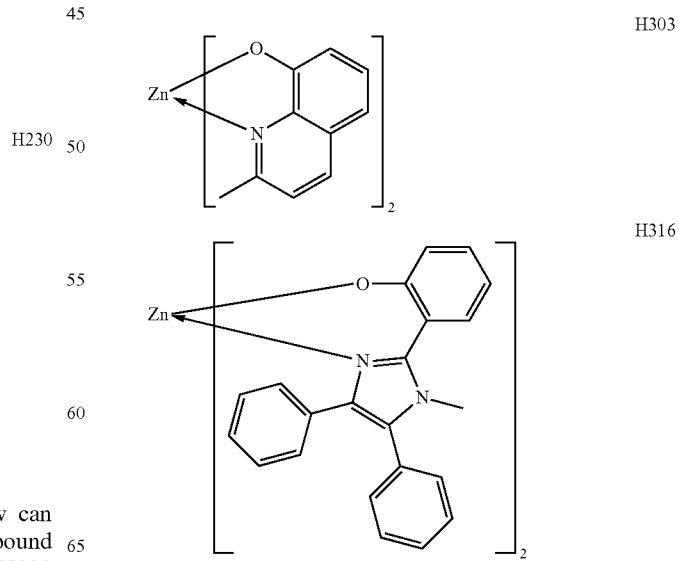

Meanwhile, Exemplified Compound H303 shown below can be synthesized by changing the metal compound reagent to be used upon synthesis of H203 from BeSO₄ to Zn(CH₃COO)₂/2H₂O. In addition, Exemplified Compound H316 shown below can be synthesized by appropriately changing the starting raw material (compound serving as a ligand) upon synthesis of Exemplified Compound H303.

In addition, exemplified compounds shown below can each be synthesized by changing the metal compound reagent to be used upon synthesis of H219, H226, or H229 in the compound group from BeSO₄ to Mg(NO₃)₂.

Example 1

In this example, an organic light-emitting element having a construction in which "an anode/a hole transport layer/an electron blocking layer/an emission layer/a hole blocking layer/an electron transport layer/a cathode" were formed on a substrate in the stated order was produced by the following method.

First, ITO was formed into a film on a glass substrate to form an ITO film. At this time, the thickness of the ITO film was set to 100 nm. Next, the ITO film was subjected to desired patterning processing to form an ITO electrode (anode). The substrate on which the ITO electrode had been thus formed was used as an ITO substrate in the following steps.

Next, organic compound layers and electrode layers shown in Table 2 below were continuously formed on the ITO substrate by a vacuum vapor deposition method. It should be noted that at this time, the electrode area of the opposing electrode (metal electrode layers, cathode) was set to 3 mm$^2$.

TABLE 2

|  | Material | Thickness (nm) |
| --- | --- | --- |
| Hole injection layer: HTL | HT2 | 40 |
| Electron blocking layer: EBL | HT7 | 10 |
| Emission layer | Host: H226 | 30 |
| HOST | Guest: Ir-116 |  |
| GUEST | (H226:Ir-116 = 96:4 (weight ratio)) |  |
| Hole blocking layer: HBL | ET3 | 10 |
| Electron transport layer: ETL | ET2 | 50 |
| First metal electrode layer | LiF | 0.5 |
| Second metal electrode layer | Al | 100 |

Finally, the produced element was sealed with a glass cap with a moisture absorbent in an inert atmosphere to provide an organic light-emitting element.

The element characteristics of the resultant element were measured and evaluated. The organic light-emitting element had a maximum emission wavelength of 619 nm and chromaticity coordinates (x, y) of (0.66, 0.34).

In addition, the current-voltage characteristics of the organic light-emitting element were measured with a microammeter 4140B manufactured by Hewlett-Packard Company, and its emission luminance was measured with a BM7 manufactured by TOPCON CORPORATION.

As a result, the element had a light-emitting efficiency at the time of its light emission at a luminance of 2,000 cd/m$^2$ of 25 cd/A and a luminance half lifetime at a current value of 100 mA/cm$^2$ of 300 hours.

Examples 2 to 15 and Comparative Example 1

Organic light-emitting elements were each produced by the same method as that of Example 1 except that the compounds used as the hole transport layer (HTL), the electron blocking layer (EBL), the emission layer host (HOST), the emission layer guest (GUEST), the hole blocking layer (HBL), and the electron transport layer (ETL) were appropriately changed to compounds shown in Table 2. The element characteristics of the resultant elements were measured and evaluated in the same manner as in Example 1. Table 3 shows the results of the measurement.

TABLE 3

|  | HTL | EBL | HOST | GUEST | HBL | ETL | Light-emitting efficiency at 2,000 cd/m$^2$ [ca/A] |
| --- | --- | --- | --- | --- | --- | --- | --- |
| Example 1 | HT2 | HT7 | H226 | Ir-106 | ET3 | ET2 | 25 |
| Example 2 | HT2 | HT7 | H119 | Ir-106 | ET3 | ET2 | 23 |
| Example 3 | HT1 | HT8 | H126 | Ir-108 | ET3 | ET2 | 23 |
| Example 4 | HT1 | HT8 | H129 | Ir-113 | ET3 | ET2 | 22 |
| Example 5 | HT1 | HT7 | H201 | Ir-106 | ET4 | ET2 | 24 |
| Example 6 | HT1 | HT7 | H203 | Ir-114 | ET4 | ET1 | 24 |
| Example 7 | HT2 | HT8 | H207 | Ir-106 | ET3 | ET2 | 24 |
| Example 8 | HT2 | HT7 | H207 | Ir-116 | ET3 | ET2 | 22 |
| Example 9 | HT2 | HT11 | H219 | Ir-106 | ET4 | ET1 | 24 |
| Example 10 | HT2 | HT7 | H226 | Ir-113 | ET3 | ET1 | 23 |
| Example 11 | HT1 | HT7 | H229 | Ir-114 | ET4 | ET2 | 23 |
| Example 12 | HT2 | HT8 | H229 | Ir-106 | ET3 | ET2 | 25 |
| Example 13 | HT2 | HT7 | H230 | Ir-108 | ET3 | ET2 | 25 |
| Example 14 | HT2 | HT7 | H303 | Ir-134 | ET7 | ET2 | 25 |
| Example 15 | HT1 | HT7 | H316 | Ir-201 | ET3 | ET2 | 23 |
| Comparative Example 1 | HT1 | HT8 | H226 | RD4 | ET3 | ET2 | 13 |

The organic light-emitting element of Comparative Example 1 has a lower light-emitting efficiency than those of the organic light-emitting elements of Examples. This is caused by the fact that efficient energy transfer from the material complex as the host to the guest does not occur in addition to the fact that the guest in the emission layer is not a big-based Ir complex. In view of the foregoing, it can be said that the organic light-emitting element of the present invention is an organic light-emitting element having high heat stability and high efficiency.

REFERENCE SIGNS LIST

18 TFT element
21 Anode
22 Organic compound layer
23 Cathode

As described above with reference to the embodiments and Examples, according to the present invention, it is possible to provide the excellent organic light-emitting element having high light-emitting efficiency and a long element lifetime.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-006321, filed on Jan. 17, 2013, which is hereby incorporated by reference herein in its entirety.

The invention claimed is:

1. An organic light-emitting element comprising:
an anode;
a cathode; and
an organic compound layer placed between the anode and the cathode,
wherein the organic compound layer includes an iridium complex represented by the following general formula [1] and a metal complex represented by the following general formula [9]:

$$Ir(L_1)(L_2)(L_3) \quad [1]$$

in the formula [1], a partial structure IrL$_1$ comprises a partial structure represented by the following general formula [2]:

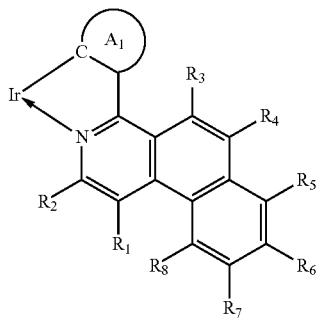

[2]

in the formula [2]:
a ring A$_1$ represents an aromatic ring or an aromatic heterocycle, and the aromatic ring and aromatic heterocycle each represented by the ring A$_1$ may each further have a substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group; and R$_1$ to R$_8$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and may be identical to or different from one another, and when any one of substituents represented by the R$_1$ to R$_8$ is an alkyl group having 1 or more and 4 or less carbon atoms, an aralkyl group, an aryl group, a heterocyclic group, a substituted amino group, an alkoxy group, or an aryloxy group, the substituent may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group;

in the formula [1], a partial structure IrL$_2$ comprises a partial structure represented by the following general formula [3]:

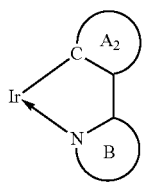

[3]

in the formula [3]:
a ring A$_2$ represents an aromatic ring or an aromatic heterocycle, and the aromatic ring and aromatic heterocycle each represented by the ring A$_2$ may each further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group; and a ring B represents a nitrogen-containing aromatic heterocycle, and the nitrogen-containing aromatic heterocycle represented by the ring B may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group;

L$_1$ and L$_2$ represent ligands that are different from each other and are not identical to each other;

in the formula [1], L$_3$ represents a monovalent bidentate ligand having an atom that forms a covalent bond with iridium and is selected from N, O, S, and P, and an atom that forms a coordinate bond with iridium and is selected from N, O, S, and P, and the atom that forms the covalent bond with iridium and the atom that forms the coordinate bond with iridium may be identical to or different from each other;

MLL'  [9]

in the formula [9], M represents a divalent metal atom selected from Zn, Be, Mg, Ca, Co, and Ni, L and L' each represent a bidentate ligand, and L and L' may be identical to or different from each other, and ML and ML' each represent any one of partial structures represented by the following general formulae [10] to [15]:

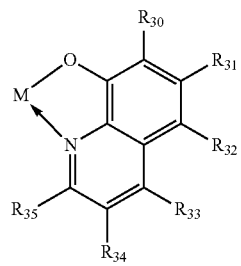

[10]

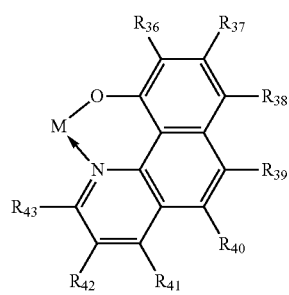

[11]

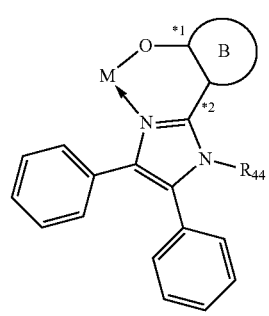

[12]

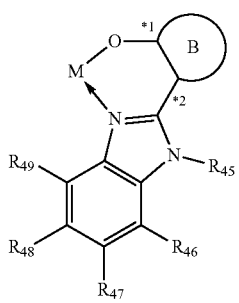

[13]

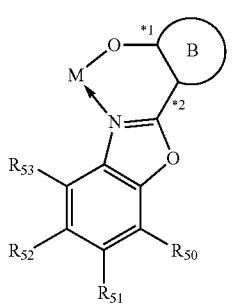

[14]

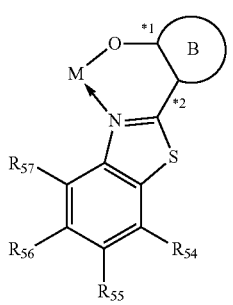

[15]

in the formulae [10] to [15], $R_{30}$ to $R_{57}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group;

in the formulae [12] to [15]:

a ring B comprises any one of cyclic structures represented by the following general formulae [16] to [18]; and

*1 represents a bonding position with an oxygen atom and *2 represents a bonding position with a carbon atom in a five-membered heterocyclic skeleton:

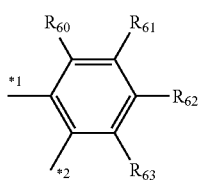

[16]

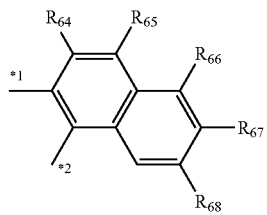

[17]

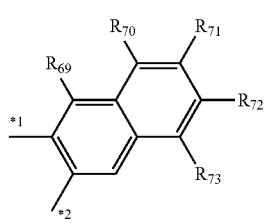

[18]

in the formulae [16] to [18], $R_{60}$ to $R_{73}$ each represent a hydrogen atom, a halogen atom, a substituted or unsubstituted alkyl group, an alkoxy group, a substituted amino group, a substituted or unsubstituted aromatic hydrocarbon group, or a substituted or unsubstituted heteroaromatic group.

2. The organic light-emitting element according to claim 1, wherein the ring $A_1$ is a benzene ring, a naphthalene ring, a fluorene ring, a phenanthrene ring, a carbazole ring, a dibenzofuran ring, or a dibenzothiophene ring; and the ring $A_1$ may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

3. The organic light-emitting element according to claim 1, wherein the partial structure represented by the general formula [2] comprises a partial structure represented by the following general formula [4]:

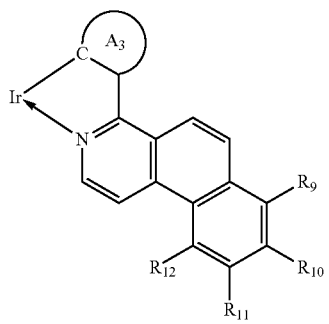

[4]

in the general formula [4]:

a ring $A_3$ is a benzene ring, a naphthalene ring, a fluorene ring, a phenanthrene ring, a carbazole ring, a dibenzofuran ring, or a dibenzothiophene ring, and the ring $A_3$ may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group; and $R_9$ to $R_{12}$ each represent a hydrogen atom, an alkyl group having 1 or more and 4 or less carbon atoms, or a phenyl group, and when any one of substituents represented by $R_9$ to $R_{12}$ is an alkyl group having 1 or more and 4 or less carbon atoms, or a phenyl group, the substituent may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group, and $R_9$ to $R_{12}$ may be identical to or different from one another.

4. The organic light-emitting element according claim 1, wherein the ring $A_2$ is a benzene ring, a naphthalene ring, a fluorene ring, a phenanthrene ring, a carbazole ring, a dibenzofuran ring, or a dibenzothiophene ring;

the ring $A_2$ may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group;

the ring B is a pyridine ring, a quinoline ring, an isoquinoline ring, a benzo[f]quinoline ring, a benzo[h]quinoline ring, a benzo[f]isoquinoline ring, a benzo[h]isoquinoline ring, an oxazole ring, a benzo[d]oxazole ring, a benzo[d]thiazole ring, or an imidazole ring; and the ring B may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

5. The organic light-emitting element according to claim 1, wherein the partial structure represented by the general formula [3] comprises a partial structure represented by the following general formula [5]:

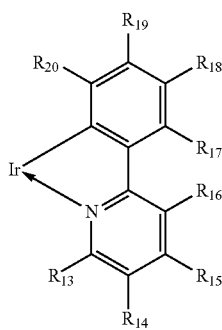

[5]

in the formula [5], $R_{13}$ to $R_{20}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and may be identical to or different from one another, and when any one of substituents represented by $R_{13}$ to $R_{20}$ is an alkyl group having 1 or more and 4 or less carbon atoms, an aralkyl group, an aryl group, a heterocyclic group, a substituted amino group, an alkoxy group, or an aryloxy group, the substituent may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

6. The organic light-emitting element according to claim 5, wherein the $R_{13}$ to $R_{20}$ each represent a hydrogen atom, an alkyl group having 1 or more and 4 or less carbon atoms, or a phenyl group; and the $R_{13}$ to $R_{20}$ may be identical to or different from one another, and when any one of the substituents represented by the $R_{13}$ to $R_{20}$ is an alkyl group having 1 or more and 4 or less carbon atoms, or a phenyl group, the substituent may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

7. The organic light-emitting element according to claim 1, wherein in the general formula [1], a partial structure $IrL_3$ comprises a partial structure represented by the following general formula [6]:

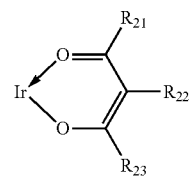

[6]

in the formula [6], $R_{21}$ to $R_{23}$ each represent a hydrogen atom, an alkyl group having 1 or more and 4 or less carbon atoms, an aralkyl group, an aryl group, a heterocyclic group, a substituted amino group, an alkoxy group, an aryloxy group, a halogen atom, or a cyano group, and may be identical to or different from one another, and when any one of substituents represented by $R_{21}$ to $R_{23}$ is an alkyl group having 1 or more and 4 or less carbon atoms, an aralkyl group, an aryl group, a heterocyclic group, a substituted amino group, an alkoxy group, or an aryloxy group, the substituent may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

8. The organic light-emitting element according to claim 7, wherein the $R_{21}$ to $R_{23}$ each represent a hydrogen atom or an alkyl group having 1 or more and 4 or less carbon atoms; and when any one of the substituents represented by the $R_{21}$ to $R_{23}$ is an alkyl group having 1 or more and 4 or less carbon atoms, the substituent may further have any substituent selected from an alkyl group having 1 or more and 4 or less carbon atoms, an aralkyl group, an aryl group, a heterocyclic group, a substituted amino group, an alkoxy group, an aryloxy group, a halogen atom, and a cyano group.

9. A display apparatus comprising multiple pixels, wherein the pixels each have the organic light-emitting element according claim 1 and an active element connected to the organic light-emitting element.

10. The display apparatus according to claim 9, wherein an electrode of the active element is formed of a transparent oxide semiconductor.

11. The display apparatus according to claim 9, further comprising a color filter.

12. A display apparatus, which is formed by laminating the organic light-emitting element according to claim 1 to thereby output white light as a whole.

13. A lighting apparatus comprising:
the organic light-emitting element according to claim 1; and
an inverter circuit connected to the organic light-emitting element.

* * * * *